(12) United States Patent
Bhalla et al.

(10) Patent No.: US 9,663,759 B2
(45) Date of Patent: May 30, 2017

(54) PARTIAL ADAPTATION FOR BUTANOL PRODUCTION

(71) Applicant: BUTAMAX ADVANCED BIOFUELS LLC, Wilmington, DE (US)

(72) Inventors: Ritu Bhalla, Tirmulgherry (IN); Steven D. Doig, Wilmington, DE (US); Kakasaheb Suresh Konde, Maharashtra (IN); Ranjan Patnaik, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 250 days.

(21) Appl. No.: 14/320,681

(22) Filed: Jul. 1, 2014

(65) Prior Publication Data
US 2015/0010984 A1 Jan. 8, 2015

Related U.S. Application Data

(60) Provisional application No. 61/842,817, filed on Jul. 3, 2013.

(51) Int. Cl.
| C12N 1/36 | (2006.01) |
| C12P 7/16 | (2006.01) |
| C12N 15/52 | (2006.01) |

(52) U.S. Cl.
CPC ............ *C12N 1/36* (2013.01); *C12N 15/52* (2013.01); *C12P 7/16* (2013.01); *Y02E 50/10* (2013.01)

(58) Field of Classification Search
None
See application file for complete search history.

(56) References Cited

U.S. PATENT DOCUMENTS

| 4,284,724 | A | 8/1981 | Fukuda et al. |
| 4,414,329 | A | 11/1983 | Wegner |
| 4,424,275 | A | 1/1984 | Levy |
| 4,443,542 | A | 4/1984 | Hayashida et al. |
| 4,520,104 | A | 5/1985 | Heady et al. |
| 4,765,992 | A | 8/1988 | Geneix et al. |
| 4,777,135 | A | 10/1988 | Husted et al. |
| 4,845,033 | A | 7/1989 | Tegtmeier |
| 5,063,156 | A | 11/1991 | Glassner et al. |
| 5,514,583 | A | 5/1996 | Picataggio et al. |
| 5,686,276 | A | 11/1997 | Laffend et al. |
| 5,712,133 | A | 1/1998 | Picataggio et al. |
| 6,358,717 | B1 | 3/2002 | Blaschek et al. |
| 6,432,688 | B1 | 8/2002 | Ito et al. |
| 7,223,575 | B2 | 5/2007 | Zhang et al. |
| 7,574,601 | B2 | 8/2009 | Jahromi et al. |
| 7,741,119 | B2 | 6/2010 | Viitanen et al. |
| 7,851,188 | B2 | 12/2010 | Donaldson et al. |
| 7,910,342 | B2 | 3/2011 | Liao et al. |
| 7,993,388 | B2 | 8/2011 | Lee et al. |
| 7,993,889 | B1 | 8/2011 | Donaldson et al. |
| 8,129,162 | B2 | 3/2012 | Li et al. |
| 8,178,328 | B2 | 5/2012 | Donaldson et al. |
| 8,206,970 | B2 | 6/2012 | Eliot et al. |
| 8,241,878 | B2 | 8/2012 | Anthony et al. |
| 8,465,964 | B2 | 6/2013 | Anthony et al. |
| 8,980,612 | B2 | 3/2015 | Donaldson et al. |
| 2005/0089979 | A1 | 4/2005 | Ezeji et al. |
| 2007/0031918 | A1 | 2/2007 | Dunson et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2008/0274524 | A1 | 11/2008 | Bramucci et al. |
| 2008/0274525 | A1 | 11/2008 | Bramucci et al. |
| 2008/0274526 | A1 | 11/2008 | Bramucci et al. |
| 2009/0035826 | A1 | 2/2009 | Tolan et al. |
| 2009/0047718 | A1 | 2/2009 | Blaschek et al. |
| 2009/0081746 | A1 | 3/2009 | Liao et al. |
| 2009/0111154 | A1 | 4/2009 | Liao et al. |
| 2009/0155869 | A1 | 6/2009 | Buelter et al. |
| 2009/0155870 | A1 | 6/2009 | Donaldson et al. |

(Continued)

FOREIGN PATENT DOCUMENTS

| CN | 101418320 | 4/2009 |
| JP | 63269988 | 11/1988 |

(Continued)

OTHER PUBLICATIONS

Van Maris, et al., Directed Evolution of Pyruvate Decarboxylase-Negative *Saccharomyces cerevisiae*, Yielding a C2-Independent, Glucose-Tolerant, and Pyruvate-Hyperproducing Yeast, Appl. Environ. Microbiol. 70:159-166, 2004.
Tashiro, et al., High production of acetone-butanol-ethanol with high cell density culture by cell-recycling and bleeding, J. Biotechnol. 120:197-206, 2005.
Srinivasan, et al., A Novel High-Cell-Density Protein Expression System Based on Ralstonia eutropha, Appl. Environ. Microbiol. 68:5925-5932, 2002.
Guo, et al., Studies on characteristics of kinetics and metabolic shift of genetically engineered yeast Pichia pastoris in high-density chemostat cultivation, Wei Sheng Wu Xue Bao 41:617-623, 2001 (Abstract only).
Knoshaug et al., Butanol Tolerance in a Selection of Microorganisms., Appl. Biochem. Biotechnol. 153:13-20, 2009.
Bigelis, et al., Exogenous Valine Reduces Conversion of Leucine to 3-Methyl-1-Butanol in *Saccharomyces cerevisiae.*, Appl Environ Microbiol. 45:658-664, 1983.

(Continued)

*Primary Examiner* — Suzanne M Noakes
*Assistant Examiner* — Jae W Lee

(57) ABSTRACT

Provided herein are processes for producing an improved culture of cells comprising an engineered butanol biosynthetic pathway. The processes comprise (a) providing a cell culture of recombinant microorganisms comprising an engineered butanol biosynthetic pathway, wherein the engineered butanol biosynthetic pathway is minimal or not activated; and (b) growing the culture of recombinant microorganisms under adaptive conditions whereby pathway activation is increased to produce an improved cell culture and whereby the improved cell culture is capable of continuing to grow in fermentation.

19 Claims, No Drawings

(56) References Cited

U.S. PATENT DOCUMENTS

| | | | |
|---|---|---|---|
| 2009/0162912 | A1 | 6/2009 | Ezeji et al. |
| 2009/0163376 | A1 | 6/2009 | Li et al. |
| 2009/0171129 | A1 | 7/2009 | Evanko et al. |
| 2009/0176288 | A1 | 7/2009 | Burd et al. |
| 2009/0203099 | A1 | 8/2009 | Caimi et al. |
| 2009/0203139 | A1 | 8/2009 | Larossa et al. |
| 2009/0226991 | A1 | 9/2009 | Feldman et al. |
| 2009/0246846 | A1 | 10/2009 | Viitanen et al. |
| 2009/0269823 | A1 | 10/2009 | Bramucci et al. |
| 2009/0280546 | A1 | 11/2009 | Larossa |
| 2009/0305363 | A1 | 12/2009 | Anthony et al. |
| 2009/0305370 | A1 | 12/2009 | Grady et al. |
| 2010/0081154 | A1 | 4/2010 | Flint et al. |
| 2010/0120105 | A1 | 5/2010 | Anthony et al. |
| 2010/0197519 | A1 | 8/2010 | Li et al. |
| 2011/0097773 | A1 | 4/2011 | Grady et al. |
| 2011/0097775 | A1* | 4/2011 | Green ............... C12N 9/0006 435/160 |
| 2011/0111472 | A1 | 5/2011 | Donaldson et al. |
| 2011/0124060 | A1 | 5/2011 | Anthony et al. |
| 2011/0159558 | A1 | 6/2011 | Grady et al. |
| 2011/0250610 | A1 | 10/2011 | Liao et al. |
| 2011/0269199 | A1 | 11/2011 | Satagopan et al. |
| 2011/0313206 | A1 | 12/2011 | Donaldson et al. |
| 2012/0064561 | A1 | 3/2012 | Flint et al. |
| 2012/0149080 | A1* | 6/2012 | Nagarajan ............. C12N 1/16 435/160 |
| 2012/0237988 | A1 | 9/2012 | Anthony et al. |
| 2012/0258873 | A1 | 10/2012 | Gibson et al. |
| 2013/0071898 | A1 | 3/2013 | Anthony et al. |
| 2014/0004526 | A1 | 1/2014 | Dauner et al. |
| 2014/0093930 | A1 | 4/2014 | Li et al. |

FOREIGN PATENT DOCUMENTS

| | | |
|---|---|---|
| WO | WO2007041269 | 4/2007 |
| WO | WO2007050671 | 5/2007 |
| WO | WO2007130521 | 11/2007 |
| WO | WO2007130518 | 11/2007 |
| WO | WO2008080124 | 7/2008 |
| WO | WO2009013157 | 1/2009 |
| WO | WO2009046370 | 4/2009 |
| WO | WO2009055072 | 4/2009 |
| WO | WO2009087680 | 7/2009 |
| WO | WO2009103533 | 8/2009 |
| WO | WO2009149270 | 12/2009 |
| WO | WO2010075241 | 7/2010 |
| WO | WO2010151832 | 12/2010 |
| WO | WO2011041415 | 4/2011 |
| WO | WO2011103300 | 8/2011 |
| WO | WO2012129555 | 9/2012 |
| WO | WO2013061571 | 5/2013 |
| WO | WO2013086222 | 6/2013 |

OTHER PUBLICATIONS

Heyland, et al.; Correlation between TCA cycle flux and glucose uptake rate during respiro-fermentative growth of *Saccharomyces cerevisiae.*, Microbiol. 155:3827-3837, 2009.

Lameiras, Butanol production in Lactic acid bacteria, Gothenburg, Sweden, 2012, pp. 1-56.

Lynch, Evolution of the mutation rate, Trends in Genetics 26:345-352, 2010.

Kadam, et al., Evaluation of Candida acidothermophilum in ethanol production from lignocellulosic biomass, Appl. Microbiol. Biotechnol. 48:709-713, 1997.

Lorenz, et al., Characterization of Alcohol-induced Filamentous Growth in *Saccharomyces cerevisiae.*, Mol. Biol. Cell. 11:183-199, 2000.

Atsumi, et al., Non-fermentative pathways for synthesis of branched-chain higher alcohols as biofuels, Nature 451:86-90, 2008.

Afschar, et al., Production of acetone and butanol by Clostridium acetobutylicum in continuous culture with cell recycle, Appl. Microbiol. Biotechnol. 22:394-398, 1985.

Deshpande, Ethanol Production from Cellulose by Coupled Saccharification/Fermentation using *Saccharomyces cerevisiae* and Cellulase Complex from Sclerotium rolfsii UV-8 Mutant, Appl. Biochem. Biotechnol. 36: 227-234, 1992.

Diderich, et al., Strategies to determine the extent of control exerted by glucose transport on glycolytic flux in the yeast *Saccharomyces bayanus*, Microbiology 145:3447-3454, 1999.

Durre, New insights and novel developments in clostridial acetone/butanol/isopropanol fermentation, Appl. Microbiol. Biotechnol. 49:639-648, 1998.

Groot, et al., Technologies for Butanol Recovery Integrated with Fermentations, Process Chemistry 27:61-75, 1992.

Keay, et al., Improved production of ethanol and n-butanol in immobilized cell bioreactors, Physiology Immobilized Cells 539-543, 1990 (Conference, Abstract only).

Zhang, et al., Metabolic Engineering of a Pentose Metabolism Pathway in Ethanologenic Zymomonas mobilis, Science 267:240-243, 1995.

Lingqiao, et al., Study of the Treatment of Acetone-Butanol Fermentation Wastewater by Yeast, Industrial Water Treatment 28:1-7, 2008.

Steen et al., Metabolic engineering of *Saccharomyces cerevisiae* for the production n-butanol, Microbial Cell Factories 7:1-8, 2008.

Yang, et al., Enhanced Acetone-Butanol Fermentation Using Repeated Fed-Batch Operation Coupled with Cell Recycle by Membrane and Simultaneous Removal of Inhibitory Products by Adsorption, Biotechnol. Bioengineer. 47:444-450, 1995.

Van Urk, et al., Glucose Transport in Crabtree-positive and Crabtree-negative Yeasts, Microbiology 135:2399-2406, 1989.

Sonnleitner, et al., Dynamics of Glucose Consumption in Yeast, Biotechnol. Progress 13:8-13, 1997.

Tabor, et al., A bacteriophage T7 RNA polymerase/promoter system for controlled exclusive expression of specific genes, Proc. Natl. Acad. Sci. USA 82:1074-1078, 1985.

Aden, et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.

Bellion, et al., Microb. Growth C1 Compd., [IntSymp.], 7th(1993), 415 32. Editor(s): Murrell, J. Collin; Kelly, Don P. Publisher: Intercept, Andover, UK.

Feldman, et al., Pentose metabolism in Zymomonas mobilis wild-type and recombinant strains, Appl. Microbiol. Biotechnol. 38:354-361, 1992.

Jones, et al., Microbial Metabolism of Amino Alcohols, Biochem. J, 134:167-182, 1973.

Shen, et al., Metabolic engineering of *Escherichia coli* for 1-butanol and 1-propanol production via the keto-acid pathways, Metabol. Eng. 10:312-320, 2008.

Sulter, et al., Proliferation and metabolic significance of peroxisomes in Candida bodinii during growth on D-alanine or oleic acid as the sole carbon source, Arch. Microbiol. 153:485-489, 1990.

Underwood, et al., Flux through Citrate Synthase Limits the Growth of Ethanologenic *Escherichia coli* KO11 during Xylose Fermentation, Appl. Environ. Microbiol. 68:1071-1081, 2002.

International Search Report and Written Opinion of corresponding PCT/US2014/044986 mailed Oct. 30, 2014.

\* cited by examiner

SEQUENCE LISTING

```
<160> NUMBER OF SEQ ID NOS: 98

<210> SEQ ID NO 1
<211> LENGTH: 4519
<212> TYPE: DNA
<213> ORGANISM: Artificial Sequence
<220> FEATURE:
<223> OTHER INFORMATION: pLA54

<400> SEQUENCE: 1
caccttggct aactcgttgt atcatcactg gataacttcg tataatgtat gctatacgaa      60
gttatcgaac agagaaacta aatccacatt aattgagagt ctatctatt agaaaatgca     120
```

```
aactccaact aaatgggaaa acagataacc tcttttatttt ttttttaatg tttgatattc    180
gagtcttttt cttttgttag gtttatattc atcatttcaa tgaataaaag aagcttctta    240
ttttggttgc aaagaatgaa aaaaaaggat tttttcatac ttctaaagct tcaattataa    300
ccaaaaattt tataaatgaa gagaaaaaat ctagtagtat caagttaaac ttagaaaaac    360
tcatcgagca tcaaatgaaa ctgcaattta ttcatatcag gattatcaat accatatttt    420
tgaaaaagcc gttctgtaa tgaaggagaa aactcaccga ggcagttcca taggatggca    480
agatcctggt atcggtctgc gattccgact cgtccaacat caatacaacc tattaatttc    540
ccctcgtcaa aaataaggtt atcaagtgag aaatcaccat gagtgacgac tgaatccggt    600
gagaatggca aaagcttatg catttctttc cagacttgtt caacaggcca gccattacgc    660
tcgtcatcaa aatcactcgc atcaaccaaa ccgttattca ttcgtgattg cgcctgagcg    720
agacgaaata cgcgatcgct gttaaaagga caattacaaa caggaatcga atgcaaccgg    780
cgcaggaaca ctgccagcgc atcaacaata ttttcacctg aatcaggata ttcttctaat    840
acctggaatg ctgttttgcc ggggatcgca gtggtgagta accatgcatc atcaggagta    900
cggataaaat gcttgatggt cggaagaggc ataaattccg tcagccagtt tagtctgacc    960
atctcatctg taacatcatt ggcaacgcta cctttgccat gtttcagaaa caactctggc   1020
gcatcgggct tcccatacaa tcgatagatt gtcgcacctg attgcccgac attatcgcga   1080
gcccatttat acccatataa atcagcatcc atgttggaat taatcgcgg cctcgaaacg   1140
tgagtctttt ccttacccat ctcgagtttt aatgttactt ctcttgcagt tagggaacta   1200
taatgtaact caaaataaga ttaaacaaac taaaataaaa agaagttata cagaaaaacc   1260
catataaacc agtactaatc cataataata atacacaaaa aaactatcaa ataaaaccag   1320
aaaacagatt gaatagaaaa attttttcga tctccttta tattcaaaat tcgatatatg   1380
aaaaagggaa ctctcagaaa atcaccaaat caatttaatt agattttttct tttccttcta   1440
gcgttggaaa gaaaaatttt tctttttttt tttagaaatg aaaaattttt gccgtaggaa   1500
tcaccgtata aaccctgtat aaacgctact ctgttcacct gtgtaggcta tgattgaccc   1560
agtgttcatt gttattgcga gagagcggga gaaaagaacc gatacaagag atccatgctg   1620
gtatagttgt ctgtccaaca cttttgatgaa cttgtaggac gatgatgtgt atttagacga   1680
gtacgtgtgt gactattaag tagttatgat agagaggttt gtacggtgtg ttctgtgtaa   1740
ttcgattgag aaaatggtta tgaatcccta gataacttcg tataatgtat gctatacgaa   1800
gttatctgaa cattagaata cgtaatccgc aatgcgggga tcctctagag tcgacctgca   1860
ggcatgcaag cttggcgtaa tcatggtcat agctgtttcc tgtgtgaaat tgttatccgc   1920
tcacaattcc acacaacata cgagccggaa gcataaagtg taaagcctgg ggtgcctaat   1980
gagtgagcta actcacatta attgcgttgc gctcactgcc cgctttccag tcgggaaacc   2040
tgtcgtgcca gctgcattaa tgaatcggcc aacgcgcggg gagaggcggt ttgcgtattg   2100
ggcgctcttc cgcttcctcg ctcactgact cgctgcgctc ggtcgttcgg ctgcggcgag   2160
cggtatcagc tcactcaaag gcggtaatac ggttatccac agaatcaggg gataacgcag   2220
gaaagaacat gtgagcaaaa ggccagcaaa aggccaggaa ccgtaaaaag gccgcgttgc   2280
tggcgttttt ccataggctc cgcccccctg acgagcatca caaaaatcga cgctcaagtc   2340
agaggtggcg aaacccgaca ggactataaa gataccaggc gtttccccct ggaagctccc   2400
tcgtgcgctc tcctgttccg accctgccgc ttaccggata cctgtccgcc tttctccctt   2460
cgggaagcgt ggcgctttct catagctcac gctgtaggta tctcagttcg gtgtaggtcg   2520
```

```
ttcgctccaa gctgggctgt gtgcacgaac ccccgttca gcccgaccgc tgcgccttat    2580
ccggtaacta tcgtcttgag tccaacccgg taagacacga cttatcgcca ctggcagcag    2640
ccactggtaa caggattagc agagcgaggt atgtaggcgg tgctacagag ttcttgaagt    2700
ggtggcctaa ctacgctac actagaagga cagtatttgg tatctgcgct ctgctgaagc    2760
cagttacctt cggaaaaaga gttggtagct cttgatccgg caaacaaacc accgctggta    2820
gcggtggttt ttttgtttgc aagcagcaga ttacgcgcag aaaaaaagga tctcaagaag    2880
atcctttgat cttttctacg gggtctgacg ctcagtggaa cgaaaactca cgttaaggga    2940
ttttggtcat gagattatca aaaaggatct cacctagat ccttttaaat taaaaatgaa    3000
gttttaaatc aatctaaagt atatatgagt aaacttggtc tgacagttac caatgcttaa    3060
tcagtgaggc acctatctca gcgatctgtc tatttcgttc atccatagtt gcctgactcc    3120
ccgtcgtgta gataactacg atacgggagg gcttaccatc tggccccagt gctgcaatga    3180
taccgcgaga cccacgctca ccggctccag atttatcagc aataaaccag ccagccggaa    3240
gggccgagcg cagaagtggt cctgcaactt tatccgcctc catccagtct attaattgtt    3300
gccgggaagc tagagtaagt agttcgccag ttaatagttt gcgcaacgtt gttgccattg    3360
ctacaggcat cgtggtgtca cgctcgtcgt ttggtatggc ttcattcagc tccggttccc    3420
aacgatcaag gcgagttaca tgatccccca tgttgtgcaa aaaagcggtt agctccttcg    3480
gtcctccgat cgttgtcaga agtaagttgg ccgcagtgtt atcactcatg gttatggcag    3540
cactgcataa ttctcttact gtcatgccat ccgtaagatg cttttctgtg actggtgagt    3600
actcaaccaa gtcattctga atagtgta tgcggcgacc gagttgctct tgcccggcgt    3660
caatacggga taataccgcg ccacatagca gaactttaaa agtgctcatc attggaaaac    3720
gttcttcggg gcgaaaactc tcaaggatct taccgctgtt gagatccagt tcgatgtaac    3780
ccactcgtgc acccaactga tcttcagcat cttttacttt caccagcgtt tctgggtgag    3840
caaaaacagg aaggcaaaat gccgcaaaaa agggaataag ggcgacacgg aaatgttgaa    3900
tactcatact cttccttttt caatattatt gaagcattta tcagggttat tgtctcatga    3960
gcggatacat atttgaatgt atttagaaaa ataaacaaat aggggttccg cgcacatttc    4020
cccgaaaagt gccacctgac gtctaagaaa ccattattat catgacatta acctataaaa    4080
ataggcgtat cacgaggccc tttcgtctcg cgcgtttcgg tgatgacggt gaaaacctct    4140
gacacatgca gctcccggag acggtcacag cttgtctgta agcggatgcc gggagcagac    4200
aagcccgtca gggcgcgtca gcgggtgttg gcgggtgtcg ggctggctt aactatgcgg    4260 catcagagca gattgtactg agagtgcacc atatgcggtg tgaaataccg cacagatgcg    4320
taaggagaaa ataccgcatc aggcgccatt cgccattcag gctgcgcaac tgttgggaag    4380
ggcgatcggt gcgggcctct tcgctattac gccagctggc gaaaggggga tgtgctgcaa    4440
ggcgattaag ttgggtaacg ccagggtttt cccagtcacg acgttgtaaa acgacggcca    4500
gtgaattcga gctcggtac                                                 4519
```

<210> SEQ ID NO 2
<211> LENGTH: 80
<212> TYPE: DNA
<213> ORGANISM: Artificial Sequence
<220> FEATURE:
<223> OTHER INFORMATION: BK505

<400> SEQUENCE: 2

```
ttccggtttc tttgaaattt ttttgattcg gtaatctccg agcagaagga gcattgcgga    60
ttacgtattc taatgttcag                                                80

<210> SEQ ID NO 3
<211> LENGTH: 81
<212> TYPE: DNA
<213> ORGANISM: Artificial Sequence
<220> FEATURE:
<223> OTHER INFORMATION: BK506

<400> SEQUENCE: 3
gggtaataac tgatataatt aaattgaagc tctaatttgt gagtttagta caccttggct    60
aactcgttgt atcatcactg g                                              81

<210> SEQ ID NO 4
<211> LENGTH: 38
<212> TYPE: DNA
<213> ORGANISM: Artificial Sequence
<220> FEATURE:
<223> OTHER INFORMATION: LA468

<400> SEQUENCE: 4
gcctcgagtt ttaatgttac ttctcttgca gttaggga                            38

<210> SEQ ID NO 5
<211> LENGTH: 31
<212> TYPE: DNA
<213> ORGANISM: Artificial Sequence
<220> FEATURE:
<223> OTHER INFORMATION: LA492

<400> SEQUENCE: 5
gctaaattcg agtgaaacac aggaagacca g                                   31

<210> SEQ ID NO 6
<211> LENGTH: 23
<212> TYPE: DNA
<213> ORGANISM: Artificial Sequence
<220> FEATURE:
<223> OTHER INFORMATION: AK109-1

<400> SEQUENCE: 6
agtcacatca agatcgttta tgg                                            23

<210> SEQ ID NO 7
<211> LENGTH: 23
<212> TYPE: DNA
<213> ORGANISM: Artificial Sequence
<220> FEATURE:
<223> OTHER INFORMATION: AK109-2

<400> SEQUENCE: 7
gcacggaata tgggactact tcg                                            23

<210> SEQ ID NO 8
<211> LENGTH: 23
<212> TYPE: DNA
<213> ORGANISM: Artificial Sequence
<220> FEATURE:
<223> OTHER INFORMATION: AK109-3

<400> SEQUENCE: 8
actccacttc aagtaagagt ttg                                            23
```

```
<210> SEQ ID NO 9
<211> LENGTH: 24
<212> TYPE: DNA
<213> ORGANISM: Artificial Sequence
<220> FEATURE:
<223> OTHER INFORMATION: oBP452

<400> SEQUENCE: 9
ttctcgacgt gggccttttt cttg                                          24

<210> SEQ ID NO 10
<211> LENGTH: 49
<212> TYPE: DNA
<213> ORGANISM: Artificial Sequence
<220> FEATURE:
<223> OTHER INFORMATION: oBP453

<400> SEQUENCE: 10
tgcagcttta aataatcggt gtcactactt tgccttcgtt tatcttgcc               49

<210> SEQ ID NO 11
<211> LENGTH: 49
<212> TYPE: DNA
<213> ORGANISM: Artificial Sequence
<220> FEATURE:
<223> OTHER INFORMATION: oBP454

<400> SEQUENCE: 11
gagcaggcaa gataaacgaa ggcaaagtag tgacaccgat tatttaaag               49

<210> SEQ ID NO 12
<211> LENGTH: 49
<212> TYPE: DNA
<213> ORGANISM: Artificial Sequence
<220> FEATURE:
<223> OTHER INFORMATION: oBP455

<400> SEQUENCE: 12
tatggaccct gaaaccacag ccacattgta accaccacga cggttgttg               49

<210> SEQ ID NO 13
<211> LENGTH: 49
<212> TYPE: DNA
<213> ORGANISM: Artificial Sequence
<220> FEATURE:
<223> OTHER INFORMATION: oBP456

<400> SEQUENCE: 13
tttagcaaca accgtcgtgg tggttacaat gtggctgtgg tttcagggt               49

<210> SEQ ID NO 14
<211> LENGTH: 49
<212> TYPE: DNA
<213> ORGANISM: Artificial Sequence
<220> FEATURE:
<223> OTHER INFORMATION: oBP457

<400> SEQUENCE: 14
ccagaaaccc tatacctgtg tggacgtaag gccatgaagc ttttctttt               49

<210> SEQ ID NO 15
<211> LENGTH: 49
<212> TYPE: DNA
<213> ORGANISM: Artificial Sequence
<220> FEATURE:
<223> OTHER INFORMATION: oBP458
```

-continued

<400> SEQUENCE: 15
attggaaaga aaaagcttca tggccttacg tccacacagg tatagggtt    49

<210> SEQ ID NO 16
<211> LENGTH: 22
<212> TYPE: DNA
<213> ORGANISM: Artificial Sequence
<220> FEATURE:
<223> OTHER INFORMATION: oBP459

<400> SEQUENCE: 16
cataagaaca cctttggtgg ag    22

<210> SEQ ID NO 17
<211> LENGTH: 22
<212> TYPE: DNA
<213> ORGANISM: Artificial Sequence
<220> FEATURE:
<223> OTHER INFORMATION: oBP460

<400> SEQUENCE: 17
aggattatca ttcataagtt tc    22

<210> SEQ ID NO 18
<211> LENGTH: 20
<212> TYPE: DNA
<213> ORGANISM: Artificial Sequence
<220> FEATURE:
<223> OTHER INFORMATION: LA135

<400> SEQUENCE: 18
cttggcagca acaggactag    20

<210> SEQ ID NO 19
<211> LENGTH: 23
<212> TYPE: DNA
<213> ORGANISM: Artificial Sequence
<220> FEATURE:
<223> OTHER INFORMATION: oBP461

<400> SEQUENCE: 19
ttcttggagc tgggacatgt ttg    23

<210> SEQ ID NO 20
<211> LENGTH: 22
<212> TYPE: DNA
<213> ORGANISM: Artificial Sequence
<220> FEATURE:
<223> OTHER INFORMATION: LA92

<400> SEQUENCE: 20
gagaagatgc ggccagcaaa ac    22

<210> SEQ ID NO 21
<211> LENGTH: 4242
<212> TYPE: DNA
<213> ORGANISM: Artificial Sequence
<220> FEATURE:
<223> OTHER INFORMATION: pLA59

<400> SEQUENCE: 21
aaacgccagc aacgcggcct ttttacggtt cctggccttt tgctggcctt ttgctcacat    60
gttctttcct gcgttatccc ctgattctgt ggataaccgt attaccgcct ttgagtgagc   120
tgataccgct cgccgcagcc gaacgaccga gcgcagcgag tcagtgagcg aggaagcgga   180

```
agagcgccca atacgcaaac cgcctctccc cgcgcgttgg ccgattcatt aatgcagctg    240
gcacgacagg tttcccgact ggaaagcggg cagtgagcgc aacgcaatta atgtgagtta    300
gctcactcat taggcacccc aggctttaca ctttatgctt ccggctcgta tgttgtgtgg    360
aattgtgagc ggataacaat ttcacacagg aaacagctat gaccatgatt acgccaagct    420
tgcatgcctg caggtcgact ctagaggatc cgcaatgcgg atccgcattg cggattacgt    480
attctaatgt tcagtaccgt tcgtataatg tatgctatac gaagttatgc agattgtact    540
gagagtgcac cataccacct tttcaattca tcattttttt tttattcttt tttttgattt    600
cggtttcctt gaattttttt tgattcggta atctccgaac agaaggaaga acgaaggaag    660
gagcacagac ttagattggt atatatacgc atatgtagtg ttgaagaaac atgaaattgc    720
ccagtattct taacccaact gcacagaaca aaaacctgca ggaaacgaag ataaatcatg    780
tcgaaagcta catataagga acgtgctgct actcatccta gtcctgttgc tgccaagcta    840
tttaatatca tgcacgaaaa gcaaacaaac ttgtgtgctt cattggatgt tcgtaccacc    900
aaggaattac tggagttagt tgaagcatta ggtcccaaaa tttgtttact aaaaacacat    960
gtggatatct tgactgattt ttccatggag ggcacagtta agccgctaaa ggcattatcc   1020
gccaagtaca atttttact cttcgaagac agaaaatttg ctgacattgg taatacagtc   1080
aaattgcagt actctgcggg tgtatacaga atagcagaat gggcagacat tacgaatgca   1140
cacggtgtgg tgggcccagg tattgttagc ggtttgaagc aggcggcaga agaagtaaca   1200
aaggaaccta gaggcctttt gatgttagca gaattgtcat gcaagggctc cctatctact   1260
ggagaatata ctaagggtac tgttgacatt gcgaagagcg acaaagattt tgttatcggc   1320
tttattgctc aaagagacat gggtggaaga gatgaaggtt acgattggtt gattatgaca   1380
cccggtgtgg gtttagatga caagggagac gcattgggtc aacagtatag aaccgtggat   1440
gatgtggtct ctacaggatc tgacattatt attgttggaa gaggactatt tgcaaaggga   1500
agggatgcta aggtagaggg tgaacgttac agaaaagcag gctgggaagc atatttgaga   1560
agatgcggcc agcaaaacta aaaaactgta ttataagtaa atgcatgtat actaaactca   1620
caaattagag cttcaattta attatatcag ttattaccct atgcggtgtg aaataccgca   1680
cagatgcgta aggagaaaat accgcatcag gaaattgtaa acgttaatat tttgttaaaa   1740
ttcgcgttaa attttgtta aatcagctca ttttttaacc aataggccga atcggcaaa    1800 atcccttata aatcaaaaga atagaccgag atagggttga gtgttgttcc agtttggaac   1860
aagagtccac tattaaagaa cgtggactcc aacgtcaaag gcgaaaaac cgtctatcag    1920 ggcgatggcc cactacgtga accatcaccc taatcaagat aacttcgtat aatgtatgct   1980
atacgaacgg taccagtgat gatacaacga gttagccaag gtgaattcac tggccgtcgt   2040
tttacaacgt cgtgactggg aaaaccctgg cgttacccaa cttaatcgcc ttgcagcaca   2100
tccccctttc gccagctggc gtaatagcga gaggcccgc accgatcgcc ttcccaaca    2160 gttgcgcagc ctgaatggcg aatggcgcct gatgcggtat tttctcctta cgcatctgtg   2220
cggtatttca caccgcatat ggtgcactct cagtacaatc tgctctgatg ccgcatagtt   2280
aagccagccc cgacacccgc caacacccgc tgacgcgccc tgacgggctt gtctgctccc   2340
ggcatccgct tacagacaag ctgtgaccgt ctccgggagc tgcatgtgtc agaggttttc   2400
accgtcatca ccgaaacgcg cgagacgaaa gggcctcgtg atacgcctat ttttataggt   2460
taatgtcatg ataataatgg tttcttagac gtcaggtggc acttttcggg gaaatgtgcg   2520
```

```
cggaacccct atttgtttat ttttctaaat acattcaaat atgtatccgc tcatgagaca    2580
ataaccctga taaatgcttc aataatattg aaaaaggaag agtatgagta ttcaacattt    2640
ccgtgtcgcc cttattccct ttttgcggc attttgcctt cctgttttg ctcacccaga    2700 aacgctggtg aaagtaaaag atgctgaaga tcagttgggt gcacgagtgg gttacatcga    2760
actggatctc aacagcggta agatccttga gagttttcgc cccgaagaac gttttccaat    2820
gatgagcact tttaaagttc tgctatgtgg cgcggtatta tcccgtattg acgccgggca    2880
agagcaactc ggtcgccgca tacactattc tcagaatgac ttggttgagt actcaccagt    2940
cacagaaaag catcttacgg atggcatgac agtaagagaa ttatgcagtg ctgccataac    3000
catgagtgat aacactgcgg ccaacttact tctgacaacg atcggaggac cgaaggagct    3060
aaccgctttt ttgcacaaca tgggggatca tgtaactcgc cttgatcgtt gggaaccgga    3120
gctgaatgaa gccataccaa acgacgagcg tgacaccacg atgcctgtag caatggcaac    3180
aacgttgcgc aaactattaa ctggcgaact acttactcta gcttcccggc aacaattaat    3240
agactggatg gaggcggata agttgcagg accacttctg cgctcggccc ttccggctgg    3300
ctggtttatt gctgataaat ctggagccgg tgagcgtggg tctcgcggta tcattgcagc    3360
actggggcca gatggtaagc cctcccgtat cgtagttatc tacacgacgg ggagtcaggc    3420
aactatggat gaacgaaata gacagatcgc tgagataggt gcctcactga ttaagcattg    3480
gtaactgtca gaccaagttt actcatatat actttagatt gatttaaaac ttcatttta    3540 atttaaaagg atctaggtga agatccttt tgataatctc atgaccaaaa tcccttaacg    3600
tgagttttcg ttccactgag cgtcagaccc cgtagaaaag atcaaggat cttcttgaga    3660 tcctttttt ctgcgcgtaa tctgctgctt gcaaacaaaa aaaccaccgc taccagcggt    3720
ggtttgtttg ccggatcaag agctaccaac tctttttccg aaggtaactg gcttcagcag    3780
agcgcagata ccaaatactg tccttctagt gtagccgtag ttaggccacc acttcaagaa    3840
ctctgtagca ccgcctacat acctcgctct gctaatcctg ttaccagtgg ctgctgccag    3900
tggcgataag tcgtgtctta ccgggttgga ctcaagacga tagttaccgg ataaggcgca    3960
gcggtcgggc tgaacggggg gttcgtgcac acagcccagc ttggagcgaa cgacctacac    4020
cgaactgaga tacctacagc gtgagctatg agaaagcgcc acgcttcccg aagggagaaa    4080
ggcggacagg tatccggtaa gcggcagggt cggaacagga gagcgcacga gggagcttcc    4140
agggggaaac gcctggtatc tttatagtcc tgtcgggttt cgccacctct gacttgagcg    4200
tcgatttttg tgatgctcgt caggggggcg gagcctatgg aa                      4242
```

<210> SEQ ID NO 22
<211> LENGTH: 80
<212> TYPE: DNA
<213> ORGANISM: Artificial Sequence
<220> FEATURE:
<223> OTHER INFORMATION: LA678

<400> SEQUENCE: 22

```
caacgttaac accgttttcg gtttgccagg tgacttcaac ttgtccttgt gcattgcgga    60
ttacgtattc taatgttcag                                                80
```

<210> SEQ ID NO 23
<211> LENGTH: 81
<212> TYPE: DNA
<213> ORGANISM: Artificial Sequence
<220> FEATURE:
<223> OTHER INFORMATION: LA679

<400> SEQUENCE: 23
gtggagcatc gaagactggc aacatgattt caatcattct gatcttagag caccttggct    60
aactcgttgt atcatcactg g    81

<210> SEQ ID NO 24
<211> LENGTH: 23
<212> TYPE: DNA
<213> ORGANISM: Artificial Sequence
<220> FEATURE:
<223> OTHER INFORMATION: LA337

<400> SEQUENCE: 24
ctcatttgaa tcagcttatg gtg    23

<210> SEQ ID NO 25
<211> LENGTH: 24
<212> TYPE: DNA
<213> ORGANISM: Artificial Sequence
<220> FEATURE:
<223> OTHER INFORMATION: LA692

<400> SEQUENCE: 25
ggaagtcatt gacaccatct tggc    24

<210> SEQ ID NO 26
<211> LENGTH: 24
<212> TYPE: DNA
<213> ORGANISM: Artificial Sequence
<220> FEATURE:
<223> OTHER INFORMATION: LA693

<400> SEQUENCE: 26
agaagctggg acagcagcgt tagc    24

<210> SEQ ID NO 27
<211> LENGTH: 7523
<212> TYPE: DNA
<213> ORGANISM: Artificial Sequence
<220> FEATURE:
<223> OTHER INFORMATION: pLA34

<400> SEQUENCE: 27
ccagcttttg ttcccttttag tgagggttaa ttgcgcgctt ggcgtaatca tggtcatagc    60
tgtttcctgt gtgaaattgt tatccgctca caattccaca caacatagga gccggaagca   120
taaagtgtaa agcctggggt gcctaatgag tgaggtaact cacattaatt gcgttgcgct   180
cactgcccgc tttccagtcg ggaaacctgt cgtgccagct gcattaatga atcggccaac   240
gcgcggggag aggcggtttg cgtattgggc gctcttccgc ttcctcgctc actgactcgc   300
tgcgctcggt cgttcggctg cggcgagcgg tatcagctca ctcaaaggcg gtaatacggt   360
tatccacaga atcaggggat aacgcaggaa agaacatgtg agcaaaaggc cagcaaaagg   420
ccaggaaccg taaaaaggcc gcgttgctgg cgttttttcca taggctccgc cccctgacg   480 agcatcacaa aaatcgacgc tcaagtcaga ggtggcgaaa cccgacagga ctataaagat   540
accaggcgtt tccccctgga agctccctcg tgcgctctcc tgttccgacc ctgccgctta   600
ccggatacct gtccgccttt ctcccttcgg gaagcgtggc gctttctcat agctcacgct   660
gtaggtatct cagttcggtg taggtcgttc gctccaagct gggctgtgtg cacgaacccc   720
ccgttcagcc cgaccgctgc gccttatccg gtaactatcg tcttgagtcc aacccggtaa   780

```
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggttttt tgtttgcaag cagcagatta    1020
cgcgcagaaa aaaggatctc aagaagatcc tttgatcttt tctacggggt ctgacgctc    1080 agtggaacga aaactcacgt taagggattt tggtcatgag attatcaaaa aggatcttca    1140
cctagatcct tttaaattaa aaatgaagtt ttaaatcaat ctaaagtata tatgagtaaa    1200
cttggtctga cagttaccaa tgcttaatca gtgaggcacc tatctcagcg atctgtctat    1260
ttcgttcatc catagttgcc tgactccccg tcgtgtagat aactacgata cgggagggct    1320
taccatctgg ccccagtgct gcaatgatac cgcgagaccc acgctcaccg gctccagatt    1380
tatcagcaat aaaccagcca gccggaaggg ccgagcgcag aagtggtcct gcaactttat    1440
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg cattttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta atgcagtc tcttgataac    2580 ttttgcact gtaggtccgt taaggttaga agaaggctac tttggtgtct attttctctt    2640
ccataaaaaa agcctgactc acttcccgc gtttactgat tactagcgaa gctgcgggtg    2700 catttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacatttc gtattgtttt    2880 cgattcactc tatgaatagt tcttactaca attttttgt ctaaagagta atactagaga    2940
taaacataaa aaatgtagag gtcgagttta gatgcaagtt caaggagcga aaggtggatg    3000
ggtaggttat atagggatat agcacagaga tatatagcaa agagatactt ttgagcaatg    3060
tttgtggaag cggtattcgc aatatttag tagctcgtta cagtccggtg cgttttggt    3120 tttttgaaag tgcgtcttca gagcgctttt ggttttcaaa agcgctctga agttcctata    3180
```

```
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactacccct tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tctttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt tttctttttg cttttctttt tttttctct tgaactcgac   4980 ggatctatgc ggtgtgaaat accgcacaga tgcgtaagga gaaataccg catcaggaaa   5040 ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcacctaat   5280 caagttttt ggggtcgagg tgccgtaaag cactaaatcg gaaccctaaa gggagccccc   5340
gatttagagc ttgacgggga agccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
```

```
actgttggga agggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg ggtaccgggc    5700
cccccctcga ggtattagaa gccgccgagc gggcgacagc cctccgacgg aagactctcc    5760
tccgtgcgtc ctcgtcttca ccggtcgcgt tcctgaaacg cagatgtgcc tcgcgccgca    5820
ctgctccgaa caataaagat tctacaatac tagcttttat ggttatgaag aggaaaaatt    5880
ggcagtaacc tggccccaca aaccttcaaa ttaacgaatc aaattaacaa ccataggatg    5940
ataatgcgat tagtttttta gccttatttc tggggtaatt aatcagcgaa gcgatgattt    6000
ttgatctatt aacagatata taatggaaaa agctgcataa ccactttaac taatactttc    6060
aacattttca gtttgtatta cttcttattc aaatgtcata aaagtatcaa caaaaaattg    6120
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcataccc tggaaaatgct tctgtccgtt    6300
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaacgt tgatgccggt    6540
gaacgtgcaa acaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta aatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
tttttaaagtg actcttaggt tttaaaacga aaattcttat tcttgagtaa ctctttcctg    7320
taggtcaggt tgctttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                             7523

<210> SEQ ID NO 28
<211> LENGTH: 96
<212> TYPE: DNA
<213> ORGANISM: Artificial Sequence
<220> FEATURE:
<223> OTHER INFORMATION: LA722

<400> SEQUENCE: 28
tgccaattat ttacctaaac atctataacc ttcaaaagta aaaaaataca caaacgttga      60
```

```
atcatcacct tggctaactc gttgtatcat cactgg                                    96
```

<210> SEQ ID NO 29
<211> LENGTH: 80
<212> TYPE: DNA
<213> ORGANISM: Artificial Sequence
<220> FEATURE:
<223> OTHER INFORMATION: LA733

<400> SEQUENCE: 29

```
cataatcaat ctcaaagaga acaacacaat acaataacaa gaagaacaaa gcattgcgga         60
ttacgtattc taatgttcag                                                     80
```

<210> SEQ ID NO 30
<211> LENGTH: 30
<212> TYPE: DNA
<213> ORGANISM: Artificial Sequence
<220> FEATURE:
<223> OTHER INFORMATION: LA453

<400> SEQUENCE: 30

```
caccgaagaa gaatgcaaaa atttcagctc                                          30
```

<210> SEQ ID NO 31
<211> LENGTH: 25
<212> TYPE: DNA
<213> ORGANISM: Artificial Sequence
<220> FEATURE:
<223> OTHER INFORMATION: LA694

<400> SEQUENCE: 31

```
gctgaagttg ttagaactgt tgttg                                               25
```

<210> SEQ ID NO 32
<211> LENGTH: 21
<212> TYPE: DNA
<213> ORGANISM: Artificial Sequence
<220> FEATURE:
<223> OTHER INFORMATION: LA695

<400> SEQUENCE: 32

```
tgttagctgg agtagacttg g                                                   21
```

<210> SEQ ID NO 33
<211> LENGTH: 22
<212> TYPE: DNA
<213> ORGANISM: Artificial Sequence
<220> FEATURE:
<223> OTHER INFORMATION: oBP594

<400> SEQUENCE: 33

```
agctgtctcg tgttgtgggt tt                                                  22
```

<210> SEQ ID NO 34
<211> LENGTH: 49
<212> TYPE: DNA
<213> ORGANISM: Artificial Sequence
<220> FEATURE:
<223> OTHER INFORMATION: oBP595

<400> SEQUENCE: 34

```
cttaataata gaacaatatc atcctttacg ggcatcttat agtgtcgtt                     49
```

<210> SEQ ID NO 35

-continued

<211> LENGTH: 49
<212> TYPE: DNA
<213> ORGANISM: Artificial Sequence
<220> FEATURE:
<223> OTHER INFORMATION: oBP596

<400> SEQUENCE: 35
gcgccaacga cactataaga tgcccgtaaa ggatgatatt gttctatta          49

<210> SEQ ID NO 36
<211> LENGTH: 49
<212> TYPE: DNA
<213> ORGANISM: Artificial Sequence
<220> FEATURE:
<223> OTHER INFORMATION: oBP597

<400> SEQUENCE: 36
tatggaccct gaaaccacag ccacattgca acgacgacaa tgccaaacc          49

<210> SEQ ID NO 37
<211> LENGTH: 49
<212> TYPE: DNA
<213> ORGANISM: Artificial Sequence
<220> FEATURE:
<223> OTHER INFORMATION: oBP598

<400> SEQUENCE: 37
tccttggttt ggcattgtcg tcgttgcaat gtggctgtgg tttcagggt          49

<210> SEQ ID NO 38
<211> LENGTH: 49
<212> TYPE: DNA
<213> ORGANISM: Artificial Sequence
<220> FEATURE:
<223> OTHER INFORMATION: oBP599

<400> SEQUENCE: 38
atcctctcgc ggagtccctg ttcagtaaag gccatgaagc ttttcttt          49

<210> SEQ ID NO 39
<211> LENGTH: 49
<212> TYPE: DNA
<213> ORGANISM: Artificial Sequence
<220> FEATURE:
<223> OTHER INFORMATION: oBP600

<400> SEQUENCE: 39
attggaaaga aaagcttca tggcctttac tgaacaggga ctccgcgag          49

<210> SEQ ID NO 40
<211> LENGTH: 22
<212> TYPE: DNA
<213> ORGANISM: Artificial Sequence
<220> FEATURE:
<223> OTHER INFORMATION: oBP601

<400> SEQUENCE: 40
tcataccaca atcttagacc at                                       22

<210> SEQ ID NO 41
<211> LENGTH: 21
<212> TYPE: DNA
<213> ORGANISM: Artificial Sequence
<220> FEATURE:
<223> OTHER INFORMATION: oBP602

<400> SEQUENCE: 41
tgttcaaacc cctaaccaac c                                          21

<210> SEQ ID NO 42
<211> LENGTH: 22
<212> TYPE: DNA
<213> ORGANISM: Artificial Sequence
<220> FEATURE:
<223> OTHER INFORMATION: oBP603

<400> SEQUENCE: 42
tgttcccaca atctattacc ta                                         22

<210> SEQ ID NO 43
<211> LENGTH: 31
<212> TYPE: DNA
<213> ORGANISM: Artificial Sequence
<220> FEATURE:
<223> OTHER INFORMATION: LA811

<400> SEQUENCE: 43
aacgaagcat ctgtgcttca ttttgtagaa c                               31

<210> SEQ ID NO 44
<211> LENGTH: 59
<212> TYPE: DNA
<213> ORGANISM: Artificial Sequence
<220> FEATURE:
<223> OTHER INFORMATION: LA817

<400> SEQUENCE: 44
cgatccactt gtatatttgg atgaattttt gaggaattct gaaccagtcc taaaacgag   59

<210> SEQ ID NO 45
<211> LENGTH: 31
<212> TYPE: DNA
<213> ORGANISM: Artificial Sequence
<220> FEATURE:
<223> OTHER INFORMATION: LA812

<400> SEQUENCE: 45
aacaaagata tgctattgaa gtgcaagatg g                               31

<210> SEQ ID NO 46
<211> LENGTH: 33
<212> TYPE: DNA
<213> ORGANISM: Artificial Sequence
<220> FEATURE:
<223> OTHER INFORMATION: LA818

<400> SEQUENCE: 46
ctcaaaaatt catccaaata tacaagtgga tcg                             33

<210> SEQ ID NO 47
<211> LENGTH: 90
<212> TYPE: DNA
<213> ORGANISM: Artificial Sequence
<220> FEATURE:
<223> OTHER INFORMATION: LA512

<400> SEQUENCE: 47 gtatttggt agattcaatt ctctttccct ttccttttcc ttcgctcccc ttccttatca   60
gcattgcgga ttacgtattc taatgttcag                                 90

<210> SEQ ID NO 48

```
<211> LENGTH: 90
<212> TYPE: DNA
<213> ORGANISM: Artificial Sequence
<220> FEATURE:
<223> OTHER INFORMATION: LA513

<400> SEQUENCE: 48
ttggttgggg gaaaaagagg caacaggaaa gatcagaggg ggaggggggg ggagagtgtc      60
accttggcta actcgttgta tcatcactgg                                      90

<210> SEQ ID NO 49
<211> LENGTH: 29
<212> TYPE: DNA
<213> ORGANISM: Artificial Sequence
<220> FEATURE:
<223> OTHER INFORMATION: LA516

<400> SEQUENCE: 49
ctcgaaacaa taagacgacg atggctctg                                       29

<210> SEQ ID NO 50
<211> LENGTH: 30
<212> TYPE: DNA
<213> ORGANISM: Artificial Sequence
<220> FEATURE:
<223> OTHER INFORMATION: LA514

<400> SEQUENCE: 50
cactatctgg tgcaaacttg gcaccggaag                                      30

<210> SEQ ID NO 51
<211> LENGTH: 29
<212> TYPE: DNA
<213> ORGANISM: Artificial Sequence
<220> FEATURE:
<223> OTHER INFORMATION: LA515

<400> SEQUENCE: 51
tgtttgtagc cactcgtgaa cttctctgc                                       29

<210> SEQ ID NO 52
<211> LENGTH: 6903
<212> TYPE: DNA
<213> ORGANISM: Artificial Sequence
<220> FEATURE:
<223> OTHER INFORMATION: pLA71

<400> SEQUENCE: 52
aaacgccagc aacgcggcct ttttacggtt cctggccttt tgctggcctt ttgctcacat     60
gttctttcct gcgttatccc ctgattctgt ggataaccgt attaccgcct ttgagtgagc    120
tgataccgct cgccgcagcc gaacgaccga gcgcagcgag tcagtgagcg aggaagcgga    180
agagcgccca atacgcaaac cgcctctccc cgcgcgttgg ccgattcatt aatgcagctg    240
gcacgacagg tttcccgact ggaaagcggg cagtgagcgc aacgcaatta atgtgagtta    300
gctcactcat taggcacccc aggctttaca ctttatgctt ccggctcgta tgttgtgtgg    360
aattgtgagc ggataacaat ttcacacagg aaacagctat gaccatgatt acgccaagct    420
tgcatgcgat ctgaaatgaa taacaatact gacagtagat ctgaaatgaa taacaatact    480
gacagtacta ataattgcc tacttggctt cacatacgtt gcatacgtcg atatagataa     540
taatgataat gacagcagga ttatcgtaat acgtaatagt tgaaaatctc aaaaatgtgt    600
gggtcattac gtaaataatg ataggaatgg gattcttcta tttttccttt tccattcta     660
```

```
gcagccgtcg ggaaaacgtg gcatcctctc tttcgggctc aattggagtc acgctgccgt    720
gagcatcctc tctttccata tctaacaact gagcacgtaa ccaatggaaa agcatgagct    780
tagcgttgct ccaaaaaagt attggatggt taataccatt tgtctgttct cttctgactt    840
tgactcctca aaaaaaaaaa atctacaatc aacagatcgc ttcaattacg ccctcacaaa    900
aacttttttc cttcttcttc gcccacgtta aattttatcc ctcatgttgt ctaacggatt    960
tctgcacttg atttattata aaagacaaa gacataatac ttctctatca atttcagtta    1020
ttgttcttcc ttgcgttatt cttctgttct tcttttcctt ttgtcatata taaccataac    1080
caagtaatac atattcaaat ctagagctga ggatgttgac aaaagcaaca aaagaacaaa    1140
aatcccttgt gaaaaacaga ggggcggagc ttgttgttga ttgcttagtg gagcaaggtg    1200
tcacacatgt atttggcatt ccaggtgcaa aaattgatgc ggtatttgac gctttacaag    1260
ataaaggacc tgaaattatc gttgcccggc acgaacaaaa cgcagcattc atggcccaag    1320
cagtcggccg tttaactgga aaaccgggag tcgtgttagt cacatcagga ccgggtgcct    1380
ctaacttggc aacaggcctg ctgacagcga acactgaagg agaccctgtc gttgcgcttg    1440
ctggaaacgt gatccgtgca gatcgtttaa acggacaca tcaatctttg gataatgcgg    1500
cgctattcca gccgattaca aaatacagtg tagaagttca agatgtaaaa aatataccgg    1560
aagctgttac aaatgcattt aggatagcgt cagcagggca ggctggggcc gcttttgtga    1620
gctttccgca agatgttgtg aatgaagtca caaatacgaa aaacgtgcgt gctgttgcag    1680
cgccaaaact cggtcctgca gcagatgatg caatcagtgc ggccatagca aaaatccaaa    1740
cagcaaaact tcctgtcgtt ttggtcggca tgaaaggcgg aagaccggaa gcaattaaag    1800
cggttcgcaa gcttttgaaa aaggttcagc ttccatttgt tgaaacatat caagctgccg    1860 gtacccttc tagagattta gaggatcaat attttggccg tatcggtttg ttccgcaacc    1920
agcctggcga tttactgcta gagcaggcag atgttgttct gacgatcggc tatgacccga    1980
ttgaatatga tccgaaattc tggaatatca atggagaccg gacaattatc catttagacg    2040
agattatcgc tgacattgat catgcttacc agcctgatct tgaattgatc ggtgacattc    2100
cgtccacgat caatcatatc gaacacgatg ctgtgaaagt ggaatttgca gagcgtgagc    2160
agaaaatcct ttctgattta aaacaatata tgcatgaagg tgagcaggtg cctgcagatt    2220
ggaaatcaga cagagcgcac cctcttgaaa tcgttaaaga gttgcgtaat gcagtcgatg    2280
atcatgttac agtaacttgc gatatcggtt cgcacgccat ttggatgtca cgttatttcc    2340
gcagctacga gccgttaaca ttaatgatca gtaacggtat gcaaacactc ggcgttgcgc    2400
ttccttgggc aatcggcgct tcattggtga accgggaga aaagtggtt tctgtctctg    2460 gtgacggcgg tttcttattc tcagcaatgg aattagagac agcagttcga ctaaaagcac    2520
caattgtaca cattgtatgg aacgacagca catatgacat ggttgcattc cagcaattga    2580
aaaaatataa ccgtacatct gcggtcgatt tcggaaatat cgatatcgtg aaatatgcgg    2640
aaagcttcgg agcaactggc ttgcgcgtag aatcaccaga ccagctggca gatgttctgc    2700
gtcaaggcat gaacgctgaa ggtcctgtca tcatcgatgt cccggttgac tacagtgata    2760
acattaattt agcaagtgac aagcttccga agaattcgg ggaactcatg aaaacgaaag    2820
ctctctagtt aattaatcat gtaattagtt atgtcacgct tacattcacg ccctccccc     2880 acatccgctc taaccgaaaa ggaaggagtt agacaacctg aagtctaggt ccctatttat    2940 tttttatag ttatgttagt attaagaacg ttatttatat ttcaaatttt tctttttttt    3000
```

```
ctgtacagac gcgtgtacgc atgtaacatt atactgaaaa ccttgcttga gaaggttttg      3060
ggacgctcga aggctttaat ttaggttttg ggacgctcga aggctttaat ttggatccgc      3120
attgcggatt acgtattcta atgttcagta ccgttcgtat aatgtatgct atacgaagtt      3180
atgcagattg tactgagagt gcaccatacc acagcttttc aattcaattc atcatttttt      3240
ttttattctt ttttttgatt tcggtttctt tgaaattttt ttgattcggt aatctccgaa      3300
cagaaggaag aacgaaggaa ggagcacaga cttagattgg tatatatacg catatgtagt      3360
gttgaagaaa catgaaattg cccagtattc ttaacccaac tgcacagaac aaaaacctgc      3420
aggaaacgaa gataaatcat gtcgaaagct acatataagg aacgtgctgc tactcatcct      3480
agtcctgttg ctgccaagct atttaatatc atgcacgaaa agcaaacaaa cttgtgtgct      3540
tcattggatg ttcgtaccac caaggaatta ctggagttag ttgaagcatt aggtcccaaa      3600
atttgtttac taaaaacaca tgtggatatc ttgactgatt tttccatgga gggcacagtt      3660
aagccgctaa aggcattatc cgccaagtac aatttttttac tcttcgaaga cagaaaattt      3720
gctgacattg gtaatacagt caaattgcag tactctgcgg gtgtatacag aatagcagaa      3780
tgggcagaca ttacgaatgc acacggtgtg gtgggcccag gtattgttag cggtttgaag      3840
caggcggcag aagaagtaac aaaggaacct agaggccttt tgatgttagc agaattgtca      3900
tgcaagggct ccctatctac tggagaatat actaagggta ctgttgacat tgcgaagagc      3960
gacaaagatt ttgttatcgg ctttattgct caaagagaca tgggtggaag agatgaaggt      4020
tacgattggt tgattatgac acccggtgtg ggtttagatg acaagggaga cgcattgggt      4080
caacagtata gaaccgtgga tgatgtggtc tctacaggat ctgacattat tattgttgga      4140
agaggactat ttgcaaaggg aagggatgct aaggtagagg gtgaacgtta cagaaaagca      4200
ggctgggaag catatttgag aagatgcggc cagcaaaact aaaaaactgt attataagta      4260
aatgcatgta tactaaactc acaaattaga gcttcaattt aattatatca gttattaccc      4320
tatgcggtgt gaaataccgc acagatgcgt aaggagaaaa taccgcatca ggaaattgta      4380
aacgttaata ttttgttaaa attcgcgtta aattttgtt aaatcagctc attttttaac       4440
caataggccg aaatcggcaa aatcccttat aaatcaaaag aatagaccga gatagggttg      4500
agtgttgttc cagtttggaa caagagtcca ctattaaaga acgtggactc caacgtcaaa      4560
gggcgaaaaa ccgtctatca gggcgatggc ccactacgtg aaccatcacc ctaatcaaga      4620
taacttcgta atgtatgc tatacgaacg gtaccagtga tgatacaacg agttagccaa       4680
ggtgaattca ctggccgtcg ttttacaacg tcgtgactgg gaaaaccctg gcgttaccca     4740
acttaatcgc cttgcagcac atccccctttt cgccagctgg cgtaatagcg aagaggcccg     4800
caccgatcgc ccttcccaac agttgcgcag cctgaatggc gaatggcgcc tgatgcggta     4860
ttttctcctt acgcatctgt gcggtatttc acaccgcata tggtgcactc tcagtacaat     4920
ctgctctgat gccgcatagt taagccagcc ccgacacccg ccaacacccg ctgacgcgcc     4980
ctgacgggct tgtctgctcc cggcatccgc ttacagacaa gctgtgaccg tctccgggag     5040
ctgcatgtgt cagaggtttt caccgtcatc accgaaacgc gcgagacgaa agggcctcgt     5100
gatacgccta ttttataggt taatgtcat gataataatg gtttcttaga cgtcaggtgg      5160
cacttttcgg ggaaatgtgc gcggaacccc tatttgttta ttttttctaaa tacattcaaa    5220 tatgtatccg ctcatgagac aataaccctg ataaatgctt caataatatt gaaaaggaa     5280 gagtatgagt attcaacatt tccgtgtcgc ccttattccc ttttttgcgg cattttgcct     5340
tcctgttttt gctcacccag aaacgctggt gaaagtaaaa gatgctgaag atcagttggg     5400
```

```
tgcacgagtg ggttacatcg aactggatct caacagcggt aagatccttg agagttttcg    5460 cccccgaagaa cgtttttccaa tgatgagcac ttttaaagtt ctgctatgtg gcgcggtatt   5520
atcccgtatt gacgccgggc aagagcaact cggtcgccgc atacactatt ctcagaatga    5580
cttggttgag tactcaccag tcacagaaaa gcatcttacg gatggcatga cagtaagaga    5640
attatgcagt gctgccataa ccatgagtga taacactgcg gccaacttac ttctgacaac    5700
gatcggagga ccgaaggagc taaccgcttt tttgcacaac atgggggatc atgtaactcg    5760
ccttgatcgt tgggaaccgg agctgaatga agccatacca aacgacgagc gtgacaccac    5820
gatgcctgta gcaatggcaa caacgttgcg caaactatta actggcgaac tacttactct    5880
agcttcccgg caacaattaa tagactggat ggaggcggat aaagttgcag gaccacttct    5940
gcgctcggcc cttccggctg gctggtttat tgctgataaa tctggagccg gtgagcgtgg    6000
gtctcgcggt atcattgcag cactggggcc agatggtaag ccctcccgta tcgtagttat    6060
ctacacgacg gggagtcagg caactatgga tgaacgaaat agacagatcg ctgagatagg    6120
tgcctcactg attaagcatt ggtaactgtc agaccaagtt tactcatata ctttttagat    6180
tgatttaaaa cttcattttt aatttaaaag gatctaggtg aagatccttt ttgataatct    6240
catgaccaaa atcccttaac gtgagttttc gttccactga gcgtcagacc ccgtagaaaa    6300
gatcaaagga tcttcttgag atccttttttt tctgcgcgta atctgctgct tgcaaacaaa    6360
aaaaccaccg ctaccagcgg tggtttgttt gccggatcaa gagctaccaa ctctttttcc    6420
gaaggtaact ggcttcagca gagcgcagat accaaatact gtccttctag tgtagccgta    6480
gttaggccac cacttcaaga actctgtagc accgcctaca tacctcgctc tgctaatcct    6540
gttaccagtg gctgctgcca gtggcgataa gtcgtgtctt accgggttgg actcaagacg    6600
atagttaccg gataaggcgc agcggtcggg ctgaacgggg ggttcgtgca cacagcccag    6660
cttggagcga acgacctaca ccgaactgag atacctacag cgtgagctat gagaaagcgc    6720
cacgcttccc gaagggagaa aggcggacag gtatccggta agcggcaggg tcggaacagg    6780
agagcgcacg agggagcttc caggggggaaa cgcctggtat ctttatagtc ctgtcgggtt    6840
tcgccacctc tgacttgagc gtcgattttt gtgatgctcg tcaggggggc ggagcctatg    6900
gaa                                                                  6903
```

<210> SEQ ID NO 53
<211> LENGTH: 6924
<212> TYPE: DNA
<213> ORGANISM: Artificial Sequence
<220> FEATURE:
<223> OTHER INFORMATION: pLA78

<400> SEQUENCE: 53

```
gatccgcatt gcggattacg tattctaatg ttcagtaccg ttcgtataat gtatgctata      60
cgaagttatg cagattgtac tgagagtgca ccataccacc ttttcaattc atcatttttt     120
ttttattctt tttttttgatt tcggtttcct tgaaattttt ttgattcggt aatctccgaa    180
cagaaggaag aacgaaggaa ggagcacaga cttagattgg tatatatacg catatgtagt    240
gttgaagaaa catgaaattg cccagtattc ttaacccaac tgcacagaac aaaaacctgc    300
aggaaacgaa gataaatcat gtcgaaagct acatataagg aacgtgctgc tactcatcct    360
agtcctgttg ctgccaagct atttaatatc atgcacgaaa agcaaacaaa cttgtgtgct    420
tcattggatg ttcgtaccac caaggaatta ctggagttag ttgaagcatt aggtcccaaa    480
```

```
atttgtttac taaaaacaca tgtggatatc ttgactgatt tttccatgga gggcacagtt      540
aagccgctaa aggcattatc cgccaagtac aattttttac tcttcgaaga cagaaaattt      600
gctgacattg gtaatacagt caaattgcag tactctgcgg gtgtatacag aatagcagaa      660
tgggcagaca ttacgaatgc acacggtgtg gtgggcccag gtattgttag cggttttgaag     720 caggcggcag aagaagtaac aaaggaacct agaggccttt tgatgttagc agaattgtca      780
tgcaagggct ccctatctac tggagaatat actaagggta ctgttgacat tgcgaagagc      840
gacaaagatt ttgttatcgg ctttattgct caaagagaca tgggtggaag agatgaaggt      900
tacgattggt tgattatgac acccggtgtg ggtttagatg acaagggaga cgcattgggt      960
caacagtata gaaccgtgga tgatgtggtc tctacaggat ctgacattat tattgttgga     1020
agaggactat ttgcaaaggg aagggatgct aaggtagagg gtgaacgtta cagaaaagca     1080
ggctgggaag catatttgag aagatgcggc cagcaaaact aaaaaactgt attataagta     1140
aatgcatgta tactaaactc acaaattaga gcttcaattt aattatatca gttattaccc     1200
tatgcggtgt gaaataccgc acagatgcgt aaggagaaaa taccgcatca ggaaattgta     1260
aacgttaata ttttgttaaa attcgcgtta aattttttgtt aaatcagctc attttttaac    1320
caataggccg aaatcggcaa aatcccttat aaatcaaaag aatagaccga gatagggttg     1380
agtgttgttc cagtttggaa caagagtcca ctattaaaga acgtggactc caacgtcaaa     1440
gggcgaaaaa ccgtctatca gggcgatggc ccactacgtg aaccatcacc ctaatcaaga     1500
taacttcgta taatgtatgc tatacgaacg gtaccagtga tgatacaacg agttagccaa     1560
ggtgaattca ctggccgtcg ttttacaacg tcgtgactgg gaaaaccctg gcgttaccca     1620
acttaatcgc cttgcagcac atcccccttt cgccagctgg cgtaatagcg aagaggcccg     1680
caccgatcgc ccttcccaac agttgcgcag cctgaatggc gaatggcgcc tgatgcggta     1740
ttttctcctt acgcatctgt gcggtatttc acaccgcata tggtgcactc tcagtacaat     1800
ctgctctgat gccgcatagt taagccagcc ccgacacccg ccaacacccg ctgacgcgcc     1860
ctgacgggct tgtctgctcc cggcatccgc ttacagacaa gctgtgaccg tctccgggag     1920
ctgcatgtgt cagaggtttt caccgtcatc accgaaacgc gcgagacgaa agggcctcgt     1980
gatacgccta tttttatagg ttaatgtcat gataataatg gtttcttaga cgtcaggtgg     2040
cacttttcgg ggaaatgtgc gcggaacccc tatttgttta tttttctaaa tacattcaaa     2100
tatgtatccg ctcatgagac aataaccctg ataaatgctt caataatatt gaaaaaggaa     2160
gagtatgagt attcaacatt tccgtgtcgc ccttattccc ttttttgcgg cattttgcct     2220
tcctgttttt gctcacccag aaacgctggt gaaagtaaaa gatgctgaag atcagttggg     2280
tgcacgagtg ggttacatcg aactggatct caacagcggt aagatccttg agagttttcg     2340
ccccgaagaa cgttttccaa tgatgagcac ttttaaagtt ctgctatgtg gcgcggtatt     2400
atcccgtatt gacgccgggc aagagcaact cggtcgccgc atacactatt ctcagaatga     2460
cttggttgag tactcaccag tcacagaaaa gcatcttacg gatggcatga cagtaagaga     2520
attatgcagt gctgccataa ccatgagtga taacactgcg gccaacttac ttctgacaac     2580
gatcggagga ccgaaggagc taaccgcttt tttgcacaac atgggggatc atgtaactcg     2640
ccttgatcgt tgggaaccgg agctgaatga agccatacca aacgacgagc gtgacaccac     2700
gatgcctgta gcaatggcaa caacgttgcg caaactatta actggcgaac tacttactct     2760
agcttcccgg caacaattaa tagactggat ggaggcggat aaagttgcag gaccacttct     2820
gcgctcggcc cttccggctg gctggtttat tgctgataaa tctggagccg gtgagcgtgg     2880
```

```
gtctcgcggt atcattgcag cactggggcc agatggtaag ccctcccgta tcgtagttat    2940
ctacacgacg gggagtcagg caactatgga tgaacgaaat agacagatcg ctgagatagg    3000
tgcctcactg attaagcatt ggtaactgtc agaccaagtt tactcatata tactttagat    3060
tgatttaaaa cttcattttt aatttaaaag gatctaggtg aagatccttt ttgataatct    3120
catgaccaaa atcccttaac gtgagttttc gttccactga gcgtcagacc ccgtagaaaa    3180
gatcaaagga tcttcttgag atccttttt tctgcgcgta atctgctgct tgcaaacaaa    3240
aaaaccaccg ctaccagcgg tggtttgttt gccggatcaa gagctaccaa ctcttttcc     3300 gaaggtaact ggcttcagca gagcgcagat accaaatact gtccttctag tgtagccgta    3360
gttaggccac cacttcaaga actctgtagc accgcctaca tacctcgctc tgctaatcct    3420
gttaccagtg gctgctgcca gtggcgataa gtcgtgtctt accgggttgg actcaagacg    3480
atagttaccg gataaggcgc agcggtcggg ctgaacgggg ggttcgtgca cacagcccag    3540
cttggagcga acgacctaca ccgaactgag atacctacag cgtgagctat gagaaagcgc    3600
cacgcttccc gaagggagaa aggcggacag gtatccggta agcggcaggg tcggaacagg    3660
agagcgcacg agggagcttc cagggggaaa cgcctggtat ctttatagtc ctgtcgggtt    3720
tcgccacctc tgacttgagc gtcgattttt gtgatgctcg tcaggggggc ggagcctatg    3780
gaaaaacgcc agcaacgcgg cctttttacg gttcctggcc ttttgctggc cttttgctca    3840
catgttcttt cctgcgttat cccctgattc tgtggataac cgtattaccg cctttgagtg    3900
agctgatacc gctcgccgca gccgaacgac cgagcgcagc gagtcagtga gcgaggaagc    3960
ggaagagcgc ccaatacgca aaccgcctct ccccgcgcgt tggccgattc attaatgcag    4020
ctggcacgac aggtttcccg actggaaagc gggcagtgag cgcaacgcaa ttaatgtgag    4080
ttagctcact cattaggcac cccaggcttt acactttatg cttccggctc gtatgttgtg    4140
tggaattgtg agcggataac aatttcacac aggaaacagc tatgaccatg attacgccaa    4200
gcttccaatt accgtcgctc gtgatttgtt tgcaaaaaga acaaaactga aaaacccag     4260 acacgctcga cttcctgtct tcctattgat tgcagcttcc aatttcgtca cacaacaagg    4320
tcctgtcgac gcctacttgg cttcacatac gttgcatacg tcgatataga taataatgat    4380
aatgacagca ggattatcgt aatacgtaat agttgaaaat ctcaaaaatg tgtgggtcat    4440
tacgtaaata atgataggaa tgggattctt ctatttttcc tttttccatt ctagcagccg    4500
tcgggaaaac gtggcatcct ctctttcggg ctcaattgga gtcacgctgc cgtgagcatc    4560 ctctcttttcc atatctaaca actgagcacg taaccaatgg aaaagcatga gcttagcgtt    4620
gctccaaaaa agtattggat ggttaatacc atttgtctgt tctcttctga ctttgactcc    4680
tcaaaaaaaa aaaatctaca atcaacagat cgcttcaatt acgccctcac aaaaactttt    4740
ttccttcttc ttcgcccacg ttaaatttta tccctcatgt tgtctaacgg atttctgcac    4800
ttgatttatt ataaaaagac aaagacataa tacttctcta tcaatttcag ttattgttct    4860
tccttgcgtt attcttctgt tcttctttt cttttgtcat atataaccat aaccaagtaa    4920
tacatattca agtttaaaca tgtataccgt aggacagtac ttggtagata gactagaaga    4980
gattggtatc gataaggttt tcggtgtgcc aggggattac aatttgactt ttctagatta    5040
cattcaaaat cacgaaggac tttcctggca agggaatact aatgaactaa acgcagcata    5100
tgcagcagat ggctacgccc gtgaaagagg cgtatcagct cttgttacta cattcggagt    5160
gggtgaactg tcagccatta acggaacagc tggtagtttt gcagaacaag tccctgtcat    5220
```

-continued

```
ccacatcgtg ggttctccaa ctatgaatgt gcaatccaac aaaaagctgg ttcatcattc      5280
cttaggaatg ggtaactttc ataactttag tgaaatggct aaggaagtca ctgccgctac      5340
aaccatgctt actgaagaga atgcagcttc agagatcgac agagtattag aaacagcctt      5400
gttggaaaag aggccagtat acatcaatct tccaattgat atagctcata aagcaatagt      5460
taaacctgca aaagcactac aaacagagaa atcatctggt gagagagagg cacaacttgc      5520
agaaatcata ctatcacact tagaaaaggc cgctcaacct atcgtaatcg ccggtcatga      5580
gatcgcccgt ttccagataa gagaaagatt tgaaaactgg ataaaccaaa caaagttgcc      5640
agtaaccaat ttggcatatg gcaaaggctc tttcaatgaa gagaacgaac atttcattgg      5700
tacctattac ccagcttttt ctgacaaaaa cgttctggat tacgttgaca atagtgactt      5760
cgttttacat tttggtggga aaatcattga caattctacc tcctcatttt ctcaaggctt      5820
taagactgaa aacactttaa ccgctgcaaa tgacatcatt atgctgccag atgggtctac      5880
ttactctggg atttctctta acggtctttt ggcagagctg gaaaaactaa actttacttt      5940
tgctgatact gctgctaaac aagctgaatt agctgttttc gaaccacagg ccgaaacacc      6000
actaaagcaa gacagatttc accaagctgt tatgaacttt ttgcaagctg atgatgtgtt      6060
ggtcactgag caggggacat catctttcgg tttgatgttg gcacctctga aaagggtat      6120 gaatttgatc agtcaaacat tatggggctc cataggatac acattacctg ctatgattgg      6180
ttcacaaatt gctgccccag aaaggagaca cattctatcc atcggtgatg gatcttttca      6240
actgacagca caggaaatgt ccaccatctt cagagagaaa ttgacaccag tgatattcat      6300
tatcaataac gatggctata cagtcgaaag agccatccat ggagaggatg agagttacaa      6360
tgatatacca acttggaact tgcaattagt tgctgaaaca tttggtggtg atgccgaaac      6420
tgtcgacact cacaacgttt tcacagaaac agacttcgct aatactttag ctgctatcga      6480
tgctactcct caaaaagcac atgtcgttga agttcatatg gaacaaatgg atatgccaga      6540
atcattgaga cagattggct tagccttatc taagcaaaac tcttaagttt aaactaagcg      6600
aatttcttat gatttatgat ttttattatt aaataagtta taaaaaaaat aagtgtatac      6660
aaattttaaa gtgactctta ggttttaaaa cgaaaattct tattcttgag taactctttc      6720
ctgtaggtca ggttgctttc tcaggtatag catgaggtcg ctcttattga ccacacctct      6780
accggcatgc cgagcaaatg cctgcaaatc gctccccatt tcacccaatt gtagatatgc      6840
taactccagc aatgagttga tgaatctcgg tgtgtatttt atgtcctcag aggacaacac      6900
ctgttgtaat cgttcttcca cacg                                             6924
```

<210> SEQ ID NO 54
<211> LENGTH: 6761
<212> TYPE: DNA
<213> ORGANISM: Artificial Sequence
<220> FEATURE:
<223> OTHER INFORMATION: pLA65

<400> SEQUENCE: 54

```
gatccgcatt gcggattacg tattctaatg ttcagtaccg ttcgtataat gtatgctata       60
cgaagttatg cagattgtac tgagagtgca ccataccacc ttttcaattc atcatttttt      120
ttttattctt ttttttgatt tcggtttcct tgaaattttt ttgattcggt aatctccgaa      180
cagaaggaag aacgaaggaa ggagcacaga cttagattgg tatatatacg catatgtagt      240
gttgaagaaa catgaaattg cccagtattc ttaacccaac tgcacagaac aaaaacctgc      300
aggaaacgaa gataaatcat gtcgaaagct acatataagg aacgtgctgc tactcatcct      360
```

```
agtcctgttg ctgccaagct atttaatatc atgcacgaaa agcaaacaaa cttgtgtgct    420
tcattggatg ttcgtaccac caaggaatta ctggagttag ttgaagcatt aggtcccaaa    480
atttgtttac taaaaacaca tgtggatatc ttgactgatt tttccatgga gggcacagtt    540
aagccgctaa aggcattatc cgccaagtac aattttttac tcttcgaaga cagaaaattt    600
gctgacattg gtaatacagt caaattgcag tactctgcgg gtgtatacag aatagcagaa    660
tgggcagaca ttacgaatgc acacggtgtg gtgggcccag gtattgttag cggtttgaag    720
caggcggcag aagaagtaac aaaggaacct agaggccttt tgatgttagc agaattgtca    780
tgcaagggct ccctatctac tggagaatat actaagggta ctgttgacat tgcgaagagc    840
gacaaagatt ttgttatcgg ctttattgct caaagagaca tgggtggaag agatgaaggt    900
tacgattggt tgattatgac acccggtgtg ggtttagatg acaagggaga cgcattgggt    960
caacagtata gaaccgtgga tgatgtggtc tctacaggat ctgacattat tattgttgga   1020
agaggactat ttgcaaaggg aagggatgct aaggtagagg gtgaacgtta cagaaaagca   1080
ggctgggaag catatttgag aagatgcggc cagcaaaaact aaaaaactgt attataagta   1140
aatgcatgta tactaaactc acaaattaga gcttcaattt aattatatca gttattaccc   1200
tatgcggtgt gaaataccgc acagatgcgt aaggagaaaa taccgcatca ggaaattgta   1260
aacgttaata ttttgttaaa attcgcgtta aattttgtt aaatcagctc attttttaac    1320
caataggccg aaatcggcaa aatcccttat aaatcaaaag aatagaccga datagggttg   1380
agtgttgttc cagtttggaa caagagtcca ctattaaaga acgtggactc caacgtcaaa   1440
gggcgaaaaa ccgtctatca gggcgatggc ccactacgtg aaccatcacc ctaatcaaga   1500
taacttcgta taatgtatgc tatacgaacg gtaccagtga tgatacaacg agttagccaa   1560
ggtgaattca ctggccgtcg ttttacaacg tcgtgactgg gaaaaccctg gcgttaccca   1620
acttaatcgc cttgcagcac atccccctt cgccagctgg cgtaatagcg aagaggcccg    1680
caccgatcgc ccttcccaac agttgcgcag cctgaatggc gaatggcgcc tgatgcggta   1740
ttttctcctt acgcatctgt gcggtatttc acaccgcata tggtgcactc tcagtacaat   1800
ctgctctgat gccgcatagt taagccagcc ccgacacccg ccaacacccg ctgacgcgcc   1860
ctgacgggct tgtctgctcc cggcatccgc ttacagacaa gctgtgaccg tctccgggag   1920
ctgcatgtgt cagaggtttt caccgtcatc accgaaacgc gcgagacgaa agggcctcgt   1980
gatacgccta tttttatagg ttaatgtcat gataataatg gtttcttaga cgtcaggtgg   2040
cacttttcgg ggaaatgtgc gcggaacccc tatttgttta ttttctaaa tacattcaaa    2100 tatgtatccg ctcatgagac aataaccctg ataaatgctt caataatatt gaaaaaggaa   2160
gagtatgagt attcaacatt tccgtgtcgc ccttattccc ttttttgcgg cattttgcct   2220
tcctgttttt gctcacccag aaacgctggt gaaagtaaaa gatgctgaag atcagttggg   2280
tgcacgagtg ggttacatcg aactggatct caacagcggt aagatccttg agagttttcg   2340
ccccgaagaa cgttttccaa tgatgagcac ttttaaagtt ctgctatgtg gcgcggtatt   2400
atcccgtatt gacgccgggc aagagcaact cggtcgccgc atacactatt ctcagaatga   2460
cttggttgag tactcaccag tcacagaaaa gcatcttacg gatggcatga cagtaagaga   2520
attatgcagt gctgccataa ccatgagtga taacactgcg gccaacttac ttctgacaac   2580
gatcggagga ccgaaggagc taaccgcttt tttgcacaac atgggggatc atgtaactcg   2640
ccttgatcgt tgggaaccgg agctgaatga agccatacca aacgacgagc gtgacaccac   2700
```

```
gatgcctgta gcaatggcaa caacgttgcg caaactatta actggcgaac tacttactct   2760
agcttcccgg caacaattaa tagactggat ggaggcggat aaagttgcag gaccacttct   2820
gcgctcggcc cttccggctg gctggtttat tgctgataaa tctggagccg gtgagcgtgg   2880
gtctcgcggt atcattgcag cactggggcc agatggtaag ccctcccgta tcgtagttat   2940
ctacacgacg gggagtcagg caactatgga tgaacgaaat agacagatcg ctgagatagg   3000
tgcctcactg attaagcatt ggtaactgtc agaccaagtt tactcatata ctctttagat   3060
tgatttaaaa cttcattttt aatttaaaag gatctaggtg aagatccttt ttgataatct   3120
catgaccaaa atcccttaac gtgagttttc gttccactga gcgtcagacc ccgtagaaaa   3180
gatcaaagga tcttcttgag atccttttt tctgcgcgta atctgctgct tgcaaacaaa   3240
aaaaccaccg ctaccagcgg tggtttgttt gccggatcaa gagctaccaa ctctttttcc   3300
gaaggtaact ggcttcagca gagcgcagat accaaatact gtccttctag tgtagccgta   3360
gttaggccac cacttcaaga actctgtagc accgcctaca tacctcgctc tgctaatcct   3420
gttaccagtg gctgctgcca gtggcgataa gtcgtgtctt accgggttgg actcaagacg   3480
atagttaccg gataaggcgc agcggtcggg ctgaacgggg ggttcgtgca cacagcccag   3540
cttggagcga acgacctaca ccgaactgag atacctacag cgtgagctat gagaaagcgc   3600
cacgcttccc gaagggagaa aggcggacag gtatccggta agcggcaggg tcggaacagg   3660
agagcgcacg agggagcttc caggggggaaa cgcctggtat ctttatagtc ctgtcgggtt   3720
tcgccacctc tgacttgagc gtcgattttt gtgatgctcg tcagggggc ggagcctatg    3780 gaaaaacgcc agcaacgcgg ccttttttacg gttcctggcc ttttgctggc cttttgctca    3840
catgttcttt cctgcgttat cccctgattc tgtggataac cgtattaccg cctttgagtg    3900
agctgatacc gctcgccgca gccgaacgac cgagcgcagc gagtcagtga gcgaggaagc    3960
ggaagagcgc ccaatacgca aaccgcctct ccccgcgcgt tggccgattc attaatgcag    4020
ctggcacgac aggtttcccg actggaaagc gggcagtgag cgcaacgcaa ttaatgtgag   4080
ttagctcact cattaggcac cccaggcttt acactttatg cttccggctc gtatgttgtg    4140
tggaattgtg agcggataac aatttcacac aggaaacagc tatgaccatg attacgccaa    4200
gcttacctgg taaaacctct agtggagtag tagatgtaat caatgaagcg gaagccaaaa    4260
gaccagagta gaggcctata gaagaaactg cgatacctt tgtgatggct aaacaaacag    4320
acatcttttt atatgttttt acttctgtat atcgtgaagt agtaagtgat aagcgaattt    4380
ggctaagaac gttgtaagtg aacaaggac ctctttttgcc tttcaaaaa ggattaaatg     4440 gagttaatca ttgagattta gttttcgtta gattctgtat ccctaaataa ctcccttacc    4500
cgacgggaag gcacaaaaga cttgaataat agcaaacggc cagtagccaa gaccaaataa    4560
tactagagtt aactgatggt cttaaacagg cattacgtgg tgaactccaa gaccaatata    4620
caaaatatcg ataagttatt cttgcccacc aatttaagga gcctacatca ggacagtagt    4680
accattcctc agagaagagg tatacataac aagaaaatcg cgtgaacacc ttatataact    4740
tagcccgtta ttgagctaaa aaaccttgca aaatttccta tgaataagaa tacttcagac    4800
gtgataaaaa tttactttct aactcttctc acgctgcccc tatctgttct tccgctctac    4860
cgtgagaaat aaagcatcga gtacggcagt tcgctgtcac tgaactaaaa caataaggct    4920
agttcgaatg atgaacttgc ttgctgtcaa acttctgagt tgccgctgat gtgacactgt    4980
gacaataaat tcaaaccggt tatagcggtc tcctccggta ccggttctgc cacctccaat    5040
agagctcagt aggagtcaga acctctgcgg tggctgtcag tgactcatcc gcgtttcgta    5100
```

```
agttgtgcgc gtgcacattt cgcccgttcc cgctcatctt gcagcaggcg gaaattttca    5160
tcacgctgta ggacgcaaaa aaaaaataat taatcgtaca agaatcttgg aaaaaaaatt    5220
gaaaattttt gtataaaagg gatgacctaa cttgactcaa tggcttttac acccagtatt    5280
ttccctttcc ttgtttgtta caattataga agcaagacaa aaacatatag acaacctatt    5340
cctaggagtt atattttttt accctaccag caatataagt aaaaaactgt ttatgaaagc    5400
attagtgtat aggggcccag gccagaagtt ggtggaagag agacagaagc cagagcttaa    5460
ggaacctggt gacgctatag tgaaggtaac aaagactaca atttgcggaa ccgatctaca    5520
cattcttaaa ggtgacgttg cgacttgtaa acccggtcgt gtattagggc atgaaggagt    5580
gggggttatt gaatcagtcg gatctggggt tactgctttc caaccaggcg atagagtttt    5640
gatatcatgt atatcgagtt gcggaaagtg ctcattttgt agaagaggaa tgttcagtca    5700
ctgtacgacc gggggttgga ttctgggcaa cgaaattgat ggtacccaag cagagtacgt    5760
aagagtacca catgctgaca catcccttta tcgtattccg gcaggtgcgg atgaagaggc    5820
cttagtcatg ttatcagata ttctaccaac gggttttgag tgcggagtcc taaacggcaa    5880
agtcgcacct ggttcttcgg tggctatagt aggtgctggt cccgttggtt tggccgcctt    5940
actgacagca caattctact ccccagctga aatcataatg atcgatcttg atgataacag    6000
gctgggatta gccaaacaat ttggtgccac cagaacagta aactccacgg gtggtaacgc    6060
cgcagccgaa gtgaaagctc ttactgaagg cttaggtgtt gatactgcga ttgaagcagt    6120
tgggatacct gctacatttg aattgtgtca gaatatcgta gctcccggtg aactatcgc     6180 taatgtcggc gttcacggta gcaaagttga tttgcatctt gaaagtttat ggtcccataa    6240
tgtcacgatt actacaaggt tggttgacac ggctaccacc ccgatgttac tgaaaactgt    6300
tcaaagtcac aagctagatc catctagatt gataacacat agattcagcc tggaccagat    6360
cttggacgca tatgaaactt ttggccaagc tgcgtctact caagcactaa aagtcatcat    6420
ttcgatggag gcttgattaa ttaagagtaa gcgaatttct tatgatttat gatttttatt    6480
attaaataag ttataaaaaa aataagtgta tacaaatttt aaagtgactc ttaggtttta    6540
aaacgaaaat tcttattctt gagtaactct ttcctgtagg tcaggttgct ttctcaggta    6600
tagcatgagg tcgctcttat tgaccacacc tctaccggca tgccgagcaa atgcctgcaa    6660
atcgctcccc atttcaccca attgtagata tgctaactcc agcaatgagt tgatgaatct    6720
cggtgtgtat tttatgtcct cagaggacaa cacctgtggt g                       6761
```

<210> SEQ ID NO 55
<211> LENGTH: 90
<212> TYPE: DNA
<213> ORGANISM: Artificial Sequence
<220> FEATURE:
<223> OTHER INFORMATION: 895

<400> SEQUENCE: 55

```
tctcaattat tattttctac tcataacctc acgcaaaata acacagtcaa atcaatcaaa    60
atgttgacaa aagcaacaaa agaacaaaaa                                     90
```

<210> SEQ ID NO 56
<211> LENGTH: 81
<212> TYPE: DNA
<213> ORGANISM: Artificial Sequence
<220> FEATURE:
<223> OTHER INFORMATION: 679

<400> SEQUENCE: 56
gtggagcatc gaagactggc aacatgattt caatcattct gatcttagag caccttggct    60
aactcgttgt atcatcactg g    81

<210> SEQ ID NO 57
<211> LENGTH: 20
<212> TYPE: DNA
<213> ORGANISM: Artificial Sequence
<220> FEATURE:
<223> OTHER INFORMATION: 681

<400> SEQUENCE: 57
ttattgctta gcgttggtag    20

<210> SEQ ID NO 58
<211> LENGTH: 22
<212> TYPE: DNA
<213> ORGANISM: Artificial Sequence
<220> FEATURE:
<223> OTHER INFORMATION: 92

<400> SEQUENCE: 58
gagaagatgc ggccagcaaa ac    22

<210> SEQ ID NO 59
<211> LENGTH: 25
<212> TYPE: DNA
<213> ORGANISM: Artificial Sequence
<220> FEATURE:
<223> OTHER INFORMATION: N245

<400> SEQUENCE: 59
agggtagcct ccccataaca taaac    25

<210> SEQ ID NO 60
<211> LENGTH: 25
<212> TYPE: DNA
<213> ORGANISM: Artificial Sequence
<220> FEATURE:
<223> OTHER INFORMATION: N246

<400> SEQUENCE: 60
tctccaaata tacctctt gtgtg    25

<210> SEQ ID NO 61
<211> LENGTH: 90
<212> TYPE: DNA
<213> ORGANISM: Artificial Sequence
<220> FEATURE:
<223> OTHER INFORMATION: 896

<400> SEQUENCE: 61
ttttatatac agtataaata aaaacccac gtaatatagc aaaaacatat tgccaacaaa    60
aattaccgtc gctcgtgatt tgtttgcaaa    90

<210> SEQ ID NO 62
<211> LENGTH: 90
<212> TYPE: DNA
<213> ORGANISM: Artificial Sequence
<220> FEATURE:
<223> OTHER INFORMATION: 897

<400> SEQUENCE: 62
caaactgtgt aagtttattt atttgcaaca ataattcgtt tgagtacact actaatggcc    60

-continued accttggcta actcgttgta tcatcactgg    90

<210> SEQ ID NO 63
<211> LENGTH: 28
<212> TYPE: DNA
<213> ORGANISM: Artificial Sequence
<220> FEATURE:
<223> OTHER INFORMATION: 365

<400> SEQUENCE: 63
ctctatctcc gctcaggcta agcaattg    28

<210> SEQ ID NO 64
<211> LENGTH: 26
<212> TYPE: DNA
<213> ORGANISM: Artificial Sequence
<220> FEATURE:
<223> OTHER INFORMATION: 366

<400> SEQUENCE: 64
cagccgactc aacggcctgt ttcacg    26

<210> SEQ ID NO 65
<211> LENGTH: 28
<212> TYPE: DNA
<213> ORGANISM: Artificial Sequence
<220> FEATURE:
<223> OTHER INFORMATION: N638

<400> SEQUENCE: 65
aaaagatagt gtagtagtga taaactgg    28

<210> SEQ ID NO 66
<211> LENGTH: 22
<212> TYPE: DNA
<213> ORGANISM: Artificial Sequence
<220> FEATURE:
<223> OTHER INFORMATION: 740

<400> SEQUENCE: 66
cgataatcct gctgtcatta tc    22

<210> SEQ ID NO 67
<211> LENGTH: 83
<212> TYPE: DNA
<213> ORGANISM: Artificial Sequence
<220> FEATURE:
<223> OTHER INFORMATION: 856

<400> SEQUENCE: 67
gcttatttag aagtgtcaac aacgtatcta ccaacgattt gacccttttc cacaccttgg    60
ctaactcgtt gtatcatcac tgg    83

<210> SEQ ID NO 68
<211> LENGTH: 80
<212> TYPE: DNA
<213> ORGANISM: Artificial Sequence
<220> FEATURE:
<223> OTHER INFORMATION: 857

<400> SEQUENCE: 68
gcacaatatt tcaagctata ccaagcatac aatcaactat ctcatataca atgaaagcat    60
tagtgtatag gggcccaggc    80

```
<210> SEQ ID NO 69
<211> LENGTH: 25
<212> TYPE: DNA
<213> ORGANISM: Artificial Sequence
<220> FEATURE:
<223> OTHER INFORMATION: BK415

<400> SEQUENCE: 69
gcctcattga tggtggtaca taacg                                              25

<210> SEQ ID NO 70
<211> LENGTH: 26
<212> TYPE: DNA
<213> ORGANISM: Artificial Sequence
<220> FEATURE:
<223> OTHER INFORMATION: N1092

<400> SEQUENCE: 70
agagttttga tatcatgtat atcgag                                             26

<210> SEQ ID NO 71
<211> LENGTH: 92
<212> TYPE: DNA
<213> ORGANISM: Artificial Sequence
<220> FEATURE:
<223> OTHER INFORMATION: 906

<400> SEQUENCE: 71
atgacaggtg aaagaattga aaaggtgaaa ataaatgacg aatttgcaaa atcacatttc        60
acctggtaaa acctctagtg gagtagtaga tg                                      92

<210> SEQ ID NO 72
<211> LENGTH: 87
<212> TYPE: DNA
<213> ORGANISM: Artificial Sequence
<220> FEATURE:
<223> OTHER INFORMATION: 907

<400> SEQUENCE: 72
aaaaagattc aatgccgtct cctttcgaaa cttaataata gaacaatatc atccttcacc        60
ttggctaact cgttgtatca tcactgg                                            87

<210> SEQ ID NO 73
<211> LENGTH: 70
<212> TYPE: DNA
<213> ORGANISM: Artificial Sequence
<220> FEATURE:
<223> OTHER INFORMATION: 667

<400> SEQUENCE: 73
tctcctttcg aaacttaata atagaacaat atcatccttt tgtaaaacga cggccagtga       60
attcaccttg                                                              70

<210> SEQ ID NO 74
<211> LENGTH: 25
<212> TYPE: DNA
<213> ORGANISM: Artificial Sequence
<220> FEATURE:
<223> OTHER INFORMATION: 749

<400> SEQUENCE: 74
caagtctttt gtgccttccc gtcgg                                              25
```

```
<210> SEQ ID NO 75
<211> LENGTH: 25
<212> TYPE: DNA
<213> ORGANISM: Artificial Sequence
<220> FEATURE:
<223> OTHER INFORMATION: 413

<400> SEQUENCE: 75
ggacataaaa tacacaccga gattc                                           25

<210> SEQ ID NO 76
<211> LENGTH: 10934
<212> TYPE: DNA
<213> ORGANISM: Artificial Sequence
<220> FEATURE:
<223> OTHER INFORMATION: pRS423::TEF(M4)-xpk1+ENO1-eutD

<400> SEQUENCE: 76
ggtggagctc cagcttttgt tccctttagt gagggttaat tgcgcgcttg gcgtaatcat       60
ggtcatagct gtttcctgtg tgaaattgtt atccgctcac aattccacac aacataggag      120
ccggaagcat aaagtgtaaa gcctggggtg cctaatgagt gaggtaactc acattaattg      180
cgttgcgctc actgcccgct ttccagtcgg gaaacctgtc gtgccagctg cattaatgaa      240
tcggccaacg cgcggggaga ggcggtttgc gtattgggcg ctcttccgct tcctcgctca      300
ctgactcgct gcgctcggtc gttcggctgc ggcgagcgg atcagctcac tcaaaggcgg       360
taatacggtt atccacagaa tcaggggata acgcaggaaa gaacatgtga gcaaaaggcc      420
agcaaaaggc caggaaccgt aaaaaggccg cgttgctggc gtttttccat aggctccgcc      480
cccctgacga gcatcacaaa aatcgacgct caagtcagag gtggcgaaac ccgacaggac      540
tataaagata ccaggcgttt ccccctggaa gctccctcgt gcgctctcct gttccgaccc      600
tgccgcttac cggatacctg tccgcctttc tcccttcggg aagcgtggcg ctttctcata      660
gctcacgctg taggtatctc agttcggtgt aggtcgttcg ctccaagctg ggctgtgtgc      720
acgaaccccc cgttcagccc gaccgctgcg ccttatccgg taactatcgt cttgagtcca      780
acccggtaag acacgactta tcgccactgg cagcagccac tggtaacagg attagcagag      840
cgaggtatgt aggcggtgct acagagttct tgaagtggtg gcctaactac ggctacacta      900
gaaggacagt atttggtatc tgcgctctgc tgaagccagt taccttcgga aaaagagttg      960
gtagctcttg atccggcaaa caaaccaccg ctggtagcgg tggttttttt gtttgcaagc     1020
agcagattac gcgcagaaaa aaaggatctc aagaagatcc tttgatcttt tctacggggt     1080
ctgacgctca gtggaacgaa aactcacgtt aagggatttt ggtcatgaga ttatcaaaaa     1140
ggatcttcac ctagatcctt ttaaattaaa aatgaagttt taaatcaatc taaagtatat     1200
atgagtaaac ttggtctgac agttaccaat gcttaatcag tgaggcacct atctcagcga     1260
tctgtctatt tcgttcatcc atagttgcct gactccccgt cgtgtagata actacgatac     1320
gggagggctt accatctggc cccagtgctg caatgatacc gcgagaccca cgctcaccgg     1380
ctccagattt atcagcaata aaccagccag ccggaagggc cgagcgcaga agtggtcctg     1440
caactttatc cgcctccatc cagtctatta attgttgccg ggaagctaga gtaagtagtt     1500
cgccagttaa tagtttgcgc aacgttgttg ccattgctac aggcatcgtg gtgtcacgct     1560
cgtcgtttgg tatggcttca ttcagctccg gttcccaacg atcaaggcga gttacatgat     1620
cccccatgtt gtgcaaaaaa gcggttagct ccttcggtcc tccgatcgtt gtcagaagta     1680
agttggccgc agtgttatca ctcatggtta tggcagcact gcataattct cttactgtca     1740
```

```
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040 caaaaaggg aataagggcg cacggaaat gttgaatact catactcttc cttttcaat     2100 attattgaag catttatcag ggttattgtc tcatgagcgg atacatattt gaatgtattt    2160
agaaaaataa acaaataggg gttccgcgca catttccccg aaaagtgcca cctgaacgaa    2220
gcatctgtgc ttcattttgt agaacaaaaa tgcaacgcga gagcgctaat ttttcaaaca    2280
aagaatctga gctgcatttt tacagaacag aaatgcaacg cgaaagcgct attttaccaa    2340
cgaagaatct gtgcttcatt tttgtaaaac aaaaatgcaa cgcgagagcg ctaatttttc    2400
aaacaaagaa tctgagctgc attttacag aacagaaatg caacgcgaga gcgctatttt    2460
accaacaaag aatctatact tcttttttgt tctacaaaaa tgcatcccga gagcgctatt    2520
tttctaacaa agcatcttag attactttt ttctcctttg tgcgctctat aatgcagtct    2580
cttgataact ttttgcactg taggtccgtt aaggttagaa gaaggctact ttggtgtcta    2640
ttttctcttc cataaaaaaa gcctgactcc acttcccgcg tttactgatt actagcgaag    2700
ctgcgggtgc attttttcaa gataaaggca tccccgatta tattctatac cgatgtggat    2760
tgcgcatact tgtgaacag aaagtgatag cgttgatgat tcttcattgg tcagaaaatt    2820
atgaacggtt tcttctattt tgtctctata tactacgtat aggaaatgtt tacattttcg    2880
tattgttttc gattcactct atgaatagtt cttactacaa tttttttgtc taaagagtaa    2940
tactagagat aaacataaaa aatgtagagg tcgagtttag atgcaagttc aaggagcgaa    3000
aggtggatgg gtaggttata tagggatata gcacagagat atatagcaaa gagatacttt    3060
tgagcaatgt ttgtggaagc ggtattcgca atatttagt agctcgttac agtccggtgc    3120 gttttggt ttttgaaagt gcgtcttcag agcgcttttg gttttcaaaa gcgctctgaa    3180
gttcctatac tttctagaga ataggaactt cggaatagga acttcaaagc gtttccgaaa    3240
acgagcgctt ccgaaaatgc aacgcgagct gcgcacatac agctcactgt tcacgtcgca    3300
cctatatctg cgtgttgcct gtatatat atacatgaga agaacggcat agtgcgtgtt    3360
tatgcttaaa tgcgtactta tatgcgtcta tttatgtagg atgaaaggta gtctagtacc    3420
tcctgtgata ttatcccatt ccatgcgggg tatcgtatgc ttccttcagc actacccttt    3480
agctgttcta tatgctgcca ctcctcaatt ggattagtct catccttcaa tgctatcatt    3540
tcctttgata ttggatcatc taagaaacca ttattatcat gacattaacc tataaaaata    3600
ggcgtatcac gaggccctt cgtctcgcgc gtttcggtga tgacggtgaa aacctctgac    3660
acatgcagct cccggagacg gtcacagctt gtctgtaagc ggatgccggg agcagacaag    3720
cccgtcaggg cgcgtcagcg ggtgttggcg ggtgtcgggg ctggcttaac tatgcggcat    3780
cagagcagat tgtactgaga gtgcaccata aattcccgtt ttaagagctt ggtgagcgct    3840
aggagtcact gccaggtatc gtttgaacac ggcattagtc agggaagtca taacacagtc    3900
ctttcccgca atttttcttt tctattactc ttggcctcct ctagtacact ctatatttt     3960 ttatgcctcg gtaatgattt tcatttttt tttccccta gcggatgact cttttttttt    4020
cttagcgatt ggcattatca cataatgaat tatacattat ataaagtaat gtgatttctt    4080
cgaagaatat actaaaaaat gagcaggcaa gataaacgaa ggcaaagatg acagagcaga    4140
```

```
aagccctagt aaagcgtatt acaaatgaaa ccaagattca gattgcgatc tctttaaagg    4200
gtggtcccct agcgatagag cactcgatct tcccagaaaa agaggcagaa gcagtagcag    4260
aacaggccac acaatcgcaa gtgattaacg tccacacagg tatagggttt ctggaccata    4320
tgatacatgc tctggccaag cattccggct ggtcgctaat cgttgagtgc attggtgact    4380
tacacataga cgaccatcac accactgaag actgcgggat tgctctcggt caagctttta    4440
aagaggccct actggcgcgt ggagtaaaaa ggtttggatc aggatttgcg cctttggatg    4500
aggcactttc cagagcggtg gtagatcttt cgaacaggcc gtacgcagtt gtcgaacttg    4560
gtttgcaaag ggagaaagta ggagatctct cttgcgagat gatcccgcat tttcttgaaa    4620
gctttgcaga ggctagcaga attaccctcc acgttgattg tctgcgaggc aagaatgatc    4680
atcaccgtag tgagagtgcg ttcaaggctc ttgcggttgc cataagagaa gccacctcgc    4740
ccaatggtac caacgatgtt ccctccacca aggtgttct tatgtagtga caccgattat    4800
ttaaagctgc agcatacgat atatatacat gtgtatatat gtatacctat gaatgtcagt    4860
aagtatgtat acgaacagta tgatactgaa gatgacaagg taatgcatca ttctatacgt    4920
gtcattctga acgaggcgcg cttttccttt ttcttttttgc tttttctttt tttttctctt    4980
gaactcgacg gatctatgcg gtgtgaaata ccgcacagat gcgtaaggag aaaataccgc    5040
atcaggaaat tgtaaacgtt aatattttgt taaaattcgc gttaaatttt tgttaaatca    5100
gctcattttt taaccaatag gccgaaatcg gcaaaatccc ttataaatca aaagaataga    5160
ccgagatagg gttgagtgtt gttccagttt ggaacaagag tccactatta agaacgtgg     5220
actccaacgt caaagggcga aaaccgtct atcagggcga tggcccacta cgtgaaccat     5280
caccctaatc aagttttttg gggtcgaggt gccgtaaagc actaaatcgg aaccctaaag    5340
ggagcccccg atttagagct tgacggggaa agccggcgaa cgtggcgaga aggaaggga    5400
agaaagcgaa aggagcgggc gctagggcgc tggcaagtgt agcggtcacg ctgcgcgtaa    5460
ccaccacacc cgccgcgctt aatgcgccgc tacagggcgc gtcgcgccat cgccattca    5520
ggctgcgcaa ctgttgggaa gggcgatcgg tgcgggcctc ttcgctatta cgccagctgg    5580
cgaaaggggg atgtgctgca aggcgattaa gttgggtaac gccagggttt cccagtcac    5640
gacgttgtaa aacgacggcc agtgagcgcg cgtaatacga ctcactatag ggcgaattgg    5700
gtaccgggcc cccctcgag gtcgacggta tcgataagct tgatatcgaa ttcctgcgcc    5760
cgggccacta gtcagatgcc gcgggcactt gagcacctca tgcacagcaa taacacaaca    5820
caatggttag tagcaacctg aattcggtca ttgatgcatg catgtgccgt gaagcgggac    5880
aaccagaaaa gtcgtctata aatgccggca cgtgcgatca tcgtggcggg gttttaagag    5940
tgcatatcac aaattgtcgc attaccgcgg aaccgccaga tattcattac ttgacgcaaa    6000
agcgtttgaa ataatgacga aaagaagga agaaaaaaa agaaaaatac cgcttctagg    6060
cgggttatct actgatccga gcttccacta ggatagcacc caaacacctg catatttgga    6120
cgacctttac ttacaccacc aaaaaccact ttcgcctctc ccgcccctga taacgtccac    6180
taattgagcg attacctgag cggtcctctt ttgtttgcag catgagactt gcatactgca    6240
aatcgtaagt agcaacgtct caaggtcaaa actgtatgga aaccttgtca cctcacttaa    6300
ttctagctag cctaccctgc aagtcaagag gtctccgtga ttcctagcca cctcaaggta    6360
tgcctctccc cggaaactgt ggccttttct ggcacacatg atctccacga tttcaacata    6420
taaatagctt ttgataatgg caatattaat caaatttatt ttacttcttt cttgtaacat    6480
```

```
ctctcttgta atcccttatt ccttctagct atttttcata aaaaaccaag caactgctta    6540
tcaacacaca aacactaaat caaagctgag gatggattta tttgagtcat tagcacaaaa    6600
aattactggt aaagatcaaa caattgtttt ccctgaagga actgaacccc gaattgtcgg    6660
tgcggcagcg cgattagctg cagacggctt ggttaagccg attgttttag gtgcaacgga    6720
caaagttcag gctgtggcta acgatttgaa tgcggattta acaggcgttc aagtccttga    6780
tcctgcgaca tacccggctg aagataagca agcaatgctt gatgccctcg ttgaacggcg    6840
gaaaggtaag aatacgccag aacaagcggc taaaatgctg gaagatgaaa actactttgg    6900
cacgatgctc gtttatatgg gcaaagcgga tgggatggtt tcaggtgcaa tccatccaac    6960
tggtgatacg gtacggccag cgttacaaat tattaagacc aagcccggtt cacaccgaat    7020
ctcgggtgca tttatcatgc aaaagggtga ggaacgctac gtctttgctg actgtgccat    7080
caatattgat cccgatgccg atacgttagc ggaaattgcc actcagagtg cggctactgc    7140
taaggtcttc gatattgacc cgaaagttgc gatgctcagc ttctcaacta agggttcggc    7200
taagggtgaa atggtcacta aagtgcaaga agcaacggcc aaggcgcaag ctgctgaacc    7260
ggaattggct atcgatggtg aacttcaatt tgacgcggcc ttcgttgaaa agttggttt    7320 gcaaaaggct cctggttcca aagtagctgg tcatgccaat gtctttgtat ttccagagct    7380
tcagtctggt aatattggct ataagattgc gcaacgattt ggtcattttg aagcggtggg    7440
tcctgtcttg caaggcctga acaagccggt ctccgacttg tcacgtggat gcagtgaaga    7500
agacgtttat aaggttgcga ttattacagc agcccaagga ttagcttaat taattaagag    7560
taagcgaatt tcttatgatt tatgattttt attattaaat aagttataaa aaaataagt    7620 gtatacaaat tttaaagtga ctcttaggtt ttaaaacgaa aattcttatt cttgagtaac    7680
tctttcctgt aggtcaggtt gctttctcag gtatagcatg aggtcgctct tattgaccac    7740
acctctaccg gcatgccgag caaatgcctg caaatcgctc cccatttcac ccaattgtag    7800
atatgctaac tccagcaatg agttgatgaa tctcggtgtg tatttatgt cctcaggaga    7860 caacacctgt ggtactagtt ctagagcggc cgcccgcaaa ttaaagcctt cgagcgtccc    7920
aaaaccttct caagcaaggt tttcagtata atgttacatg cgtacacgcg tttgtacaga    7980 aaaaaagaa aaatttgaaa tataaataac gttcttaata ctaacataac tattaaaaaa    8040
aataaatagg gacctagact tcaggttgtc taactccttc cttttcggtt agagcggatg    8100
tgggaggagg gcgtgaatgt aagcgtgaca taactaatta catgattaat taattatttt    8160
aaacccttcc attgccaatc attaacttct ggcaagtcag ttccggcatc ccggatatag    8220
gcattgtgtt tagcaagcat attatccatg gattgaacga aggccgcacc agtgttttcc    8280
attgctggtt gcgccgcaat tgccgactta gctaagtcga agcggtccat ctggttcatg    8340
acccgtacgt cgaatggtgt ggtaatatca ccattttcac ggtaaccgtg gacgtataag    8400
ttatggttgt gacgatcaaa gaagatgtca cgaactaagt cttcgtaacc gtggaaagca    8460
aagaccactg gtttgtcctt agtaaagtaa tggtcaaact cagcatctga caagcccgc    8520 ggatcctttt caggactacg taacttcaag atgtcgacca cgttcacgaa acgaatcttc    8580
atctctggga actgtcgtg tagtaattgg atggcagcca acgtttcaag cgttggttcc    8640
gtcccagcag ctgcaaagac aatgtctggt tcgctacctt ggtccgtact tgcccaatca    8700
atgataccaa gaccattgtc aactaattgc ttagcttctt caatgctgaa ccattgttga    8760
cgtgggtgtt ttgacgtaac cacgtagttg atctttctt ggctccggaa aatgacgtca    8820
ccgacagcta ataacgtgtt ggcatcggct ggtaaatatt cacgaatgta ttctggtttc    8880
```

```
ttttcggcca aatgagttaa tgcacctgga tcttggtggg tataaccatt atggtcttgt    8940
tggaatacag ttgaagccgc gataatgtta agtgatgggg acttttttacg ccaatcaagt    9000 tcattggctt tacgtaacca cttgaagtgt tgcgtcaaca ttgagtccac aacgcgtagg    9060
aaggcttcat aactggcaaa taacccatga cgtccagtta agacgtaacc ttctaaccaa    9120
ccttcagctt ggtgttcaga taactgagca tctaagaccc ggccagctgg tgcttcatat    9180
tggtcactat ctggatgaat gtcttccatc cattgacgat tagtggtttc gaagacacca    9240
tataaacggt tagacatggt ttcatcaggt ccgaacaacc ggaagttatc aggattttc     9300 ttgatgacat cccgcaaata gtctgaccaa acgatcatat cttgcttaac attcgcgcct    9360
tctttggacg tatcgaccgc ataatcacgg aagtttggta agttcaaggc tttcggatcg    9420
accccaccat tggtgattgg gttagcagcc atccgactgt ccccagtagg aataatttct    9480
ttaatatcat ccttcaaaga gccatcttca ttgaagagtt cttttggttg atatgattcg    9540
agccaatcaa ctaaagcatc cgcatgttcc atgtcatttt gatcaacagg aatcggaatt    9600
tgatgagcac ggaatgaacc ttcgatctta tcaccgtccc atgacttcgg accagtccag    9660
cccttaggtg cgcggaagac gatcattggc catactggca atgttgcatc gttattttcg    9720
cgagcatgct tctggattgc cttgatcttt tcaacggctt catccatggc cttagctaag    9780
gctgggtgaa ccttttcagg atcgtcacct tcaacgaaga ttggttccca attcatgctt    9840
tcgaagtatt ccttaatctt agcatcagaa gtccgaccaa aaatcgttgg attagaaatc    9900
ttaaaaccat ttaagttcaa gattggtaaa acagccccgt cgttgattgg gttaatgaac    9960
ttcgttgatt gccatgaagt tgctaatgga cccgtttcgg attccccatc accaacaaca    10020
accgcggcga tttcgtcagg attgtcaaga attgccccaa ccccgtgtga aattgagtaa    10080
ccaagttcgc caccttcgtg gattgaaccg ggtgtttcag gtgccgcatg ggaagcaacc    10140
ccacctggga atgagaattg cttgaagagc ttttgcatcc cttcaacatc ctgcgtaatt    10200
tctggataaa tatcggtgta agtaccgtca aggtaagagt ttgaaaccat cacttgacca    10260
ccatgacctg gaccttcaac gtagaacatc ttcaaaccgt acttgttgat gacccggtta    10320
agatgagcat agataaagtt ttgaccggca atcgtccccc agtgaccaat ggatgaacc     10380 ttaacgtcac tggccttcaa tggccgttgt aatagtggat tatctttaa ataaagttga     10440 ccaactgata agtagttggc agcacgccag tacttatcaa cttttttgcaa atatgctggt    10500 gatgagtaat ctgttgtcat cctcagctgg aacttagatt agattgctat gctttctctc    10560
taacgagcaa gaagtaaaaa aagttgtaat agaacaagaa aaatgaaact gaagcttgag    10620
aaattgaaga ccgtttatta gcttaaatat caatgggagg tcatcgaaag agaaaaaaat    10680
caagaaagaa actctcaaga aaagaaacg tgataaaaat ttttattgcc tctctcgacg     10740
aagagaaaga aacgaggcgg tccctttttt cttttccaaa cctttagtac gggtaattag    10800
cgacacccta gaggaagaaa gaggggaaat ttagtatgct gtgcttgggt gtcttgaagt    10860
ggtacggcga tgcgcggagt ccgagaaaat ctggaagagt aaaagggggg tagaagcgtt    10920
ttgaagctat ccgc                                                      10934
```

<210> SEQ ID NO 77
<211> LENGTH: 80
<212> TYPE: DNA
<213> ORGANISM: Artificial Sequence
<220> FEATURE:
<223> OTHER INFORMATION: N1341

```
<400> SEQUENCE: 77
gttgcaagaa atgcattatg caattttttg attatgacaa tctctcgaaa atagcttcaa    60
aacgcttcta ccccctttt                                                 80

<210> SEQ ID NO 78
<211> LENGTH: 80
<212> TYPE: DNA
<213> ORGANISM: Artificial Sequence
<220> FEATURE:
<223> OTHER INFORMATION: N1338

<400> SEQUENCE: 78
catacattat acgaacggta ctgaacatta gaatacgtaa tccgcaatgc ccgcaaatta    60
aagccttcga gcgtcccaaa                                                80

<210> SEQ ID NO 79
<211> LENGTH: 30
<212> TYPE: DNA
<213> ORGANISM: Artificial Sequence
<220> FEATURE:
<223> OTHER INFORMATION: N1033c

<400> SEQUENCE: 79
gcattgcgga ttacgtattc taatgttcag                                     30

<210> SEQ ID NO 80
<211> LENGTH: 81
<212> TYPE: DNA
<213> ORGANISM: Artificial Sequence
<220> FEATURE:
<223> OTHER INFORMATION: N1342

<400> SEQUENCE: 80
acatatgtga aaaaaaatag ttgatatttt aaaccaaatc agaaatttat caccttggct    60
aactcgttgt atcatcactg g                                              81

<210> SEQ ID NO 81
<211> LENGTH: 30
<212> TYPE: DNA
<213> ORGANISM: Artificial Sequence
<220> FEATURE:
<223> OTHER INFORMATION: N1364

<400> SEQUENCE: 81
atgacaacag attactcatc accagcatat                                     30

<210> SEQ ID NO 82
<211> LENGTH: 604
<212> TYPE: DNA
<213> ORGANISM: Artificial Sequence
<220> FEATURE:
<223> OTHER INFORMATION: L8

<400> SEQUENCE: 82
gcctacttgg cttcacatac gttgcatacg acgatataga aataatgat aatgacagca     60 ggattatcgt ataacgtaat agtcgaaaaa tctcaaaaat ctgtgggtca ttacgtaaat   120
aatgatagga atgtgattct tctattttc cttttccat tctggcagcc gtcgggaaaa     180
cgtggcttcc tctcttttcgg gctctattgg agtaacgctg ccgtgagctt cctctctttc   240
catatctaac aactgagcac gtaaccaatg gtaaagcatg agcttagcgt tgctccaaag   300
aagtattgga aggttaatac catgtgtctg ttctcttctg actttgactc ctcaaataaa   360
```

```
aaaaaattct acaatcaaca gatcgcttca attacgctct cacaaaaact ttttccttc    420 ttcttcgccc acgttaaatt ttaaccctca tgctgtctaa cggatttctg cacttaattt    480
attataaaac gacaaagaca taatacttct ctatcaattt cagttattgt tcttcattgc    540
attactcttc tgttcttctt tttcatttgt catatacaac cataaccaaa taatacatat    600
tcaa                                                                604
```

```
<210> SEQ ID NO 83
<211> LENGTH: 80
<212> TYPE: DNA
<213> ORGANISM: Artificial Sequence
<220> FEATURE:
<223> OTHER INFORMATION: N1366

<400> SEQUENCE: 83
gttgcaagaa atgcattatg caattttttg attatgacaa tctctcgaaa gcctacttgg    60
cttcacatac gttgcatacg                                                80
```

```
<210> SEQ ID NO 84
<211> LENGTH: 65
<212> TYPE: DNA
<213> ORGANISM: Artificial Sequence
<220> FEATURE:
<223> OTHER INFORMATION: N1368

<400> SEQUENCE: 84
atatgctggt gatgagtaat ctgttgtcat tttgaatatg tattatttgg ttatggttgt    60
atatg                                                                65
```

```
<210> SEQ ID NO 85
<211> LENGTH: 80
<212> TYPE: DNA
<213> ORGANISM: Artificial Sequence
<220> FEATURE:
<223> OTHER INFORMATION: N1371

<400> SEQUENCE: 85
aaaaactaat acgtaaacct gcattaaggt aagattatat cagaaaatgt gttgcaagaa    60
atgcattatg caattttttg                                                80
```

```
<210> SEQ ID NO 86
<211> LENGTH: 85
<212> TYPE: DNA
<213> ORGANISM: Artificial Sequence
<220> FEATURE:
<223> OTHER INFORMATION: N1372

<400> SEQUENCE: 86
tagaagctaa tctttaacct ggaagacagg acagaaaagt aattacaaga acatatgtga    60
aaaaaaatag ttgatatttt aaacc                                          85
```

```
<210> SEQ ID NO 87
<211> LENGTH: 25
<212> TYPE: DNA
<213> ORGANISM: Artificial Sequence
<220> FEATURE:
<223> OTHER INFORMATION: BK93

<400> SEQUENCE: 87
aaaaattgat tctcatcgta aatgc                                          25
```

<210> SEQ ID NO 88
<211> LENGTH: 30
<212> TYPE: DNA
<213> ORGANISM: Artificial Sequence
<220> FEATURE:
<223> OTHER INFORMATION: N1114

<400> SEQUENCE: 88

```
atatgctggt gatgagtaat ctgttgtcat                                30
```

<210> SEQ ID NO 89
<211> LENGTH: 6728
<212> TYPE: DNA
<213> ORGANISM: Artificial Sequence
<220> FEATURE:
<223> OTHER INFORMATION: pJT254

<400> SEQUENCE: 89

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgcgtg   120
ttggcgggtg tcggggctgg cttaactatg cggcatcaga gcagattgta ctgagagtgc   180
accataaatt cccgttttaa gagcttggtg agcgctagga gtcactgcca ggtatcgttt   240
gaacacggca ttagtcaggg aagtcataac acagtccttt cccgcaattt tcttttttcta  300 ttactcttgg cctcctctag tacactctat atttttttat gcctcggtaa tgattttcat   360 ttttttttttt cccctagcgg atgactcttt tttttttctta gcgattggca ttatcacata  420
atgaattata cattatataa agtaatgtga tttcttcgaa gaatatacta aaaaatgagc   480
aggcaagata aacgaaggca aagatgacag agcagaaagc cctagtaaag cgtattacaa   540
atgaaaccaa gattcagatt gcgatctctt taaagggtgg tcccctagcg atagagcact   600
cgatcttccc agaaaaagag gcagaagcag tagcagaaca ggccacacaa tcgcaagtga   660
ttaacgtcca cacaggtata gggtttctgg accatatgat acatgctctg gccaagcatt   720
ccggctggtc gctaatcgtt gagtgcattg gtgacttaca catagacgac catcacacca   780
ctgaagactg cgggattgct ctcggtcaag cttttaaaga ggccctactg gcgcgtggag   840
taaaaaggtt tggatcagga tttgcgcctt tggatgaggc actttccaga gcggtggtag   900
atctttcgaa caggccgtac gcagttgtcg aacttggttt gcaaagggag aaagtaggag   960
atctctcttg cgagatgatc ccgcatttttc ttgaaagctt tgcagaggct agcagaatta  1020
ccctccacgt tgattgtctg cgaggcaaga atgatcatca ccgtagtgag agtgcgttca  1080
aggctcttgc ggttgccata agagaagcca cctcgcccaa tggtaccaac gatgttccct  1140
ccaccaaagg tgttcttatg tagtgacacc gattatttaa agctgcagca tacgatatat  1200
atacatgtgt atatatgtat acctatgaat gtcagtaagt atgtatacga acagtatgat  1260
actgaagatg acaaggtaat gcatcattct atacgtgtca ttctgaacga ggcgcgcttt  1320 ccttttttcct ttttgctttt tcttttttttt tctcttgaac tcgacggatc tatgcggtgt  1380
gaaataccgc acagatgcgt aaggagaaaa taccgcatca ggaaattgta aacgttaata  1440
ttttgttaaa attcgcgtta aattttttgtt aaatcagctc attttttaac caataggccg  1500
aaatcggcaa aatcccttat aaatcaaaag aatagaccga gatagggttg agtgttgttc  1560
cagtttggaa caagagtcca ctattaaaga acgtggactc caacgtcaaa gggcgaaaaa  1620
ccgtctatca gggcgatggc ccactacgtg aaccatcacc ctaatcaagt tttttggggt  1680
cgaggtgccg taaagcacta aatcggaacc ctaaagggag cccccgattt agagcttgac  1740
```

```
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggatgt gctgcaaggc     1980 gattaagttg ggtaacgcca gggttttccc agtcacgacg ttgtaaaacg acggccagtg    2040
agcgcgcgta atacgactca ctatagggcg aattgggtac cgggccccc ctcgaggtcg     2100 acggtatcga taagcttgat tagaagccgc cgagcgggcg acagccctcc gacggaagac    2160
tctcctccgt gcgtcctcgt cttcaccggt cgcgttcctg aaacgcagat gtgcctcgcg    2220
ccgcactgct ccgaacaata aagattctac aatactagct tttatggtta tgaagaggaa    2280
aaattggcag taacctggcc ccacaaacct tcaaattaac gaatcaaatt aacaaccata    2340
ggatgataat gcgattagtt ttttagcctt atttctgggg taattaatca gcgaagcgat    2400 gattttgat ctattaacag atatataaat ggaaaagctg cataaccact ttaactaata     2460 cttcaacat tttcagtttg tattacttct tattcaaatg tcataaaagt atcaacaaaa     2520
aattgttaat atacctctat actttaacgt caaggagaaa aatgtccaat ttactgcccg    2580
tacaccaaaa tttgcctgca ttaccggtcg atgcaacgag tgatgaggtt cgcaagaacc    2640
tgatggacat gttcagggat cgccaggcgt tttctgagca tacctggaaa atgcttctgt    2700
ccgtttgccg gtcgtgggcg gcatggtgca agttgaataa ccggaaatgg tttcccgcag    2760
aacctgaaga tgttcgcgat tatcttctat atcttcaggc gcgcggtctg gcagtaaaaa    2820
ctatccagca acatttgggc cagctaaaca tgcttcatcg tcggtccggg ctgccacgac    2880
caagtgacag caatgctgtt tcactggtta tgcggcggat ccgaaaagaa acgttgatg     2940 ccggtgaacg tgcaaaacag gctctagcgt tcgaacgcac tgatttcgac caggttcgtt    3000
cactcatgga aaatagcgat cgctgccagg atatacgtaa tctggcattt ctggggattg    3060
cttataacac cctgttacgt atagccgaaa ttgccaggat cagggttaaa gatatctcac    3120
gtactgacgg tgggagaatg ttaatccata ttggcagaac gaaaacgctg gttagcaccg    3180
caggtgtaga gaaggcactt agcctggggg taactaaact ggtcgagcga tggatttccg    3240
tctctggtgt agctgatgat ccgaataact acctgttttg ccgggtcaga aaaatggtg     3300 ttgccgcgcc atctgccacc agccagctat caactcgcgc cctggaaggg atttttgaag    3360
caactcatcg attgatttac ggcgctaagg atgactctgg tcagagatac ctggcctggt    3420
ctggacacag tgcccgtgtc ggagccgcgc gagatatggc ccgcgctgga gtttcaatac    3480
cggagatcat gcaagctggt ggctggacca atgtaaatat tgtcatgaac tatatccgta    3540
acctggatag tgaaacaggg gcaatggtgc gcctgctgga agatggcgat taggagtaag    3600
cgaatttctt atgatttatg attttttatta ttaaataagt tataaaaaaa ataagtgtat    3660
acaaatttta aagtgactct taggttttaa acgaaaatt cttattcttg agtaactctt     3720
tcctgtaggt caggttgctt tctcaggtat agcatgaggt cgctcttatt gaccacacct    3780
ctaccggcat gccgagcaaa tgcctgcaaa tcgctcccca tttcacccaa ttgtagatat    3840
gctaactcca gcaatgagtt gatgaatctc ggtgtgtatt ttatgtcctc agaggacaac    3900
acctgtggtg ttctagagcg gccgccaccg cggtggagct ccagcttttg ttccctttag    3960
tgagggttaa ttgcgcgctt ggcgtaatca tggtcatagc tgtttcctgt gtgaaattgt    4020
tatccgctca caattccaca caacatagga gccggaagca taaagtgtaa agcctggggt    4080
```

```
gcctaatgag tgaggtaact cacattaatt gcgttgcgct cactgcccgc tttccagtcg    4140
ggaaacctgt cgtgccagct gcattaatga atcggccaac gcgcgggggag aggcggtttg   4200 cgtattgggc gctcttccgc ttcctcgctc actgactcgc tgcgctcggt cgttcggctg    4260
cggcgagcgg tatcagctca ctcaaaggcg gtaatacggt tatccacaga atcagggggat   4320 aacgcaggaa agaacatgtg agcaaaaggc cagcaaaagg ccaggaaccg taaaaaggcc    4380
gcgttgctgg cgttttttcca taggctccgc cccctgacg agcatcacaa aaatcgacgc    4440
tcaagtcaga ggtggcgaaa cccgacagga ctataaagat accaggcgtt tccccctgga    4500
agctccctcg tgcgctctcc tgttccgacc ctgccgctta ccggatacct gtccgccttt    4560
ctcccttcgg aagcgtggc  gctttctcat agctcacgct gtaggtatct cagttcggtg    4620
taggtcgttc gctccaagct gggctgtgtg cacgaacccc ccgttcagcc cgaccgctgc    4680
gccttatccg gtaactatcg tcttgagtcc aacccggtaa gacacgactt atcgccactg    4740
gcagcagcca ctggtaacag gattagcaga gcgaggtatg taggcggtgc tacagagttc    4800
ttgaagtggt ggcctaacta cggctacact agaaggacag tatttggtat ctgcgctctg    4860
ctgaagccag ttaccttcgg aaaaagagtt ggtagctctt gatccggcaa acaaaccacc    4920
gctggtagcg gtggtttttt tgtttgcaag cagcagatta cgcgcagaaa aaaggatct    4980 caagaagatc ctttgatctt ttctacgggg tctgacgctc agtggaacga aaactcacgt    5040
taagggattt tggtcatgag attatcaaaa aggatcttca cctagatcct tttaaattaa    5100
aaatgaagtt ttaaatcaat ctaaagtata tatgagtaaa cttggtctga cagttaccaa    5160
tgcttaatca gtgaggcacc tatctcagcg atctgtctat ttcgttcatc catagttgcc    5220 tgactcccg tcgtgtagat aactacgata cgggagggct taccatctgg ccccagtgct    5280
gcaatgatac cgcgagaccc acgctcaccg gctccagatt tatcagcaat aaaccagcca    5340
gccggaaggg ccgagcgcag aagtggtcct gcaactttat ccgcctccat ccagtctatt    5400
aattgttgcc gggaagctag agtaagtagt tcgccagtta atagtttgcg caacgttgtt    5460
gccattgcta caggcatcgt ggtgtcacgc tcgtcgtttg gtatggcttc attcagctcc    5520
ggttcccaac gatcaaggcg agttacatga tcccccatgt tgtgcaaaaa agcggttagc    5580
tccttcggtc ctccgatcgt tgtcagaagt aagttggccg cagtgttatc actcatggtt    5640
atggcagcac tgcataattc tcttactgtc atgccatccg taagatgctt ttctgtgact    5700
ggtgagtact caaccaagtc attctgagaa tagtgtatgc ggcgaccgag ttgctcttgc    5760
ccggcgtcaa tacgggataa taccgcgcca catagcagaa ctttaaaagt gctcatcatt    5820
ggaaaacgtt cttcggggcg aaaactctca aggatcttac cgctgttgag atccagttcg    5880
atgtaaccca ctcgtgcacc caactgatct tcagcatctt ttactttcac cagcgtttct    5940
gggtgagcaa aaacaggaag gcaaaatgcc gcaaaaaagg gaataagggc gacacggaaa    6000
tgttgaatac tcatactctt cctttttcaa tattattgaa gcatttatca gggttattgt    6060
ctcatgagcg gatacatatt tgaatgtatt tagaaaaata aacaaatagg ggttccgcgc    6120
acatttcccc gaaaagtgcc acctgggtcc ttttcatcac gtgctataaa aataattata    6180
atttaaattt tttaatataa atatataaat taaaaataga aagtaaaaaa agaaattaaa    6240
gaaaaaatag ttttttgtttt ccgaagatgt aaaagactct agggggatcg ccaacaaata    6300
ctacctttta tcttgctctt cctgctctca ggtattaatg ccgaattgtt tcatcttgtc    6360
tgtgtagaag accacacacg aaaatcctgt gattttacat tttacttatc gttaatcgaa    6420
tgtatatcta tttaatctgc ttttcttgtc taataaatat atatgtaaag tacgcttttt    6480
```

```
gttgaaattt tttaaacctt tgtttatttt ttttcttca ttccgtaact cttctacctt    6540 cttatttac tttctaaaat ccaaatacaa aacataaaaa taaataaaca cagagtaaat    6600
tcccaaatta ttccatcatt aaaagatacg aggcgcgtgt aagttacagg caagcgatcc    6660
gtcctaagaa accattatta tcatgacatt aacctataaa aataggcgta tcacgaggcc    6720
ctttcgtc                                                            6728
```

<210> SEQ ID NO 90
<211> LENGTH: 22
<212> TYPE: DNA
<213> ORGANISM: Artificial Sequence
<220> FEATURE:
<223> OTHER INFORMATION: N160SeqF5

<400> SEQUENCE: 90

```
cctgaagtct aggtccctat tt                                              22
```

<210> SEQ ID NO 91
<211> LENGTH: 1650
<212> TYPE: DNA
<213> ORGANISM: Saccharomyces cerevisiae

<400> SEQUENCE: 91

```
atgaagctgg agcgcgtgag ttctaacggg agctttaagc gtggccgtga catccaaagt      60
ttggagagtc cgtgtacccg cccattaaag aaaatgtcgc catcaccttc atttacgagc     120
ctgaagatgg aaaaaccgtt taaggacatt gttcgaaaat acgggggtca cctgcaccag     180
tcctcgtata acccaggttc ttcaaaagtt gaactcgtgc gtccggacct gagcttgaaa     240
acggaccaat cattttttgca gagcagcgtg cagacaaccc cgaacaaaaa gagttgtaac     300
gagtatctgt ccacacccga agccactccc cttaagaaca cggccaccga gaatgcgtgg     360
gctacgtcaa gggtggtgag cgcatcaagc ctgtcaatcg tcacgccgac cgaaatcaaa     420
aatatactgg ttgacgagtt tagtgaacta aaacttggtc agcccttaac agcccagcac     480
caacggagcc atgcagtttt cgagatacct gagatcgtag agaacataat caagatgatc     540
gtttccctcg agagcgccaa tattccgaaa gaacgtccgt gcctgcgtcg caacccgcag     600
agttatgagc attcccttct gatgtataaa gacgaggaac gcgcgaagaa agcatggtcc     660
gcggctcaac aactgcgcga tccgccgctg gtgggtcata aggaaaaaaa acagggcgct     720
ctgtttagct gcatgatggt caaccgcctg tggttgaatg tcacgcgtcc gttcttattt     780
aagtctctgc atttcaaatc agtgcacaac ttcaaagaat ttctgcgcac aagtcaggaa     840
accacgcaag tgatgaggcc atcgcacttt atcctgcata aattgcacca ggtaacgcag     900
ccggatattg agagactgtc tagaatgaa tgccagaacc tcaagtggtt ggaatttat      960 gtatgtcccc gtattacacc tccactgtct tggttcgaca atttgcataa gttagaaaaa    1020
ttaatcatcc ccggaaacaa gaatatcgac gataatttcc tcttacggct gtctcagagt    1080
attcctaacc tgaaacacct cgtgcttcgt gcttgcgaca atgtttccga tagtggtgta    1140
gtttgtatcg ccctgaactg ccctaagctg aagacgttca acatcggacg tcatcgccgc    1200
ggcaatctga ttcatcagt tagcttggtt gccctgggta agtatacgca agttgagacc    1260
gttggttttg caggctgcga tgtggacgac gcaggcatat gggagttcgc gcgtttaaac    1320
gggaaaaacg tcgagcgcct gtcactcaac agttgccggc ttttaaccga ctatagcttg    1380
ccaatcctgt ttgcccttaa tagtttcccg aaccttgcgg tgttggaaat tcgaaaccctc    1440
```

-continued

```
gataaaatta cagatgtccg ccattttgtg aaatataatc tgtggaagaa atcactggat    1500
gctcctatcc tgattgaggc gtgcgaacgc ataacaaagc tgattgatca ggaagagaac    1560
cgggtcaaac gcataaatag cctggtcgct ttaaaggata tgaccgcgtg ggtgaacgct    1620
gacgatgaaa ttgaaaacaa cgtcgattga                                     1650
```

<210> SEQ ID NO 92
<211> LENGTH: 549
<212> TYPE: PRT
<213> ORGANISM: Saccharomyces cerevisiae

<400> SEQUENCE: 92

```
Met Lys Leu Glu Arg Val Ser Ser Asn Gly Ser Phe Lys Arg Gly Arg
1               5                   10                  15

Asp Ile Gln Ser Leu Glu Ser Pro Cys Thr Arg Pro Leu Lys Lys Met
            20                  25                  30

Ser Pro Ser Pro Ser Phe Thr Ser Leu Lys Met Glu Lys Pro Phe Lys
        35                  40                  45

Asp Ile Val Arg Lys Tyr Gly Gly His Leu His Gln Ser Ser Tyr Asn
    50                  55                  60

Pro Gly Ser Ser Lys Val Glu Leu Val Arg Pro Asp Leu Ser Leu Lys
65                  70                  75                  80

Thr Asp Gln Ser Phe Leu Gln Ser Ser Val Gln Thr Thr Pro Asn Lys
                85                  90                  95

Lys Ser Cys Asn Glu Tyr Leu Ser Thr Pro Glu Ala Thr Pro Leu Lys
            100                 105                 110

Asn Thr Ala Thr Glu Asn Ala Trp Ala Thr Ser Arg Val Val Ser Ala
        115                 120                 125

Ser Ser Leu Ser Ile Val Thr Pro Thr Glu Ile Lys Asn Ile Leu Val
    130                 135                 140

Asp Glu Phe Ser Glu Leu Lys Leu Gly Gln Pro Leu Thr Ala Gln His
145                 150                 155                 160

Gln Arg Ser His Ala Val Phe Glu Ile Pro Glu Ile Val Glu Asn Ile
                165                 170                 175

Ile Lys Met Ile Val Ser Leu Glu Ser Ala Asn Ile Pro Lys Glu Arg
            180                 185                 190

Pro Cys Leu Arg Arg Asn Pro Gln Ser Tyr Glu His Ser Leu Leu Met
        195                 200                 205

Tyr Lys Asp Glu Glu Arg Ala Lys Lys Ala Trp Ser Ala Ala Gln Gln
    210                 215                 220

Leu Arg Asp Pro Pro Leu Val Gly His Lys Glu Lys Gln Gly Ala
225                 230                 235                 240

Leu Phe Ser Cys Met Met Val Asn Arg Leu Trp Leu Asn Val Thr Arg
                245                 250                 255

Pro Phe Leu Phe Lys Ser Leu His Phe Lys Ser Val His Asn Phe Lys
            260                 265                 270

Glu Phe Leu Arg Thr Ser Gln Glu Thr Thr Gln Val Met Arg Pro Ser
        275                 280                 285

His Phe Ile Leu His Lys Leu His Gln Val Thr Gln Pro Asp Ile Glu
    290                 295                 300

Arg Leu Ser Arg Met Glu Cys Gln Asn Leu Lys Trp Leu Glu Phe Tyr
305                 310                 315                 320

Val Cys Pro Arg Ile Thr Pro Pro Leu Ser Trp Phe Asp Asn Leu His
                325                 330                 335
```

```
Lys Leu Glu Lys Leu Ile Ile Pro Gly Asn Lys Asn Ile Asp Asp Asn
            340                 345                 350

Phe Leu Leu Arg Leu Ser Gln Ser Ile Pro Asn Leu Lys His Leu Val
        355                 360                 365

Leu Arg Ala Cys Asp Asn Val Ser Asp Ser Gly Val Val Cys Ile Ala
    370                 375                 380

Leu Asn Cys Pro Lys Leu Lys Thr Phe Asn Ile Gly Arg His Arg Arg
385                 390                 395                 400

Gly Asn Leu Ile Thr Ser Val Ser Leu Val Ala Leu Gly Lys Tyr Thr
                405                 410                 415

Gln Val Glu Thr Val Gly Phe Ala Gly Cys Asp Val Asp Asp Ala Gly
            420                 425                 430

Ile Trp Glu Phe Ala Arg Leu Asn Gly Lys Asn Val Glu Arg Leu Ser
        435                 440                 445

Leu Asn Ser Cys Arg Leu Leu Thr Asp Tyr Ser Leu Pro Ile Leu Phe
    450                 455                 460

Ala Leu Asn Ser Phe Pro Asn Leu Ala Val Leu Glu Ile Arg Asn Leu
465                 470                 475                 480

Asp Lys Ile Thr Asp Val Arg His Phe Val Lys Tyr Asn Leu Trp Lys
                485                 490                 495

Lys Ser Leu Asp Ala Pro Ile Leu Ile Glu Ala Cys Glu Arg Ile Thr
            500                 505                 510

Lys Leu Ile Asp Gln Glu Glu Asn Arg Val Lys Arg Ile Asn Ser Leu
        515                 520                 525

Val Ala Leu Lys Asp Met Thr Ala Trp Val Asn Ala Asp Asp Glu Ile
    530                 535                 540

Glu Asn Asn Val Asp
545

<210> SEQ ID NO 93
<211> LENGTH: 6638
<212> TYPE: DNA
<213> ORGANISM: Artificial Sequence
<220> FEATURE:
<223> OTHER INFORMATION: pLA67

<400> SEQUENCE: 93
aaacgccagc aacgcggcct ttttacggtt cctggccttt tgctggcctt ttgctcacat    60
gttctttcct gcgttatccc ctgattctgt ggataaccgt attaccgcct tgagtgagc   120 tgataccgct cgccgcagcc gaacgaccga gcgcagcgag tcagtgagcg aggaagcgga   180
agagcgccca atacgcaaac cgcctctccc cgcgcgttgg ccgattcatt aatgcagctg   240
gcacgacagg tttcccgact ggaaagcggg cagtgagcgc aacgcaatta atgtgagtta   300
gctcactcat taggcacccc aggctttaca ctttatgctt ccggctcgta tgttgtgtgg   360
aattgtgagc ggataacaat ttcacacagg aaacagctat gaccatgatt acgccaagct   420
tgcatgcctg caggtcgact ctagaggatc cgcattgcgg attacgtatt ctaatgttca   480
gtaccgttcg tataatgtat gctatacgaa gttatgcaga ttgtactgag agtgcaccat   540
accacagctt tcaattcaa ttcatcattt ttttttatt cttttttttg atttcggttt   600
ctttgaaatt ttttgattc ggtaatctcc gaacagaagg aagaacgaag gaggagcac    660 agacttagat tggtatatat acgcatatgt agtgttgaag aaacatgaaa ttgcccagta   720
ttcttaaccc aactgcacag aacaaaaacc tgcaggaaac gaagataaat catgtcgaaa   780
gctacatata aggaacgtgc tgctactcat cctagtcctg ttgctgccaa gctatttaat   840
```

```
atcatgcacg aaaagcaaac aaacttgtgt gcttcattgg atgttcgtac caccaaggaa      900
ttactggagt tagttgaagc attaggtccc aaaatttgtt tactaaaaac acatgtggat      960
atcttgactg attttccat ggagggcaca gttaagccgc taaaggcatt atccgccaag      1020 tacaatttt tactcttcga agacagaaaa tttgctgaca ttggtaatac agtcaaattg      1080
cagtactctg cgggtgtata cagaatagca gaatgggcag acattacgaa tgcacacggt      1140
gtggtgggcc caggtattgt tagcggtttg aagcaggcgg cagaagaagt aacaaaggaa      1200
cctagaggcc ttttgatgtt agcagaattg tcatgcaagg gctccctatc tactggagaa      1260
tatactaagg gtactgttga cattgcgaag agcgacaaaa attttgttat cggctttatt      1320
gctcaaagag acatgggtgg aagagatgaa ggttacgatt ggttgattat gacacccggt      1380
gtgggtttag atgacaaggg agacgcattg ggtcaacagt atagaaccgt ggatgatgtg      1440
gtctctacag gatctgacat tattattgtt ggaagaggac tatttgcaaa gggaagggat      1500
gctaaggtag agggtgaacg ttacagaaaa gcaggctggg aagcatattt gagaagatgc      1560
ggccagcaaa actaaaaaac tgtattataa gtaaatgcat gtatactaaa ctcacaaatt      1620
agagcttcaa tttaattata tcagttatta ccctatgcgg tgtgaaatac cgcacagatg      1680
cgtaaggaga aaataccgca tcaggaaatt gtaaacgtta atattttgtt aaaattcgcg      1740
ttaaattttt gttaaatcag ctcatttttt aaccataggg ccgaaatcgg caaaatccct      1800
tataaatcaa agaatagac cgagataggg ttgagtgttg ttccagtttg gaacaagagt      1860
ccactattaa agaacgtgga ctccaacgtc aaagggcgaa aaaccgtcta tcagggcgat      1920
ggcccactac gtgaaccatc accctaatca agataacttc gtataatgta tgctatacga      1980
acggtaccag tgatgataca acgagttagc caaggtgaat tcgacttagg atgtctcatc      2040
aatcatctta ttcctgctgg tgttttttgt atcgccttgc cttggagtgt ttatgcttgt      2100
cctttgttca gtaaccattc ttcaagtttg tttcaagtag taggatacct tcagatatac      2160
gaaagaaagg gagtatagtt gtggatatat atatatatag caacccttct ttataagggt      2220
cctatagact atactcttca cactttaaag tacggaatta aggcccaagg gaactaacaa      2280
aaacgttcaa aaagttttaa aactatatgt gttaactgta caaaaataac ttatttatca      2340 tatcatttt ttctctgttt atttcttcta gaacttatac ctgtcttttc cttttattct      2400
ttgaatttgk tttaatatcc ttttttgktt taatatccat ccattccttt cacttagaac      2460
taataattcc cttcgtttga taatttatca ttttccttt ctgttagtaa agtacccatt      2520
aaatgaagct ggagcgcgtg agttctaacg ggagctttaa gcgtggccgt gacatccaaa      2580
gtttggagag tccgtgtacc cgcccattaa agaaaatgtc gccatcacct tcatttacga      2640
gcctgaagat ggaaaaaccg tttaaggaca ttgttcgaaa atacgggggt cacctgcacc      2700
agtcctcgta taacccaggt tcttcaaaag ttgaactcgt gcgtccggac ctgagcttga      2760
aaacggacca atcattttg cagagcagcg tgcagacaac cccgaacaaa aagagttgta      2820
acgagtatct gtccacaccc gaagccactc cccttaagaa cacggccacc gagaatgcgt      2880
gggctacgtc aagggtggtg agcgcatcaa gcctgtcaat cgtcacgccg accgaaatca      2940
aaaatatact ggttgacgag tttagtgaac taaaacttgg tcagcccctta acagcccagc      3000 accaacggag ccatgcagtt ttcgagatac ctgagatcgt agagaacata atcaagatga      3060
tcgtttccct cgagagcgcc aatattccga aagaacgtcc gtgcctgcgt cgcaacccgc      3120
agagttatga gcattccctt ctgatgtata aagacgagga acgcgcgaag aaagcatggt      3180
```

```
ccgcggctca caactgcgc gatccgccgc tggtgggtca taaggaaaaa aaacagggcg    3240
ctctgtttag ctgcatgatg gtcaaccgcc tgtggttgaa tgtcacgcgt ccgttcttat    3300
ttaagtctct gcatttcaaa tcagtgcaca acttcaaaga atttctgcgc acaagtcagg    3360
aaaccacgca agtgatgagg ccatcgcact ttatcctgca taaattgcac caggtaacgc    3420
agccggatat tgagagactg tctagaatgg aatgccagaa cctcaagtgg ttggaatttt    3480
atgtatgtcc ccgtattaca cctccactgt cttggttcga caatttgcat aagttagaaa    3540
aattaatcat ccccggaaac aagaatatcg acgataattt cctcttacgg ctgtctcaga    3600
gtattcctaa cctgaaacac ctcgtgcttc gtgcttgcga caatgtttcc gatagtggtg    3660
tagtttgtat cgccctgaac tgccctaagc tgaagacgtt caacatcgga cgtcatcgcc    3720
gcggcaatct gattacatca gttagcttgg ttgccctggg taagtatacg caagttgaga    3780
ccgttggttt tgcaggctgc gatgtggacg acgcaggcat atgggagttc gcgcgtttaa    3840
acgggaaaaa cgtcgagcgc ctgtcactca acagttgccg gcttttaacc gactatagct    3900
tgccaatcct gtttgccctt aatagtttcc cgaaccttgc ggtgttggaa attcgaaacc    3960
tcgataaaat tacagatgtc cgccattttg tgaaatataa tctgtggaag aaatcactgg    4020
atgctcctat cctgattgag gcgtgcgaac gcataacaaa gctgattgat caggaagaga    4080
accgggtcaa acgcataaat agcctggtcg ctttaaagga tatgaccgcg tgggtgaacg    4140
ctgacgatga aattgaaaac aacgtcgatt gagacgatga aattgaaaac aacgtcgatt    4200
gaggtaccat ggttttgtg actttaccta taaatagtac acaacagacc accagtaatt    4260
ctacacactt cttaactgat aatattatta taattgtaac ttttttagcag cactaaattt    4320 aatgaataca tagatttttta actagcattt tactattctg tacttttttac ttgaaattcc    4380 agaagggccg aagaaccag aattccttca cagaaaacga attcactggc cgtcgtttta    4440
caacgtcgtg actgggaaaa ccctggcgtt acccaactta atcgccttgc agcacatccc    4500
cctttcgcca gctggcgtaa tagcgaagag gcccgcaccg atcgcccttc ccaacagttg    4560
cgcagcctga atggcgaatg gcgcctgatg cggtattttc tccttacgca tctgtgcggt    4620
atttcacacc gcatatggtg cactctcagt acaatctgct ctgatgccgc atagttaagc    4680
cagccccgac acccgccaac acccgctgac gcgccctgac gggcttgtct gctcccggca    4740
tccgcttaca gacaagctgt gaccgtctcc gggagctgca tgtgtcagag gttttcaccg    4800
tcatcaccga aacgcgcgag acgaaagggc ctcgtgatac gcctattttt ataggttaat    4860
gtcatgataa taatggtttc ttagacgtca ggtggcactt ttcggggaaa tgtgcgcgga    4920 accccctattt gtttattttt ctaaatacat tcaaatatgt atccgctcat gagacaataa    4980
ccctgataaa tgcttcaata atattgaaaa aggaagagta tgagtattca acatttccgt    5040
gtcgccctta ttccctttttt gcggcatttt gccttcctg ttttttgctca cccagaaacg    5100 ctggtgaaag taaaagatgc tgaagatcag ttgggtgcac gagtgggtta catcgaactg    5160
gatctcaaca gcggtaagat ccttgagagt tttcgccccg aagaacgttt tccaatgatg    5220
agcactttta aagttctgct atgtggcgcg gtattatccc gtattgacgc cgggcaagag    5280
caactcggtc gccgcataca ctattctcag aatgacttgg ttgagtactc accagtcaca    5340
gaaaagcatc ttacggatgg catgacagta agagaattat gcagtgctgc cataaccatg    5400
agtgataaca ctgcggccaa cttacttctg acaacgatcg gaggaccgaa ggagctaacc    5460 gctttttttgc acaacatggg ggatcatgta actcgccttg atcgttggga accggagctg    5520
aatgaagcca taccaaacga cgagcgtgac accacgatgc ctgtagcaat ggcaacaacg    5580
```

```
ttgcgcaaac tattaactgg cgaactactt actctagctt cccggcaaca attaatagac    5640
tggatggagg cggataaagt tgcaggacca cttctgcgct cggcccttcc ggctggctgg    5700
tttattgctg ataaatctgg agccggtgag cgtgggtctc gcggtatcat tgcagcactg    5760
gggccagatg gtaagccctc ccgtatcgta gttatctaca cgacggggag tcaggcaact    5820
atggatgaac gaaatagaca gatcgctgag ataggtgcct cactgattaa gcattggtaa    5880
ctgtcagacc aagtttactc atatatactt tagattgatt taaaacttca ttttttaattt   5940 aaaaggatct aggtgaagat cctttttgat aatctcatga ccaaaatccc ttaacgtgag    6000
ttttcgttcc actgagcgtc agaccccgta gaaaagatca aggatcttc ttgagatcct     6060 ttttttctgc gcgtaatctg ctgcttgcaa acaaaaaaac caccgctacc agcggtggtt    6120
tgtttgccgg atcaagagct accaactctt tttccgaagg taactggctt cagcagagcg    6180
cagataccaa atactgtcct tctagtgtag ccgtagttag gccaccactt caagaactct    6240
gtagcaccgc ctacatacct cgctctgcta atcctgttac cagtggctgc tgccagtggc    6300
gataagtcgt gtcttaccgg gttggactca agacgatagt taccggataa ggcgcagcgg    6360
tcgggctgaa cggggggttc gtgcacacag cccagcttgg agcgaacgac ctacaccgaa    6420
ctgagatacc tacagcgtga gctatgagaa agcgccacgc ttcccgaagg gagaaaggcg    6480
gacaggtatc cggtaagcgg cagggtcgga acaggagagc gcacgaggga gcttccaggg    6540
ggaaacgcct ggtatcttta gtcctgtc gggtttcgcc acctctgact tgagcgtcga     6600 ttttttgtgat gctcgtcagg ggggcggagc ctatggaa                          6638

<210> SEQ ID NO 94
<211> LENGTH: 100
<212> TYPE: DNA
<213> ORGANISM: Artificial Sequence
<220> FEATURE:
<223> OTHER INFORMATION: LA712

<400> SEQUENCE: 94
cttaattgaa agaaagaatt tccttcaact tcggtttcct ggttccgcta tttctcgctt     60
gtttcttcta gcattgcgga ttacgtattc taatgttcag                          100

<210> SEQ ID NO 95
<211> LENGTH: 30
<212> TYPE: DNA
<213> ORGANISM: Artificial Sequence
<220> FEATURE:
<223> OTHER INFORMATION: LA746

<400> SEQUENCE: 95
gttttctgtg aaggaattct ggtttcttcg                                      30

<210> SEQ ID NO 96
<211> LENGTH: 2815
<212> TYPE: DNA
<213> ORGANISM: Artificial Sequence
<220> FEATURE:
<223> OTHER INFORMATION: p[FBA1::HXT1_331]-alsS-PDC1t locus

<400> SEQUENCE: 96
aagtaaccta ttcaaagtaa tatctcatac atgtttcatg agggtaacaa catgcgactg     60
ggtgagcata tgttccgctg atgtgatgtg caagataaac ggccggccgc attgcggatt    120
acgtattcta atgttcagta ccgttcgtat aatgtatgct atacgaacgg taccagtgat    180
```

```
gatacaacga gttagccaag gtggcggccg cctacttggc ttcacatacg ttgcatacgt    240
cgatatagat aataatgata atgacagcag gattatcgta atacgtaata gttgaaaatc    300
tcaaaaatgt gtgggtcatt acgtaaataa tgataggaat gggattcttc tattttttcct   360 ttttccattc tagcagccgt cgggaaaacg tggcatcctc tctttcgggc tcaattggag    420
tcacgctgcc gtgagcatcc tctctttcca tatctaacaa ctgagcacgt aaccaatgga    480
aaagcatgag cttagcgaca gcgcaaagga ttatgacact gttgcattga gtcaaaagtt    540
tttccgaagt gacccagtgc tcttttttt ttccgtgaa ggactgacaa atatgcgcac     600
aagatccaat acgtaatgga aattcggaaa aactaggaag aaatgctgca gggcattgcc    660
gtgcgcttag cgttgctcca aaaagtatt ggatggttaa taccatttgt ctgttctctt    720
ctgactttga ctcctcaaaa aaaaaaaatc tacaatcaac agatcgcttc aattacgccc    780
tcacaaaaac ttttttcctt cttcttcgcc cacgttaaat tttatccctc atgttgtcta    840
acggatttct gcacttgatt tattataaaa agacaaagac ataatacttc tctatcaatt    900
tcagttattg ttcttccttg cgttattctt ctgttcttct ttttctttg tcatatataa    960 ccataaccaa gtaatacata ttcaattaat taaatgttga caaaagcaac aaaagaacaa    1020
aaatcccttg tgaaaaacag aggggcggag cttgttgttg attgcttagt ggagcaaggt    1080
gtcacacatg tatttggcat tccaggtgca aaaattgatg cggtatttga cgctttacaa    1140
gataaaggac ctgaaattat cgttgcccgg cacgaacaaa acgcagcatt catggcccaa    1200
gcagtcggcc gtttaactgg aaaaccggga gtcgtgttag tcacatcagg accgggtgcc    1260
tctaacttgg caacaggcct gctgacagcg aacactgaag gagaccctgt cgttgcgctt    1320
gctggaaacg tgatccgtgc agatcgttta aaacggacac atcaatcttt ggataatgcg    1380
gcgctattcc agccgattac aaaatacagt gtagaagttc aagatgtaaa aaatataccg    1440
gaagctgtta caaatgcatt taggatagcg tcagcagggc aggctggggc cgcttttgtg    1500 agcttttccgc aagatgttgt gaatgaagtc acaaatacga aaaacgtgcg tgctgttgca    1560
gcgccaaaac tcggtcctgc agcagatgat gcaatcagtg cggccatagc aaaaatccaa    1620
acagcaaaac ttcctgtcgt tttggtcggc atgaaaggcg gaagaccgga agcaattaaa    1680
gcggttcgca agcttttgaa aaaggttcag cttccatttg ttgaaacata tcaagctgcc    1740 ggtaccctt ctagagattt agaggatcaa tattttggcc gtatcggttt gttccgcaac    1800
cagcctggcg atttactgct agagcaggca gatgttgttc tgacgatcgg ctatgacccg    1860
attgaatatg atccgaaatt ctggaatatc aatggagacc ggacaattat ccatttagac    1920
gagattatcg ctgacattga tcatgcttac cagcctgatc ttgaattgat cggtgacatt    1980
ccgtccacga tcaatcatat cgaacacgat gctgtgaaag tggaatttgc agagcgtgag    2040
cagaaaatcc tttctgattt aaaacaatat atgcatgaag gtgagcaggt gcctgcagat    2100
tggaaatcag acagagcgca ccctcttgaa atcgttaaag agttgcgtaa tgcagtcgat    2160
gatcatgtta cagtaacttg cgatatcggt tcgcacgcca tttggatgtc acgttatttc    2220
cgcagctacg agccgttaac attaatgatc agtaacggta tgcaaacact cggcgttgcg    2280
cttccttggg caatcggcgc ttcattggtg aaaccgggaa aaaagtggt ttctgtctct    2340 ggtgacggcg gtttcttatt ctcagcaatg gaattagaga cagcagttcg actaaaagca    2400
ccaattgtac acattgtatg gaacgacagc acatatgaca tggttgcatt ccagcaattg    2460
aaaaaatata accgtacatc tgcggtcgat ttcggaaata tcgatatcgt gaatatgcg    2520 gaaagcttcg gagcaactgg cttgcgcgta gaatcaccag accagctggc agatgttctg    2580
```

```
cgtcaaggca tgaacgctga aggtcctgtc atcatcgatg tcccggttga ctacagtgat    2640
aacattaatt tagcaagtga caagcttccg aaagaattcg gggaactcat gaaaacgaaa    2700
gctctctagg tcgaggcgat ttaatctcta attattagtt aaagtttat aagcattttt     2760 atgtaacgaa aaataaattg gttcatatta ttactgcact gtcacttacc atgga         2815

<210> SEQ ID NO 97
<211> LENGTH: 12298
<212> TYPE: DNA
<213> ORGANISM: Artificial Sequence
<220> FEATURE:
<223> OTHER INFORMATION: pLH804::L2V4

<400> SEQUENCE: 97
tcccattacc gacatttggg cgctatacgt gcatatgttc atgtatgtat ctgtatttaa      60 aacactttg tattattttt cctcatatat gtgtataggt ttatacggat gatttaatta      120
ttacttcacc acccttattt tcaggctgat atcttagcct tgttactaga ttaatcatgt     180
aattagttat gtcacgctta cattcacgcc ctcccccac atccgctcta accgaaaagg      240
aaggagttag acaacctgaa gtctaggtcc ctatttattt ttttatagtt atgttagtat     300
taagaacgtt atttatattt caaattttc tttttttct gtacagacgc gtgtacgcat       360
gtaacattat actgaaaacc ttgcttgaga aggttttggg acgctcgaag gctttaattt     420
gcgggcggcc gcacctggta aaacctctag tggagtagta gatgtaatca atgaagcgga     480
agccaaaaga ccagagtaga ggcctataga agaaactgcg atacctttg tgatggctaa     540 acaaacagac atctttttat atgttttac ttctgtatat cgtgaagtag taagtgataa     600
gcgaatttgg ctaagaacgt tgtaagtgaa caagggacct cttttgcctt tcaaaaaagg    660
attaaatgga gttaatcatt gagatttagt tttcgttaga ttctgtatcc ctaaataact    720
cccttacccg acgggaaggc acaaaagact tgaataatag caaacggcca gtagccaaga   780
ccaaataata ctagagttaa ctgatggtct taaacaggca ttacgtggtg aactccaaga   840
ccaatataca aaatatcgat aagttattct tgcccaccaa tttaaggagc ctacatcagg   900
acagtagtac cattcctcag agaagaggta tacataacaa gaaaatcgcg tgaacacctt   960
atataactta gcccgttatt gagctaaaaa accttgcaaa atttcctatg aataagaata  1020
cttcagacgt gataaaaatt tactttctaa ctcttctcac gctgcccta tctgttcttc    1080 cgctctaccg tgagaaataa agcatcgagt acggcagttc gctgtcactg aactaaaaca   1140
ataaggctag ttcgaatgat gaacttgctt gctgtcaaac ttctgagttg ccgctgatgt   1200
gacactgtga caataaattc aaaccggtta tagcggtctc ctccggtacc ggttctgcca   1260
cctccaatag agctcagtag gagtcagaac ctctgcggtg gctgtcagtg actcatccgc   1320
gtttcgtaag ttgtgcgcgt gcacatttcg cccgttcccg ctcatcttgc agcaggcgga   1380
aattttcatc acgctgtagg acgcaaaaaa aaaataatta atcgtacaag aatcttggaa    1440
aaaaaattga aaaattttgt ataaaaggga tgacctaact tgactcaatg gcttttacac    1500
ccagtatttt cccttttcctt gtttgttaca attatagaag caagacaaaa acatatagac   1560
aacctattcc taggagttat atttttttac cctaccagca atataagtaa aaaactgttt    1620
aaacagtatg gaagaatgta agatggctaa gatttactac caagaagact gtaacttgtc   1680
cttgttggat ggtaagacta tcgccgttat cggttacggt tctcaaggtc acgctcatgc   1740
cctgaatgct aaggaatccg gttgtaacgt tatcattggt ttatacgaag gtgcggagga   1800
```

```
gtggaaaaga gctgaagaac aaggtttcga agtctacacc gctgctgaag ctgctaagaa    1860
ggctgacatc attatgatct tgatcccaga tgaaaagcag gctaccatgt acaaaaacga    1920
catcgaacca aacttggaag ccggtaacat gttgatgttc gctcacggtt tcaacatcca    1980
tttcggttgt attgttccac caaaggacgt tgatgtcact atgatcgctc aaagggtcc     2040 aggtcacacc gttagatccg aatacgaaga aggtaaaggt gtcccatgct tggttgctgt    2100
cgaacaagac gctactggca aggctttgga tatggctttg gcctacgctt tagccatcgg    2160
tggtgctaga gccggtgtct tggaaactac cttcagaacc gaaactgaaa ccgacttgtt    2220
cggtgaacaa gctgttttat gtggtggtgt ctgcgctttg atgcaggccg gttttgaaac    2280
cttggttgaa gccggttacg acccaagaaa cgcttacttc gaatgtatcc acgaaatgaa    2340
gttgatcgtt gacttgatct accaatctgg tttctccggt atgcgttact ctatctccaa    2400
cactgctgaa tacggtgact acattaccgg tccaaagatc attactgaag ataccaagaa    2460
ggctatgaag aagattttgt ctgacattca agatggtacc tttgccaagg acttcttggt    2520
tgacatgtct gatgctggtt cccaggtcca cttcaaggct atgagaaagt tggcctccga    2580
acacccagct gaagttgtcg gtgaagaaat tagatccttg tactcctggt ccgacgaaga    2640
caagttgatt aacaactgag gccctgcagg ccagaggaaa taatatcaa gtgctggaaa    2700 cttttttctct tggaatttt gcaacatcaa gtcatagtca attgaattga cccaatttca    2760
catttaagat ttttttttt tcatccgaca tacatctgta cactaggaag ccctgttttt    2820
ctgaagcagc ttcaaatata tatattttt acatatttat tatgattcaa tgaacaatct    2880
aattaaatcg aaaacaagaa ccgaaacgcg aataaataat ttatttagat ggtgacaagt    2940
gtataagtcc tcatcgggac agctacgatt tctctttcgg ttttggctga gctactggtt    3000
gctgtgacga gcggcatta gcgcggcgtt atgagctacc ctcgtggcct gaaagatggc    3060
gggaataaag cggaactaaa aattactgac tgagccatat tgaggtcaat tgtcaactc     3120 gtcaagtcac gtttggtgga cggccccttt ccaacgaatc gtatatacta acatgcgcgc    3180
gcttcctata tacacatata catatatata tatatatata tgtgtgcgtg tatgtgtaca    3240
cctgtattta atttccttac tcgcgggttt ttcttttttc tcaattcttg gcttcctctt    3300
tctcgagcgg accggatcct cgcgaactcc aaaatgagct atcaaaaacg atagatcgat    3360
taggatgact ttgaaatgac tccgcagtgg actggccgtt aatttcaagc gtgagtaaaa    3420
tagtgcatga caaaagatga gctaggcttt tgtaaaaata tcttacgttg taaaatttta    3480
gaaatcatta tttccttcat atcattttgt cattgacctt cagaagaaaa gagccgacca    3540
ataatataaa taaataaata aaaataatat tccattattt ctaaacagat tcaatactca    3600
ttaaaaaact atatcaatta atttgaatta acttaattaa ttattttttg ccagtttctt    3660
caggcttcca aaagtctgtt acggctcccc tagaagcaga cgaaacgatg tgagcatatt    3720
taccaaggat accgcgtgaa tagagcggtg gcaattcaat ggtctcttga cgatgtttta    3780
actcttcatc ggagatatca aagtgtaatt ccttagtgtc ttggtcaata gtgactatgt    3840
ctcctgtttg caggtaggcg attggaccgc catcttgtgc ttcaggagcg atatgaccca    3900
cgacaagacc ataagtacca cctgagaagc ggccatctgt cagaagggca acttttttcac   3960 cttgccctttt accaacaatc attgatgaaa gggaaagcat tcaggcata ccaggaccgc    4020 cctttggtcc tacaaaacgt acgacaacaa catcaccatc aacaatatca tcattcaaga    4080
cagcttcaat ggcttcttct tcagaattaa agaccttagc aggaccgaca tgacgacgca    4140
cttttacacc agaaactttg gcaacggcac cgtctggagc caagttacca tggagaataa    4200
```

```
tgaccggacc atcttcacgt ttaggatttt caagcggcat aataaccttt tgaccaggtg    4260
ttaaatcatc aaaagccttc aaattttcag cgactgtttt gccagtacaa gtgatacggt    4320
caccatgaag gaagccattt ttaaggagat atttcataac tgctggtacc cctccgacct    4380
tgtaaaggtc ttggaataca tattgaccag aaggtttcaa atcagccaaa tgaggaactt    4440
tttcttggaa agtattgaaa tcatcaagtg tcaattccac attagcagca tgggcaatag    4500
ctaagaggtg aagggttgag ttggttgaac ctcccagagc catagttaca gtaatagcat    4560
cttcaaaagc ttcacgcgtt aaaatgtcag aaggttttaa gcccatttcg agcattttga    4620
caacagcgcg accagcttct tcaatatctg cttttctttc tgcggattca gccgggtgag    4680
aagatgaacc cggaaggcta agtcccaaaa cttcaatagc tgtcgccatt gtgttagcag    4740
tatacatacc accgcagcct ccaggaccgg gacaagcatt acattccaaa gctttaactt    4800
cttctttggt catatcgccg tggttccaat ggccgacacc ttcaaagaca gagactaaat    4860
cgatatcttt gccgtctaaa ttaccaggtg caattgttcc gccgtaagca aaaatggctg    4920
ggatatccat gttagccata gcgataacag aaccgggcat gtttttatca caaccgccaa    4980
tggctacaaa agcatccgca ttatgacctc ccatggctgc ttcaatagaa tctgcaataa    5040
tatcacgaga tgtcaaggag aaacgcattc cttgggttcc catggcgatt ccatcagaaa    5100
ccgtgattgt tccgaactga actggccaag caccagcttc cttaacaccg actttggcta    5160
gtttaccaaa gtcatgtaag tggatattac aaggtgtgtt ttcagcccaa gttgaaatga    5220
caccgacgat aggttttttca aagtcttcat cttgcatacc agttgcacgc aacatagcac    5280
gattaggtga tttaaccatt gaatcgtaaa cagaactacg atttcttaag tctttaagag    5340 ttttttttgtc agtcatactc acgtgaaact tagattagat tgctatgctt tctttccaat    5400
gagcaagaag taaaaaaagt tgtaatagaa caggaaaaat gaagctgaaa cttgagaaat    5460
tgaagaccgt ttgttaactc aaatatcaat gggaggtcgt cgaaagagaa caaaatcgaa    5520
aaaaaagttt tcaagagaaa gaaacgtgat aaaaattttt attgccttct ccgacgaaga    5580
aaaagggacg aggcggtctc tttttccttt tccaaacctt tagtacgggt aattaacggc    5640
accctagagg aaggaggagg gggaatttag tatgctgtgc ttgggtgttt tgaagtggta    5700
cggcggtgcg cggagtccga gaaaatctgg aagagtaaaa aaggagtaga gacattttga    5760
agctatgccg gcagatctat ttaaatggcg cgccgacgtc aggtggcact tttcgggggaa    5820 atgtgcgcgg aaccccctatt tgtttatttt tctaaataca ttcaaatatg tatccgctca    5880
tgagacaata accctgataa atgcttcaat aatattgaaa aaggaagagt atgagtattc    5940
aacatttccg tgtcgccctt attcccttttt ttgcggcatt ttgccttcct gtttttgctc    6000
acccagaaac gctggtgaaa gtaaaagatg ctgaagatca gttgggtgca cgagtgggtt    6060
acatcgaact ggatctcaac agcggtaaga tccttgagag ttttcgcccc gaagaacgtt    6120
ttccaatgat gagcactttt aaagttctgc tatgtgcgc ggtattatcc cgtattgacg    6180
ccgggcaaga gcaactcggt cgccgcatac actattctca gaatgacttg gttgagtact    6240
caccagtcac agaaaagcat cttacggatg gcatgacagt aagagaatta tgcagtgctg    6300
ccataaccat gagtgataac actgcggcca acttacttct gacaacgatc ggaggaccga    6360
aggagctaac cgcttttttg cacaacatgg gggatcatgt aactcgcctt gatcgttggg    6420
aaccggagct gaatgaagcc ataccaaacg acgagcgtga caccacgatg cctgtagcaa    6480
tggcaacaac gttgcgcaaa ctattaactg gcgaactact tactctagct tcccggcaac    6540
```

```
aattaataga ctggatggag gcggataaag ttgcaggacc acttctgcgc tcggcccttc   6600
cggctggctg gtttattgct gataaatctg gagccggtga gcgtgggtct cgcggtatca   6660
ttgcagcact ggggccagat ggtaagccct cccgtatcgt agttatctac acgacgggga   6720
gtcaggcaac tatggatgaa cgaaatagac agatcgctga gataggtgcc tcactgatta   6780
agcattggta actgtcagac caagtttact catatatact ttagattgat ttaaaacttc   6840
atttttaatt taaaaggatc taggtgaaga tcctttttga taatctcatg accaaaatcc   6900
cttaacgtga gttttcgttc cactgagcgt cagaccccgt agaaaagatc aaaggatctt   6960
cttgagatcc tttttttctg cgcgtaatct gctgcttgca aacaaaaaaa ccaccgctac   7020
cagcggtggt ttgtttgccg gatcaagagc taccaactct ttttccgaag gtaactggct   7080
tcagcagagc gcagatacca atactgttc ttctagtgta gccgtagtta ggccaccact   7140
tcaagaactc tgtagcaccg cctacatacc tcgctctgct aatcctgtta ccagtggctg   7200
ctgccagtgg cgataagtcg tgtcttaccg ggttggactc aagacgatag ttaccggata   7260
aggcgcagcg gtcgggctga cgggggggtt cgtgcacaca gcccagcttg gagcgaacga   7320
cctacaccga actgagatac ctacagcgtg agctatgaga aagcgccacg cttcccgaag   7380
ggagaaaggc ggacaggtat ccggtaagcg gcagggtcgg aacaggagag cgcacgaggg   7440
agcttccagg gggaaacgcc tggtatcttt atagtcctgt cgggtttcgc cacctctgac   7500
ttgagcgtcg attttgtga tgctcgtcag ggggcggag cctatggaaa aacgccagca   7560
acgcggcctt tttacggttc ctggcctttt gctggccttt tgctcacatg ttctttcctg   7620
cgttatcccc tgattctgtg gataaccgta ttaccgcctt tgagtgagct gataccgctc   7680
gccgcagccg aacgaccgag cgcagcgagt cagtgagcga ggaagcggaa gagcgcccaa   7740
tacgcaaacc gcctctcccc gcgcgttggc cgattcatta atgcagctgg cacgacaggt   7800
ttcccgactg gaaagcgggc agtgagcgca acgcaattaa tgtgagttag ctcactcatt   7860
aggcacccca ggctttacac tttatgcttc cggctcgtat gttgtgtgga attgtgagcg   7920
gataacaatt tcacacagga aacagctatg accatgatta cgccaagctt tttctttcca   7980
attttttttt tttcgtcatt ataaaaatca ttacgaccga gattcccggg taataactga   8040
tataattaaa ttgaagctct aatttgtgag tttagtatac atgcatttac ttataataca   8100
gttttttagt tttgctggcc gcatcttctc aaatatgctt cccagcctgc ttttctgtaa   8160
cgttcaccct ctaccttagc atcccttccc tttgcaaata gtcctcttcc aacaataata   8220
atgtcagatc ctgtagagac cacatcatcc acggttctat actgttgacc caatgcgtct   8280
cccttgtcat ctaaacccac accgggtgtc ataatcaacc aatcgtaacc ttcatctctt   8340
ccacccatgt ctctttgagc aataaagccg ataacaaaat ctttgtcgct cttcgcaatg   8400
tcaacagtac ccttagtata ttctccagta gatagggagc ccttgcatga caattctgct   8460
aacatcaaaa ggcctctagg ttcctttgtt acttcttctg ccgcctgctt caaaccgcta   8520
acaatacctg ggcccaccac accgtgtgca ttcgtaatgt ctgcccattc tgctattctg   8580
tatacacccg cagagtactg caatttgact gtattaccaa tgtcagcaaa ttttctgtct   8640
tcgaagagta aaaaattgta cttggcggat aatgccttta gcggcttaac tgtgccctcc   8700
atggaaaaat cagtcaagat atccacatgt gttttagta aacaattttt gggacctaat   8760
gcttcaacta actccagtaa ttccttggtg gtacgaacat ccaatgaagc acacaagttt   8820
gtttgctttt cgtgcatgat attaaatagc ttggcagcaa caggactagg atgagtagca   8880
gcacgttcct tatatgtagc tttcgacatg atttatcttc gtttcctgca ggtttttgtt   8940
```

```
ctgtgcagtt gggttaagaa tactgggcaa tttcatgttt cttcaacact acatatgcgt    9000
atatatacca atctaagtct gtgctccttc cttcgttctt ccttctgttc ggagattacc    9060
gaatcaaaaa aatttcaagg aaaccgaaat caaaaaaaag aataaaaaaa aaatgatgaa    9120
ttgaaaagct tgcatgcctg caggtcgact ctagtatact ccgtctactg tacgatacac    9180
ttccgctcag gtccttgtcc tttaacgagg ccttaccact cttttgttac tctattgatc    9240
cagctcagca aaggcagtgt gatctaagat tctatcttcg cgatgtagta aaactagcta    9300
gaccgagaaa gagactagaa atgcaaaagg cacttctaca atggctgcca tcattattat    9360
ccgatgtgac gctgcatttt ttttttttt ttttttttt ttttttttt ttttttttt    9420 tttttttgt acaaatatca taaaaaaga gaatctttt aagcaaggat tttcttaact    9480
tcttcggcga cagcatcacc gacttcggtg gtactgttgg aaccacctaa atcaccagtt    9540
ctgatacctg catccaaaac ctttttaact gcatcttcaa tggctttacc ttcttcaggc    9600
aagttcaatg acaatttcaa catcattgca gcagacaaga tagtggcgat agggttgacc    9660
ttattctttg gcaaatctgg agcggaacca tggcatggtt cgtacaaacc aaatgcggtg    9720
ttcttgtctg gcaaagaggc caaggacgca gatggcaaca acccaagga gcctgggata    9780 acggaggctt catcggagat gatatcacca aacatgttgc tggtgattat ataccattt    9840 aggtgggttg ggttcttaac taggatcatg gcggcagaat caatcaattg atgttgaact    9900
ttcaatgtag ggaattcgtt cttgatggtt tcctccacag tttttctcca taatcttgaa    9960
gaggccaaaa cattagcttt atccaaggac caaataggca atggtggctc atgttgtagg   10020
gccatgaaag cggccattct tgtgattctt tgcacttctg gaacggtgta ttgttcacta   10080
tcccaagcga caccatcacc atcgtcttcc tttctcttac caaagtaaat acctcccact   10140
aattctctaa caacaacgaa gtcagtacct ttagcaaatt gtggcttgat tggagataag   10200
tctaaaagag agtcggatgc aaagttacat ggtcttaagt tggcgtacaa ttgaagttct   10260
ttacggattt ttagtaaacc ttgttcaggt ctaacactac cggtaccccca tttaggacca   10320 cccacagcac ctaacaaaac ggcatcagcc ttcttggagg cttccagcgc ctcatctgga   10380
agtggaacac ctgtagcatc gatagcagca ccaccaatta aatgatttc gaaatcgaac   10440 ttgacattgg aacgaacatc agaaatagct ttaagaacct taatggcttc ggctgtgatt   10500
tcttgaccaa cgtggtcacc tggcaaaacg acgatcttct taggggcaga cattacaatg   10560
gtatatcctt gaaatatata taaaaaaaaa aaaaaaaaa aaaaaaaaa atgcagcttc   10620 tcaatgatat tcgaatacgc tttgaggaga tacagcctaa tatccgacaa actgttttac   10680
agatttacga tcgtacttgt tacccatcat tgaattttga acatccgaac ctgggagttt   10740
tccctgaaac agatagtata tttgaacctg tataataata tatagtctag cgctttacgg   10800
aagacaatgt atgtatttcg gttcctggag aaactattgc atctattgca taggtaatct   10860
tgcacgtcgc atccccggtt cattttctgc gtttccatct tgcacttcaa tagcatatct   10920
ttgttaacga agcatctgtg cttcattttg tagaacaaaa atgcaacgcg agagcgctaa   10980
tttttcaaac aaagaatctg agctgcattt ttacagaaca gaaatgcaac gcgaaagcgc   11040
tattttacca acgaagaatc tgtgcttcat ttttgtaaaa caaaaatgca acgcgagagc   11100
gctaattttt caaacaaaga atctgagctg cattttaca gaacagaaat gcaacgcgag   11160
agcgctattt taccaacaaa gaatctatac ttcttttttg ttctacaaaa atgcatcccg   11220
agagcgctat ttttctaaca aagcatctta gattactttt tttctccttt gtgcgctcta   11280
```

| | |
|---|---|
| taatgcagtc tcttgataac tttttgcact gtaggtccgt taaggttaga agaaggctac | 11340 |
| tttggtgtct attttctctt ccataaaaaa agcctgactc cacttcccgc gtttactgat | 11400 |
| tactagcgaa gctgcgggtg cattttttca agataaaggc atccccgatt atattctata | 11460 |
| ccgatgtgga ttgcgcatac tttgtgaaca gaaagtgata gcgttgatga ttcttcattg | 11520 |
| gtcagaaaat tatgaacggt ttcttctatt ttgtctctat atactacgta taggaaatgt | 11580 |
| ttacattttc gtattgtttt cgattcactc tatgaatagt tcttactaca attttttgt | 11640 |
| ctaaagagta atactagaga taaacataaa aaatgtagag gtcgagttta gatgcaagtt | 11700 |
| caaggagcga aaggtggatg ggtaggttat atagggatat agcacagaga tatatagcaa | 11760 |
| agagatactt ttgagcaatg tttgtggaag cggtattcgc aatatttag tagctcgtta | 11820 |
| cagtccggtg cgttttggt ttttgaaag tgcgtcttca gagcgctttt ggttttcaaa | 11880 |
| agcgctctga agttcctata cttctagag aataggaact tcggaatagg aacttcaaag | 11940 |
| cgtttccgaa aacgagcgct tccgaaaatg caacgcgagc tgcgcacata cagctcactg | 12000 |
| ttcacgtcgc acctatatct gcgtgttgcc tgtatatata tatacatgag aagaacggca | 12060 |
| tagtgcgtgt ttatgcttaa atgcgtactt atatgcgtct atttatgtag gatgaaaggt | 12120 |
| agtctagtac ctcctgtgat attatcccat tccatgcggg gtatcgtatg cttccttcag | 12180 |
| cactacccctt tagctgttct atatgctgcc actcctcaat tggattagtc tcatccttca | 12240 |
| atgctatcat ttcctttgat attggatcat atgcatagta ccgagaaact agaggatc | 12298 |

<210> SEQ ID NO 98
<211> LENGTH: 11013
<212> TYPE: DNA
<213> ORGANISM: Artificial Sequence
<220> FEATURE:
<223> OTHER INFORMATION: pRS413::BiADH-kivD_Lg(y)

<400> SEQUENCE: 98

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgcgtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat attttttat gcctcggtaa tgattttcat | 360 |
| ttttttttt cccctagcgg atgactcttt ttttttctta gcgattggca ttatcacata | 420 |
| atgaattata cattatataa agtaatgtga tttcttcgaa gaatatacta aaaaatgagc | 480 |
| aggcaagata aacgaaggca aagatgacag agcagaaagc cctagtaaag cgtattacaa | 540 |
| atgaaaccaa gattcagatt gcgatctctt taaagggtgg tcccctagcg atagagcact | 600 |
| cgatcttccc agaaaaagag gcagaagcag tagcagaaca ggccacacaa tcgcaagtga | 660 |
| ttaacgtcca cacaggtata gggtttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag ctttaaaga ggccctactg gcgcgtggag | 840 |
| taaaaaggtt tggatcagga tttgcgcctt tggatgaggc actttccaga gcggtggtag | 900 |
| atctttcgaa caggccgtac gcagttgtcg aacttggttt gcaaagggag aaagtaggag | 960 |
| atctctcttg cgagatgatc ccgcattttc ttgaaagctt tgcagaggct agcagaatta | 1020 |
| ccctccacgt tgattgtctg cgaggcaaga atgatcatca ccgtagtgag agtgcgttca | 1080 |

```
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320 cctttttttct ttttgctttt tctttttttt tctcttgaac tcgacggatc tatgcggtgt   1380
gaaataccgc acagatgcgt aaggagaaaa taccgcatca ggaaattgta acgttaata   1440 ttttgttaaa attcgcgtta aattttttgtt aaatcagctc attttttaac cataggccg   1500 aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta atcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc   1980 gattaagttg ggtaacgcca gggttttccc agtcacgacg ttgtaaaacg acggccagtg   2040
agcgcgcgta atacgactca ctatagggcg aattgggtac cgggccccc ctgtacgcat   2100 gtaacattat actgaaaacc ttgcttgaga aggttttggg acgctcgaag gctttaattt   2160
cctgcaggaa ttaccgtcgc tcgtgatttg tttgcaaaaa gaacaaaact gaaaaaccc   2220 agacacgctc gacttcctgt cttcctattg attgcagctt ccaatttcgt cacacaacaa   2280
ggtcctgtcg acgcctactt ggcttcacat acgttgcata cgtcgatata gataataatg   2340
ataatgacag caggattatc gtaatacgta atagttgaaa atctcaaaaa tgtgtgggtc   2400
attacgtaaa taatgatagg aatgggattc ttctattttt ccttttttcca ttctagcagc   2460 cgtcgggaaa acgtggcatc ctctcttttcg ggctcaattg gagtcacgct gccgtgagca   2520
tcctctcttt ccatatctaa caactgagca cgtaaccaat ggaaaagcat gagcttagcg   2580
ttgctccaaa aaagtattgg atggttaata ccatttgtct gttctcttct gactttgact   2640
cctcaaaaaa aaaaatcta caatcaacag atcgcttcaa ttacgccctc acaaaaactt   2700
ttttccttct tcttcgccca cgttaaattt tatccctcat gttgtctaac ggatttctgc   2760
acttgattta ttataaaaag acaaagacat aatacttctc tatcaatttc agttattgtt   2820
cttccttgcg ttattcttct gttcttcttt tcttttgtc atatataacc ataaccaagt   2880
aatacatatt caagttttaaa catgtatacc gtaggacagt acttggtaga tagactagaa   2940
gagattggta tcgataaggt tttcggtgtg ccaggggatt acaatttgac ttttctagat   3000
tacattcaaa atcacgaagg actttcctgg caagggaata ctaatgaact aaacgcagca   3060
tatgcagcag atggctacgc ccgtgaaaga ggcgtatcag ctcttgttac tacattcgga   3120
gtgggtgaac tgtcagccat taacggaaca gctggtagtt ttgcagaaca agtccctgtc   3180
atccacatcg tgggttctcc aactatgaat gtgcaatcca acaaaaagct ggttcatcat   3240
tccttaggaa tgggtaactt tcataacttt agtgaaatgg ctaaggaagt cactgccgct   3300
acaaccatgc ttactgaaga gaatgcagct tcagagatcg acagagtatt agaaacagcc   3360
ttgttggaaa agaggccagt atacatcaat cttccaattg atatagctca taagcaata   3420
```

-continued

```
gttaaacctg caaaagcact acaaacagag aaatcatctg gtgagagaga ggcacaactt    3480
gcagaaatca tactatcaca cttagaaaag gccgctcaac ctatcgtaat cgccggtcat    3540
gagatcgccc gtttccagat aagagaaaga tttgaaaact ggataaacca aacaaagttg    3600
ccagtaacca atttggcata tggcaaaggc tctttcaatg aagagaacga acatttcatt    3660
ggtacctatt acccagcttt ttctgacaaa aacgttctgg attacgttga caatagtgac    3720
ttcgttttac attttggtgg gaaaatcatt gacaattcta cctcctcatt ttctcaaggc    3780
tttaagactg aaaacacttt aaccgctgca aatgacatca ttatgctgcc agatgggtct    3840
acttactctg ggatttctct taacggtctt ttggcagagc tggaaaaact aaactttact    3900
tttgctgata ctgctgctaa acaagctgaa ttagctgttt tcgaaccaca ggccgaaaca    3960
ccactaaagc aagacagatt tcaccaagct gttatgaact ttttgcaagc tgatgatgtg    4020
ttggtcactg agcaggggac atcatctttc ggtttgatgt tggcacctct gaaaaagggt    4080
atgaatttga tcagtcaaac attatggggc tccataggat acacattacc tgctatgatt    4140
ggttcacaaa ttgctgcccc agaaaggaga cacattctat ccatcggtga tggatctttt    4200
caactgacag cacaggaaat gtccaccatc ttcagagaga aattgacacc agtgatattc    4260
attatcaata cgatggcta tacagtcgaa agagccatcc atggagagga tgagagttac    4320
aatgatatac caacttggaa cttgcaatta gttgctgaaa catttggtgg tgatgccgaa    4380
actgtcgaca ctcacaacgt tttcacagaa acagacttcg ctaatacttt agctgctatc    4440
gatgctactc ctcaaaaagc acatgtcgtt gaagttcata tggaacaaat ggatatgcca    4500
gaatcattga gacagattgg cttagcctta tctaagcaaa actcttaacc tgcagggccg    4560
tgaatttact ttaaatcttg catttaaata aattttcttt ttatagcttt atgacttagt    4620
ttcaatttat atactatttt aatgacattt tcgattcatt gattgaaagc tttgtgtttt    4680
ttcttgatgc gctattgcat tgttcttgtc ttttcgcca catgtaatat ctgtagtaga    4740
tacctgatac attgtggatg ctgagtgaaa ttttagttaa taatggaggc gctcttaata    4800
attttgggga tattggcttt tttttttaaa gtttacaaat gaatttttc cgccaggata    4860
acgattctga agttactctt agcgttccta tcggtacagc catcaaatca tgcctataaa    4920
tcatgcctat atttgcgtgc agtcagtatc atctacatga aaaaaactcc cgcaatttct    4980
tatagaatac gttgaaaatt aaatgtacgc gccaagataa gataacatat atctagatgc    5040
agtaatatac acagattccc gcggacgtgg gaaggaaaaa attagataac aaaatctgag    5100
tgatatggaa attccgctgt atagctcata tctttcccta cctggtaaaa cctctagtgg    5160
agtagtagat gtaatcaatg aagcggaagc caaaagacca gagtagaggc ctatagaaga    5220
aactgcgata ccttttgtga tggctaaaca aacagacatc ttttatatg ttttacttc    5280
tgtatatcgt gaagtagtaa gtgataagcg aatttggcta agaacgttgt aagtgaacaa    5340
gggacctctt ttgcctttca aaaaggatt aaatggagtt aatcattgag atttagtttt    5400
cgttagattc tgtatcccta ataactccc ttacccgacg ggaaggcaca aaagacttga    5460
ataatagcaa acggccagta gccaagacca ataatacta gagttaactg atggtcttaa    5520
acaggcatta cgtggtgaac tccaagacca atatacaaaa tatcgataag ttattcttgc    5580
ccaccaattt aaggagccta catcaggaca gtagtaccat tcctcagaga agaggtatac    5640
ataacaagaa aatcgcgtga acaccttata taacttagcc cgttattgag ctaaaaaacc    5700
ttgcaaaatt tccatgaat aagaatactt cagacgtgat aaaaatttac tttctaactc    5760
ttctcacgct gccctatct gttcttccgc tctaccgtga gaaataaagc atcgagtacg    5820
```

```
gcagttcgct gtcactgaac taaaacaata aggctagttc gaatgatgaa cttgcttgct    5880
gtcaaacttc tgagttgccg ctgatgtgac actgtgacaa taaattcaaa ccggttatag    5940
cggtctcctc cggtaccggt tctgccacct ccaatagagc tcccgcacgc cgaaatgcat    6000
gcaagtaacc tattcaaagt aatatctcat acatgtttca tgagggtaac aacatgcgac    6060
tgggtgagca tatgttccgc tgatgtgatg tgcaagataa acaagcaagg cagaaactaa    6120
cttcttcttc atgtaataaa cacaccccgc gtttatttac ctatctctaa acttcaacac    6180
cttatatcat aactaatatt tcttgagata agcacactgc acccatacct tccttaaaaa    6240
cgtagcttcc agttttggt ggttccggct tccttcccga ttccgcccgc taaacgcata    6300
tttttgttgc ctggtggcat ttgcaaaatg cataacctat gcatttaaaa gattatgtat    6360
gctcttctga cttttcgtgt gatgaggctc gtggaaaaaa tgaataattt atgaatttga    6420
gaacaatttt gtgttgttac ggtattttac tatggaataa tcaatcaatt gaggatttta    6480
tgcaaatatc gtttgaatat ttttccgacc ctttgagtac ttttcttcat aattgcataa    6540
tattgtccgc tgccccttt tctgttagac ggtgtcttga tctacttgct atcgttcaac    6600
accaccttat tttctaacta tttttttttt agctcatttg aatcagctta tggtgatggc    6660 acattttgc ataaacctag ctgtcctcgt tgaacatagg aaaaaaaat atataaacaa    6720 ggctctttca ctctccttgc aatcagattt gggtttgttc cctttatttt catatttctt    6780
gtcatattcc tttctcaatt attattttct actcataacc tcacgcaaaa taacacagtc    6840
aaatcaatca aaatgaaagc attagtgtat aggggcccag gccagaagtt ggtggaagag    6900
agacagaagc cagagcttaa ggaacctggt gacgctatag tgaaggtaac aaagactaca    6960
atttgcggaa ccgatctaca cattcttaaa ggtgacgttg cgacttgtaa acccggtcgt    7020
gtattagggc atgaaggagt gggggttatt gaatcagtcg gatctggggt tactgctttc    7080
caaccaggcg atagagtttt gatatcatgt atatcgagtt gcggaaagtg ctcattttgt    7140
agaagaggaa tgttcagtca ctgtacgacc gggggttgga ttctgggcaa cgaaattgat    7200
ggtacccaag cagagtacgt aagagtacca catgctgaca catcccttta tcgtattccg    7260
gcaggtgcgg atgaagaggc cttagtcatg ttatcagata ttctaccaac gggttttgag    7320
tgcggagtcc taaacggcaa agtcgcacct ggttcttcgg tggctatagt aggtgctggt    7380
cccgttggtt tggccgcctt actgacagca caattctact ccccagctga atcataatg    7440 atcgatcttg atgataacag gctgggatta gccaaacaat ttggtgccac cagaacagta    7500
aactccacgg gtgtaacgc cgcagccgaa gtgaaagctc ttactgaagg cttaggtgtt    7560
gatactgcga ttgaagcagt tgggatacct gctacatttg aattgtgtca gaatatcgta    7620
gctcccggtg gaactatcgc taatgtcggc gttcacggta gcaaagttga tttgcatctt    7680
gaaagtttat ggtcccataa tgtcacgatt actacaaggt tggttgacac ggctaccacc    7740
ccgatgttac tgaaaactgt tcaaagtcac aagctagatc catctagatt gataacacat    7800
agattcagcc tggaccagat cttggacgca tatgaaactt ttggccaagc tgcgtctact    7860
caagcactaa aagtcatcat ttcgatggag gcttgattaa ttaagagtaa gcgaatttct    7920 tatgattat gattttatt attaaataag ttataaaaa ataagtgta tacaaatttt    7980 aaagtgactc ttaggtttta aaacgaaaat tcttattctt gagtaactct ttcctgtagg    8040
tcaggttgct ttctcaggta tagcatgagg tcgctcttat tgaccacacc tctaccggca    8100
tgccgagcaa atgcctgcaa atcgctcccc atttcaccca attgtagata tgctaactcc    8160
```

| | |
|---|---|
| agcaatgagt tgatgaatct cggtgtgtat tttatgtcct cagaggacaa cacctgtggt | 8220 |
| gagctccagc ttttgttccc tttagtgagg gttaattgcg cgcttggcgt aatcatggtc | 8280 |
| atagctgttt cctgtgtgaa attgttatcc gctcacaatt ccacacaaca taggagccgg | 8340 |
| aagcataaag tgtaaagcct ggggtgccta atgagtgagg taactcacat taattgcgtt | 8400 |
| gcgctcactg cccgctttcc agtcgggaaa cctgtcgtgc cagctgcatt aatgaatcgg | 8460 |
| ccaacgcgcg gggagaggcg gtttgcgtat tgggcgctct tccgcttcct cgctcactga | 8520 |
| ctcgctgcgc tcggtcgttc ggctgcggcg agcggtatca gctcactcaa aggcggtaat | 8580 |
| acggttatcc acagaatcag gggataacgc aggaaagaac atgtgagcaa aaggccagca | 8640 |
| aaaggccagg aaccgtaaaa aggccgcgtt gctggcgttt ttccataggc tccgcccccc | 8700 |
| tgacgagcat cacaaaaatc gacgctcaag tcagaggtgg cgaaacccga caggactata | 8760 |
| aagataccag gcgtttcccc ctggaagctc cctcgtgcgc tctcctgttc cgaccctgcc | 8820 |
| gcttaccgga tacctgtccg cctttctccc ttcgggaagc gtggcgcttt ctcatagctc | 8880 |
| acgctgtagg tatctcagtt cggtgtaggt cgttcgctcc aagctgggct gtgtgcacga | 8940 |
| accccccgtt cagcccgacc gctgcgcctt atccggtaac tatcgtcttg agtccaaccc | 9000 |
| ggtaagacac gacttatcgc cactggcagc agccactggt aacaggatta gcagagcgag | 9060 |
| gtatgtaggc ggtgctacag agttcttgaa gtggtggcct aactacggct acactagaag | 9120 |
| gacagtattt ggtatctgcg ctctgctgaa gccagttacc ttcggaaaaa gagttggtag | 9180 |
| ctcttgatcc ggcaaacaaa ccaccgctgg tagcggtggt ttttttgttt gcaagcagca | 9240 |
| gattacgcgc agaaaaaaag gatctcaaga agatcctttg atcttttcta cggggtctga | 9300 |
| cgctcagtgg aacgaaaact cacgttaagg gattttggtc atgagattat caaaaaggat | 9360 |
| cttcacctag atccttttaa attaaaaatg aagttttaaa tcaatctaaa gtatatatga | 9420 |
| gtaaacttgg tctgacagtt accaatgctt aatcagtgag gcacctatct cagcgatctg | 9480 |
| tctatttcgt tcatccatag ttgcctgact ccccgtcgtg tagataacta cgatacggga | 9540 |
| gggcttacca tctggcccca gtgctgcaat gataccgcga acccacgct caccggctcc | 9600 |
| agatttatca gcaataaacc agccagccgg aagggccgag cgcagaagtg gtcctgcaac | 9660 |
| tttatccgcc tccatccagt ctattaattg ttgccgggaa gctagagtaa gtagttcgcc | 9720 |
| agttaatagt ttgcgcaacg ttgttgccat tgctacaggc atcgtggtgt cacgctcgtc | 9780 |
| gtttggtatg gcttcattca gctccggttc ccaacgatca aggcgagtta catgatcccc | 9840 |
| catgttgtgc aaaaaagcgg ttagctcctt cggtcctccg atcgttgtca gaagtaagtt | 9900 |
| ggccgcagtg ttatcactca tggttatggc agcactgcat aattctctta ctgtcatgcc | 9960 |
| atccgtaaga tgcttttctg tgactggtga gtactcaacc aagtcattct gagaatagtg | 10020 |
| tatgcggcga ccgagttgct cttgcccggc gtcaatacgg gataataccg cgccacatag | 10080 |
| cagaacttta aaagtgctca tcattggaaa acgttcttcg gggcgaaaac tctcaaggat | 10140 |
| cttaccgctg ttgagatcca gttcgatgta acccactcgt gcacccaact gatcttcagc | 10200 |
| atcttttact ttcaccagcg tttctgggtg agcaaaaaca ggaaggcaaa atgccgcaaa | 10260 |
| aaagggaata agggcgacac ggaaatgttg aatactcata ctcttccttt ttcaatatta | 10320 |
| ttgaagcatt tatcagggtt attgtctcat gagcggatac atatttgaat gtatttagaa | 10380 |
| aaataaacaa ataggggttc cgcgcacatt tccccgaaaa gtgccacctg gtcctttttc | 10440 |
| atcacgtgct ataaaaataa ttataattta aattttttaa tataaatata aaattaaaa | 10500 |
| atagaaagta aaaaaagaaa ttaaagaaaa aatagttttt gttttccgaa gatgtaaaag | 10560 |

```
actctagggg gatcgccaac aaatactacc ttttatcttg ctcttcctgc tctcaggtat    10620
taatgccgaa ttgtttcatc ttgtctgtgt agaagaccac acacgaaaat cctgtgattt    10680
tacattttac ttatcgttaa tcgaatgtat atctatttaa tctgcttttc ttgtctaata    10740
aatatatatg taaagtacgc tttttgttga aatttttttaa acctttgttt attttttttt   10800
cttcattccg taactcttct accttcttta tttactttct aaaatccaaa tacaaaacat    10860
aaaaataaat aaacacagag taaattccca aattattcca tcattaaaag atacgaggcg    10920
cgtgtaagtt acaggcaagc gatccgtcct aagaaaccat tattatcatg acattaacct    10980
ataaaaatag gcgtatcacg aggcccttc gtc                                  11013
```

PARTIAL ADAPTATION FOR BUTANOL PRODUCTION

CROSS REFERENCE TO RELATED APPLICATION

This application claims benefit of priority from U.S. Provisional Application No. 61/842,817, filed Jul. 3, 2013, which is hereby incorporated by reference in its entirety.

REFERENCE TO SEQUENCE LISTING SUBMITTED ELECTRONICALLY

The content of the electronically submitted sequence listing in ASCII text file (Name: 20140701_CL6041USNP_SeqList_ST25; Size 140,188 bytes, and Date of Creation: Jun. 23, 2014) filed with the application is incorporated herein by reference in its entirety.

FIELD OF THE INVENTION

The invention relates to the field of industrial microbiology and the fermentative production of butanol and isomers thereof. More specifically, the invention relates to processes to produce improved cell cultures in order to maximize biomass production, minimize timing of the propagation and production phases of fermentation, and achieve economical production or butanol and isomers thereof.

BACKGROUND

Butanol is an important industrial chemical, useful as a fuel additive, as a feedstock chemical in the plastics industry, and as a food grade extractant in the food and flavor industry. Accordingly, there is a high demand for butanol, as well as for efficient production methods. One production method which has the potential to reduce environmental impact includes the production of butanol utilizing fermentation by recombinant microorganisms.

Maximum butanol production will require optimization of the recombinant microorganism comprising a butanol biosynthetic pathway and optimization of the process by which butanol is produced. Growth of the recombinant microorganism in different stages of the process is critical for the butanol process. The three phases (e.g., (1) the growth phase, (2) the propagation phase, and (3) the production phase) of the process have different operating conditions, which results in different physiological states for the recombinant microorganism. Pathway leakage and accumulation of inhibitory intermediates can limit growth rate and limit maximum cell density achieved at each stage. An intricate combination of genetic and process solutions to achieve the desired overall volumetric productivities would represent an advance in the art.

BRIEF SUMMARY OF THE INVENTION

Provided herein are processes to produce improved cell cultures in order to maximize biomass production, minimize timing of the propagation and production phases of fermentation, and achieve economical production of butanol and isomers thereof.

Provided herein are processes for producing an improved culture of cells comprising an engineered butanol biosynthetic pathway. The processes comprise (a) providing a cell culture of recombinant microorganisms comprising an engineered butanol biosynthetic pathway, wherein said engineered butanol biosynthetic pathway is minimally or not activated; and (b) growing the culture of recombinant microorganisms under adaptive conditions whereby pathway activation is increased to produce an improved cell culture and whereby said improved cell culture is capable of continuing to grow in fermentation. In certain embodiments the fermentation can comprise a propagation phase and a production phase.

In certain embodiments, the improved cell culture is characterized by at least one of an increase in biomass production in the propagation phase, an increase in biomass production in the production phase, a reduction in the amount of time in the propagation phase, reduction in the amount of time in the production phase, an increase in butanol yield, an increase in butanol productivity, an increase in biomass yield, a reduction or elimination of production of a inhibitory products in the propagation phase, a delay in the production of a inhibitory products in the production phase.

In certain embodiments, the adaptive conditions comprise at least one of a source of carbon substrate, a dissolved oxygen concentration, a temperature, a pH, a carbon substrate (e.g., glucose) concentration, a butanol concentration, a butanol metabolite concentration, a 2-butanone concentration, or an added component to the fermentation media (e.g., a biochemical or chemical activator). The adaptive conditions can comprise a carbon substrate concentration (e.g., glucose concentration) and a dissolved oxygen concentration.

Also provided herein are processes for the production of a partially adapted cell culture. The processes comprise (a) providing a cell culture of recombinant microorganisms comprising an engineered butanol biosynthetic pathway, wherein the culture has a maximum $q_p$, wherein production of butanol via the engineered butanol biosynthetic pathway is affected by adaptive conditions, and wherein the culture is provided at a $q_p$ at least about 0.01% of the maximum $q_p$, and (b) growing the culture in a propagation phase of a fermentation process, wherein the propagation phase is characterized by a first set adaptive conditions, and wherein the culture grows for at least one generation such that the $q_p$ increases to at least 20% of the maximum $q_p$, whereby a partially adapted cell culture is produced. Optionally, the processes further comprise (c) providing the partially adapted cell culture in a production phase of a fermentation process, wherein the production phase is characterized by a second set of adaptive conditions, and wherein the $q_p$ of the partially adapted cell culture increases to at least about 50% of the maximum $q_p$.

In certain embodiments, the processes comprise (a) providing a cell culture of recombinant microorganisms comprising an engineered butanol biosynthetic pathway, wherein the culture has a maximum $q_p$, wherein production of butanol via the engineered butanol biosynthetic pathway is affected by adaptive conditions, and wherein the culture is provided at a $q_p$ at least about 0.01% of the maximum $q_p$; (b) growing the culture in a propagation phase of a fermentation process, wherein the propagation phase is characterized by a first set of adaptive conditions, and wherein the culture grows for at least two generations such that the $q_p$ increases to at least 20% of the maximum $q_p$, whereby a partially adapted cell culture is produced; and (c) providing the partially adapted cell culture in a production phase of a fermentation process, wherein the production phase is characterized by a second set of adaptive conditions, and wherein the $q_p$ of the partially adapted cell culture increases to at least about 50% of the maximum $q_p$.

In certain embodiments, the processes comprise (a) providing a cell culture of recombinant microorganisms comprising an engineered butanol biosynthetic pathway, wherein the culture has a maximum $q_p$, wherein production of butanol via the engineered butanol biosynthetic pathway is affected by adaptive conditions, and wherein the culture is provided at a $q_p$ at least about 0.01% of the maximum $q_p$; (b) growing the culture in a propagation phase of a fermentation process, wherein the propagation phase is characterized by a first set of adaptive conditions, and wherein the culture grows for at least two generations such that the $q_p$ increases to at least 20% of the maximum $q_p$, whereby a partially adapted cell culture is produced; and (c) growing the partially adapted cell culture in a production phase of a fermentation process, wherein the production phase is characterized by a second set of adaptive conditions, and wherein the culture grows for at least two generations such that the $q_p$ of the partially adapted cell culture increases to at least about 50% of the maximum $q_p$.

In certain embodiments, the processes comprise (a) providing a cell culture of recombinant microorganisms comprising an engineered isobutanol biosynthetic pathway, wherein the culture has a maximum $q_p$, wherein production of isobutanol via the engineered isobutanol biosynthetic pathway is affected by adaptive conditions, and wherein the culture is provided at a $q_p$ at least about 0.01% of the maximum $q_p$; (b) growing the culture in a propagation phase of a fermentation process, wherein the propagation phase is characterized by a first set of adaptive conditions, and wherein the culture grows for at least one generation such that the $q_p$ increases to at least 20% of the maximum $q_p$, whereby a partially adapted cell culture is produced; and (c) growing the partially adapted cell culture in a production phase of a fermentation process, wherein the production phase is characterized by a second set of adaptive conditions, and wherein the culture grows for at least one generation such that the $q_p$ of the partially adapted cell culture increases to at least about 50% of the maximum $q_p$; wherein the culture produces isobutanol, and optionally, wherein the isobutanol is recovered.

In certain embodiments, the culture is provided at a cell density of at least about 0.1 g/L. Optionally, the culture is provided at a cell density of at least about 0.5 g/L; at least about 1 g/L; or at least about 2 g/L.

In certain embodiments, the minimally activated culture is provided at a $q_p$ of at least about 0.01% to about 10% of the maximum $q_p$; at least about 0.01% to about 5% of the maximum $q_p$; at least about 0.01% to about 1% of the maximum $q_p$, or any value in between.

In certain embodiments, the minimally activated culture is provided at a $q_p$ of about 0.01 grams per gram of dry cell weight per hour (g/g dcw/hr) to about 0.1 g/g dcw/hr; a $q_p$ of about 0.01 g/g dcw/hr to about 0.08 g/g dcw/hr; a $q_p$ of about 0.01 g/g dcw/hr to about 0.05 g/g dcw/hr; a $q_p$ of about 0.01 g/g dcw/hr to about 0.03 g/g dcw/hr; a $q_p$ of about 0.02 g/g dcw/hr to about 0.08 g/g dcw/hr; a $q_p$ of about 0.02 g/g dcw/hr to about 0.04 g/g dcw/hr; a $q_p$ of about 0.04 g/g dcw/hr to about 0.08 g/g dcw/hr; a $q_p$ of about 0.05 g/g dcw/hr to about 0.10 g/g dcw/hr, or any value in between. Optionally, the minimally activated culture is provided at a $q_p$ of at least about 0.01 g/g dcw/hr, at least about 0.05 g/g dcw/hr, or at least about 0.10 g/g dcw/hr.

In certain embodiments, the inactivated culture is provided at a $q_p$ of about 0.0 g/g dcw/hr.

In certain embodiments, growing the culture under adaptive conditions increases pathway activation to produce an improved cell culture such that the $q_p$ increases to about 20% to about 50% of the maximum $q_p$; about 20% to about 40% of the maximum $q_p$; about 20% to about 30% of the maximum $q_p$, or any value in between. In certain embodiments, growing the culture under adaptive conditions increases the pathway activation to produce an improved cell culture such that the $q_p$ increases to at least about 20% of the maximum $q_p$; at least about 30% of the maximum $q_p$; at least about 40% of the maximum $q_p$; or at least about 50% of the maximum $q_p$. In certain embodiments, the $q_p$ increases to these levels in the propagation phase.

In certain embodiments, growing the culture under adaptive conditions increases pathway activation to produce an improved cell culture such that the $q_p$ increases to about 0.10 g/g dcw/hr to about 0.50 g/g dcw/hr; about 0.20 g/g dcw/hr to about 0.50 g/g dcw/hr; about 0.20 g/g dcw/hr to about 0.40 g/g dcw/hr; about 0.20 g/g dcw/hr to about 0.30 g/g dcw/hr; about 0.30 g/g dcw/hr to about 0.50 g/g dcw/hr; about 0.40 g/g dcw/hr to about 0.50 g/g dcw/hr, or any value in between. In certain embodiments, growing the culture under adaptive conditions increases pathway activation to produce an improved cell culture such that the $q_p$ increases to at least about 0.10 g/g dcw/hr; at least about 0.20 g/g dcw/hr; at least about 0.30 g/g dcw/hr; at least about 0.40 g/g dcw/hr; or at least about 0.50 g/g dcw/hr. In certain embodiments, the qp increases in the propagation phase.

In certain embodiments, growing the culture under adaptive conditions increases pathway activation to produce an improved cell culture such that the $q_p$ increases to at least about 50% of the maximum $q_p$; at least about 75% of the maximum $q_p$; at least about 90% of the maximum $q_p$. In certain embodiments, the $q_p$ increases to these levels in the production phase.

In certain embodiments, growing the culture under adaptive conditions increases pathway activation to produce an improved cell culture such that the $q_p$ increases to at least about 0.50 g/gdcw/hr; at least about 0.60 g/g dcw/hr; at least about 0.70 g/g dcw/hr; at least about 0.80 g/g dcw/hr; or at least about 0.85 g/g dcw/hr. In certain embodiments, the $q_p$ increases to these levels in the production phase.

In certain embodiments, the culture grows for at least one generation; at least two generations; at least three generations; at least five generations; or at least eight generations. Optionally, the culture grows for at least two to at least eight generations, at least two to at least six generations, or at least two to at least four generations. In certain embodiments the culture is capable of growing in propagation phase, the production phase, or both the propagation and the production phase.

In certain embodiments, growing the culture under adaptive conditions increases the biomass production of the culture to a cell density of about 5 g/L to about 15 g/L; about 5 g/L to about 10 g/L; about 8 g/L to about 10 g/L, or any value in between.

In certain embodiments, the improved culture results in a reduction or elimination of an inhibitory product or a delay in the accumulation of an inhibitory product. The reduction or elimination of the inhibitory product can occur in the propagation phase. Optionally the inhibitory product is butanol. In certain embodiments, the improved cell culture comprises a butanol concentration of about 0 g/L to about 10 g/L; about 0 g/L to about 5 g/L; or about 2 g/L to about 5 g/L, or any value in between, in the propagation phase. The delay in accumulation of the inhibitory product can, for example, occur in the production phase. Optionally, the butanol concentration is at least about 25 g/L in the production phase. Optionally, the butanol concentration is about 25 g/L to about 200 g/L or any value in between. In certain embodiments, the inhibitory product is isobutyric acid. Optionally, the isobutyric acid concentration is about 0 g/L to about 2.5 g/L; about 0 g/L to about 1 g/L; or about 1 g/L to about 2 g/L, or in any value in between.

The recombinant microorganism can comprise a butanol biosynthetic pathway selected from the group consisting of (a) a 1-butanol biosynthetic pathway; (b) a 2-butanol biosynthetic pathway; and (c) an isobutanol biosynthetic pathway.

In certain embodiments, the recombinant microorganism is from a genus selected from the group consisting of *Clostridium, Zymomonas, Escherichia, Salmonella, Serratia, Erwinia, Klebsiella, Shigella, Rhodococcus, Pseudomonas, Bacillus, Lactobacillus, Lactococcus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma*, and *Saccharomyces*.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further define this invention, the following terms, abbreviations and definitions are provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the claims as presented or as later amended and supplemented, or in the specification.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, or within 5% of the reported numerical value.

The term "minimally activated" as used herein refers to a level of activation of the engineered butanol biosynthetic pathway in which there is a minimal rate of butanol production (e.g., less than about 0.01, 0.02, 0.03, 0.04, 0.05, 0.06, 0.07, 0.08, 0.09, 0.10, or 0.20 grams of butanol per gram of dry cell weight of cells per hour (g/g dcw/hr)) by the culture of the recombinant microorganism and/or a level of activation of the engineered butanol biosynthetic pathway in which the $q_p$ of the cell culture is at least about 0.01% to at least about 10% of the maximum $q_p$ of the culture, or any interval therein. The $q_p$ of the cell culture can, for example, be about 0.01 g/g dcw/hr to about 0.10 g/g dcw/hr.

The term "inactivated" as used herein refers to a level of activation of the engineered butanol biosynthetic pathway in which there is no measurable rate of butanol production by the recombinant microorganism and/or a level of activation of the engineered butanol biosynthetic pathway in which the $q_p$ of the cell culture is about 0 g/g dcw/hr.

The term "increased activation" as used herein refers to any increase in cell culture activation at any time point in the fermentation process as compared to a previous time point in the fermentation process. By way of an example, increased activation can refer to an increase in cell culture activation above a minimally activated or inactivated cell culture where the culture of recombinant microorganisms achieves an increased rate of butanol production above a minimally activated or inactivated culture butanol production rate. For example, an increased activation of a minimally activated recombinant microorganism culture having a minimal rate of butanol production and/or having a $q_p$ of about 0.01% of the maximum $q_p$ of the recombinant microorganism can result in a recombinant microorganism culture with an increased rate of butanol production in comparison to the minimally activated culture and/or having a $q_p$ of at least about 20% of the maximum $q_p$ of culture. Increased activation can also be determined by calculating an activation ratio for the culture. Increased activation can be measured by methods known in the art, including, but not limited to, measuring an increase in the expression of an enzyme of the engineered butanol biosynthetic pathway, measuring an increase in the activity of an enzyme of the engineered butanol biosynthetic pathway, measuring an increase in the amount of butanol produced in the fermentation process, and/or measuring an increase in the amount of a byproduct (e.g., isobutyric acid) or other pathway metabolites produced in the fermentation process.

The term "activation ratio" as used herein, in certain embodiments, refers to a ratio of the $q_p$ of the cell culture at any given time point in the fermentation as compared to the $q_p$ of a cell culture at any previous time point in the fermentation. An activation ratio greater than 1 indicates that the culture has increased activation of the engineered butanol biosynthetic pathway. By way of an example, a minimally activated cell culture comprising a $q_p$ of 0.01 g/g dcw/hr provided at the beginning of a fermentation and grown under adaptive conditions can increase activation to a $q_p$ 0.20 g/g dcw/hr during the fermentation process. The cell culture has an activation ratio of 20. In other embodiments, activation ratio can refer to a ratio of the $q_p$ of the cell culture at any given time point in the fermentation as compared to the $q_p$ of a cell culture at any previous time point in the fermentation. In other embodiments, activation ratio can refer to a ratio of expression of an enzyme (e.g., acetolactate synthase) at any given time point in the fermentation as compared to the expression of the enzyme at any previous time point in the fermentation. Activation ratios can be calculated by methods known in the art, including, but not limited to, measuring an increase in the expression of an enzyme of the engineered butanol biosynthetic pathway, measuring an increase in the activity of an enzyme of the engineered butanol biosynthetic pathway, measuring an increase in the amount of butanol produced in the fermentation process, and/or measuring an increase in the amount of a byproduct (e.g., isobutyric acid) or other pathway metabolites produced in the fermentation process.

The term "adaptive conditions" as used herein refers to process conditions whereby the engineered butanol biosynthetic pathway is differentially activated. Adaptive conditions can, for example, refer to process conditions, e.g., which can include conditions during growth, culture, production, propagation, and/or fermentation, or other processes with suitable conditions for such processes that allow for changes in the level of adaptation of the recombinant microorganism. Adaptation includes increases in activation as described herein. Adaptive conditions may promote the change from a minimally activated or inactivated culture or recombinant microorganisms to a partially or fully adapted culture. Levels of adaptation can, for example, be determined by comparing the $q_p$ of the culture to the maximum $q_p$ for the culture. Alternatively, levels of adaptation can be determined by comparing the $q_p$ of the culture at different time points during the growth of the culture. An increase in $q_p$ can indicate an increase in the level of adaptation of the culture. Alternatively, levels of adaptation of the recombinant microorganism can, for example, be determined by measuring the level of expression of an enzyme of the engineered butanol biosynthetic pathway, measuring the activity of an enzyme of the engineered butanol biosynthetic pathway, measuring the amount of butanol produced by the recombinant microorganism, and/or measuring an increase in the amount of a byproduct produced by the recombinant microorganism. Examples of process conditions that can result in changes in the level of adaptation of the recombinant microorganism can include, but are not limited to, the source of the carbon substrate, a dissolved oxygen concentration, a temperature, a pH, a substrate (e.g., glucose) concentration, an added component to the fermentation media (e.g., a biochemical or chemical activator), a butanol concentration, a butanol metabolite concentration, or a 2-butanone concentration.

The term "cell culture" or "culture" as used herein refers to a population of recombinant microorganisms that can be provided at the start of a cell production process. The cell culture can be produced by methods known in the art, including, but not limited to, a seed population produced from a stock vial of the recombinant microorganism, a population produced from a solid media substrate (e.g., an agar plate or agar slant), a flask culture produced from a stock culture of the recombinant microorganism, a cell population of recombinant microorganism derived from one or more fermentor vessels (e.g., batch, fed-batch, or continuous fermentation configurations), a dried population of the recombinant microorganism (e.g., an active dry yeast), a semi-dried population of the recombinant microorganism (e.g., a yeast cream and/or a yeast cake).

The term "improved culture" as used herein refers to a culture that is produced by growing the recombinant microorganism under adaptive conditions that allow for process improvements. Examples of process improvements can include but are not limited to, an increase in biomass production of the recombinant microorganism in the propagation and/or production phase, an increase in biomass yield in the propagation and/or production phase, a reduction in the amount of time for the propagation and/or production phase, a reduction or elimination of the production of an inhibitory product (e.g., a reduction or elimination of isobutanol, isobutyric acid, isobutyraldehyde, and/or acetic acid production) in the propagation phase, an increase in the preconditioning of culture to inhibitory products (i.e., the culture can adjust to increasing levels of isobutanol as produced in production phase), a capability for the recombinant microorganism to continue growing resulting in an increase in biomass production in the production phase, an increase in butanol yield in the production phase, an increase in butanol productivity in the production phase, and/or a delay in the production of an inhibitory product at the beginning of the production phase (e.g., a delay in the production of butanol and/or isobutyric acid). An improved culture can also allow for increased operational flexibility (e.g., increased range of amount of cells to start fermentation process, increased scheduling flexibility for coordinating fermentation process). An increase in biomass production, butanol yield, butanol productivity, biomass yield, or a decrease in the amount of time in a propagation or production phase can be determined by measuring the indicated property or characteristic in recombinant microorganism cultures grown under adaptive conditions and comparing to the indicated property or characteristic in recombinant microorganism cultures grown under non-adaptive conditions or different adaptive conditions.

The term "capable of continuing to grow" as used herein refers to an increase in cell mass during fermentation or under production phases where butanol is being produced. Recombinant microorganism cultures can, for example, be able to grow independent of the process conditions in which the recombinant microorganism is subjected. By way of an example, for the processes described herein, the recombinant microorganism can be capable of growing under adaptive conditions in the butanol production phase.

The term "propagation phase" or "growth phase" as used herein refers to the process steps during which the recombinant microorganism (e.g., yeast) biomass is produced. These phases may include minimally activated or inactivated cultures. Such phases may also include adaptive conditions under which an increased activation of the culture occurs.

The term "production phase" as used herein refers to the fermentation or other process steps during which a desired fermentation product, including, but not limited to butanol, isobutanol, 1-butanol, 2-butanol, and/or 2-butanone, is produced.

The term "biomass" as used herein, in some instances, refers to the mass of the culture, e.g., the amount of recombinant microorganisms, typically provided in units of grams per liter (g/l) dry cell weight (dcw).

The term "biomass yield" as used herein refers to the amount of biomass produced per substrate consumed.

The term "fermentation product" as used herein refers to any desired product of interest, including lower alkyl alcohols, including, but not limited to, butanol, lactic acid, 3-hydroxy-propionic acid, acrylic acid, acetic acid, succinic acid, citric acid, fumaric acid, malic acid, itaconic acid, 1,3-propane-diol, ethylene, glycerol, isobutyrate, etc.

The term "lower alkyl alcohol" as used herein refers to any straight-chain or branched, saturated or unsaturated, alcohol molecule with 1-10 carbon atoms.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butanol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "2-butanone biosynthetic pathway" refers to an enzymatic pathway to produce 2-butanone. A "2-butanone biosynthetic pathway" can refer to an enzyme pathway to produce 2-butanone from pyruvate. For example, 2-butanone biosynthetic pathways are disclosed in U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851,188, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

The term "propagation polypeptide" as used herein refers to polypeptides associated with the production of biomass, and polypeptides associated with the performance of an enzyme that is associated with the production of biomass.

The term "biocatalyst polypeptide" as used herein refers to polypeptides associated with the substrate to product conversions of an indicated biosynthetic pathway, for example, a butanol or 2-butanone biosynthetic pathway, and polypeptides associated with the propagation or performance of a biocatalyst that is associated with the indicated biosynthetic pathway, including, but not limited to, cell integrity polypeptides and propagation polypeptides. For example, a polypeptide that is a part of an NADPH generating pathway or a polypeptide that is part of a non-butanol NADH consuming product pathway may be biocatalyst polypeptides.

The term "biosynthetic pathway polypeptide" as used herein refers to polypeptides that catalyze substrate to product conversions of a recited biosynthetic pathway.

The term "cell integrity polypeptide" as used herein refers to polypeptides involved in cell integrity, including polypeptides required for constituting the cellular architecture.

The term "butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the $^{14}C/^{12}C$ isotope ratio. A $^{14}C/^{12}C$ isotope ratio in range of from 1:0 to greater than 0:1 indicates a bio-produced molecule, whereas a ratio of 0:1 indicates that the molecule is fossil derived.

A recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "heterologous biosynthetic pathway" as used herein refers to an enzyme pathway to produce a product in which at least one of the enzymes is not endogenous to the host cell containing the biosynthetic pathway.

The terms "PDC-," "PDC knockout," or "PDC-KO" as used herein refer to a cell that has a genetic modification to inactivate or reduce expression of a gene encoding pyruvate decarboxylase (PDC) so that the cell substantially or completely lacks pyruvate decarboxylase enzyme activity. If the cell has more than one expressed (active) PDC gene, then each of the active PDC genes can be inactivated or have minimal expression thereby producing a PDC-cell.

The term "effective butanol productivity" as used herein refers to the total amount in grams of butanol produced per gram of cells.

The term "effective titer" as used herein, refers to the total amount of a particular alcohol (e.g., butanol) produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of butanol produced by fermentation per liter of fermentation medium per hour of fermentation.

The term "effective yield" as used herein, refers to the amount of butanol produced per unit of fermentable carbon substrate consumed by the biocatalyst.

The term "volumetric productivity" refers to the grams of butanol isomer produced per liter of fermentation media per unit time. The terms "volumetric productivity" and "$Q_p$" can be used interchangeably.

The term "specific productivity" refers to the grams of butanol isomer produced per gram of dry cell weight of cells per unit time. The terms "specific productivity" and "$q_p$" can be used interchangeably.

The term "maximum $q_p$" or "$q_p$ max" as used herein refers to the maximum potential for a recombinant microorganism to produce a desired fermentation product per unit gram of dry cell weight (g dcw) of biomass per unit of time. A recombinant microorganism comprising an engineered butanol biosynthetic pathway can comprise a maximum $q_p$. The maximum $q_p$ for the recombinant microorganism can be calculated by methods known in the art. By way of an example, a maximum $q_p$ for a recombinant microorganism can be determined during a fermentation process under the desired set of conditions. Samples of the fermentation culture at different time points are measured for levels of product (e.g., isobutanol) produced (g/L) and levels of biomass produced (g dcw/L) using analytical methods known in the art and described herein. $q_p$ (g/g dcw/hr) at any point during the fermentation process is calculated as the net amount of product produced (g/L) during a time interval between two successive sample points divided by the average biomass level (g dcw/L) during the same time interval, and this value is divided by the time interval (h) over which the samples were taken. Calculated $q_p$ is plotted as a function of fermentation time and the maximum value is designated as maximum $q_p$.

The term "partially adapted culture" or "partially adapted cell culture" as used herein refers to a culture of recombinant microorganisms comprising an engineered butanol biosynthetic pathway, wherein the engineered butanol biosynthetic pathway is partially activated such that the $q_p$ of the culture of recombinant microorganisms is less than the maximum $q_p$ of the recombinant microorganism culture. By way of an example, the $q_p$ of a partially adapted cell culture can be about 20% of the maximum $q_p$ of the cell culture. Partial activation of the engineered butanol biosynthetic pathway can be the result of growing the recombinant microorganism culture under adaptive conditions, wherein the partial activation of the engineered butanol biosynthetic pathway can be controlled by at least one process condition. The at least one process condition can result in the differential activation of the engineered butanol biosynthetic pathway. By way of a non-limiting example, in glucose limited or glucose diluted conditions, the engineered butanol biosynthetic pathway of the cell culture can be inactivated or minimally activated, whereas in glucose excess conditions, the engineered butanol biosynthetic pathway can be completely or fully activated.

The term "growth rate" refers to the rate at which the microorganisms grow in the culture medium. The growth rate of the recombinant microorganisms can be monitored, for example, by measuring the optical density at 600 nanometers. The doubling time may be calculated from the logarithmic part of the growth curve and used as a measure of the growth rate.

The term "separation" as used herein is synonymous with "recovery" and refers to removing a chemical compound from an initial mixture to obtain the compound in greater purity or at a higher concentration than the purity or concentration of the compound in the initial mixture.

The term "extractant" as used herein refers to one or more organic solvents which can be used to extract butanol from a fermentation broth.

The term "aqueous phase," as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase," as used herein, refers to the non-aqueous phase of a biphasic mixture obtained by contacting a fermentation broth with a water-immiscible organic extractant.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. Non-limiting examples of carbon substrates are provided herein and include, but are not limited to, monosaccharides, disaccharides, oligosaccharides, polysaccharides, ethanol, lactate, succinate, glycerol, carbon dioxide, methanol, glucose, fructose, lactose, sucrose, xylose, arabinose, dextrose, cellulose, methane, amino acids, or mixtures thereof.

"Fermentation broth" as used herein means the mixture of water, sugars (fermentable carbon sources), dissolved solids (if present), microorganisms producing alcohol, product alcohol and all other constituents of the material in which product alcohol is being made by the reaction of sugars to alcohol, water and carbon dioxide ($CO_2$) by the microorganisms present. From time to time, as used herein the term "fermentation medium," "fermentation media," and "fermented mixture" can be used synonymously with "fermentation broth."

As used herein a "fermentor" refers to any container, containers, or apparatus that are used to ferment a substrate. A fermentor can contain a fermentation medium and microorganism capable of fermentation. The term "fermentation vessel" refers to the vessel in which the fermentation reaction is carried out whereby alcohol such as butanol is made from sugars. "Fermentor" can be used herein interchangeable with "fermentation vessel."

"Feedstock" as used herein means a product containing a fermentable carbon source. Suitable feedstock include, but are not limited to, rye, wheat, corn, corn mash, cane, cane mash, sugar cane, barley, cellulosic material, lignocellulosic material, and mixtures thereof.

The term "aerobic conditions" as used herein means growth conditions in the presence of oxygen.

The term "microaerobic conditions" as used herein means growth conditions with low levels of oxygen (i.e., below normal atmospheric oxygen levels). For example, the oxygen level may be less than about 1% of air-saturation.

The term "anaerobic conditions" as used herein means growth conditions in the absence of oxygen. It will be understood that in many fermentation processes, an initial amount of oxygen is present at the onset of the process, but such oxygen is depleted over the course of the fermentation such that the majority of the process takes place in the absence of detectable oxygen.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. "Polynucleotide" embraces chemically, enzymatically, or metabolically modified forms.

A polynucleotide sequence can be referred to as "isolated," in which it has been removed from its native environment. For example, a heterologous polynucleotide encoding a polypeptide or polypeptide fragment having ALS activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA can be comprised of one or more segments of cDNA, genomic DNA or synthetic DNA."

The term "isolated nucleic acid molecule", "isolated nucleic acid fragment" and "genetic construct" are used interchangeably and mean a polymer of RNA or DNA that is single or double-stranded, optionally containing synthetic, non-natural or altered nucleotide bases. An isolated nucleic acid fragment in the form of a polymer of DNA can be comprised of one or more segments of cDNA, genomic DNA or synthetic DNA.

The term "amino acid" refers to the basic chemical structural unit of a protein or polypeptide. The abbreviations in Table 1 are used herein to identify specific amino acids.

TABLE 1

Amino acids and abbreviations thereof.

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |

TABLE 1-continued

Amino acids and abbreviations thereof.

| Amino Acid | Three-Letter Abbreviation | One-Letter Abbreviation |
|---|---|---|
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a non-native microorganism, or chimeric genes. A "transgene" is a gene that has been introduced into the genome by a transformation procedure.

As used herein, "native" refers to the form of a polynucleotide, gene, or polypeptide as found in nature with its own regulatory sequences, if present.

As used herein the term "coding sequence" or "coding region" refers to a DNA sequence that encodes for a specific amino acid sequence. A "coding region" or "open reading frame (ORF)" is a portion of nucleic acid which consists of codons translated into amino acids. Although a "stop codon" (TAG, TGA, or TAA) is not translated into an amino acid, it may be considered to be part of a coding region, if present, but any flanking sequences, for example, promoters, ribosome binding sites, transcriptional terminators, introns, 5' and 3' non-translated regions, and the like, are not part of a coding region.

"Suitable regulatory sequences" as used herein refers to nucleotide sequence located upstream (5' non-coding sequences), within, or downstream (3' non-coding sequences) of a coding sequence that influence the transcription, RNA processing or stability, or translation of the associated coding sequence. Regulatory sequences can include promoters, translation leader sequences, introns, polyadenylation recognition sequences, RNA processing sites, effector binding sites, and stem-loop structures.

The term "promoter" as used herein refers to a DNA sequence capable of controlling the expression of a coding sequence or functional RNA. In general, a coding sequence located 3' to a promoter sequence. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism transcribed and translated from a native polynucleotide or gene in its natural location in the genome of an organism.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region with non-native regulatory regions that is reintroduced into the native host. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. A "heterologous" polypeptide or polynucleotide can also include an engineered polypeptide or polynucleotide that comprises a difference from the "native" polypeptide or polynucleotide, e.g., a point mutation within the endogenous polynucleotide can result in the production of a "heterologous" polypeptide. As used herein a "chimeric gene," a "foreign gene," and a "transgene," can all be examples of "heterologous" genes.

A "transgene" is a gene that has been introduced into the genome by a transformation procedure.

The term "recombinant genetic expression element" refers to a nucleic acid fragment that expresses one or more specific proteins, including regulatory sequences preceding (5' non-coding sequences) and following (3' termination sequences) coding sequences for the proteins. A chimeric gene is a recombinant genetic expression element. The coding regions of an operon can form a recombinant genetic expression element, along with an operably linked promoter and termination region.

The term "expression" as used herein refers to the transcription and stable accumulation of sense (mRNA) or antisense RNA derived from the nucleic acid fragment of the invention. Expression can also refer to translation of mRNA into a polypeptide. "Differentially expressed" as used herein refers to the differential production of the mRNA transcribed from the gene or differential production of the protein product encoded by the gene depending on the environment of the host cell. A differentially expressed gene may be overexpressed or underexpressed as compared to the expression level under other conditions. In certain aspects, differential expression refers to a differential that is 1, 2, 3, 4, 5, 10, or 20 times higher or lower than the expression level detected in the reference environment. The term "differentially expressed" also refers to nucleotide sequences in a cell which are expressed where silent or not expressed in a control environment or not expressed where expressed in the control cell.

The term "overexpression" as used herein refers to expression that is higher than endogenous expression of the same or related gene. A heterologous gene is overexpressed if its expression is higher than that of a comparable endogenous gene. The term overexpression refers to an increase in the level of nucleic acid or protein in a host cell. Thus, overexpression can result from increasing the level of transcription or translation of an endogenous sequence in a host cell or can result from the introduction of a heterologous sequence into a host cell. Overexpression can also result from increasing the stability of a nucleic acid or protein sequence.

As used herein the term "transformation" refers to the transfer of a nucleic acid fragment into the genome of a host microorganism, resulting in genetically stable inheritance. Host microorganisms containing the transformed nucleic acid fragments are referred to as "transgenic" or "recombinant" or "transformed" microorganisms.

The terms "plasmid," "vector," and "cassette" refer to an extra chromosomal element often carrying genes which are not part of the central metabolism of the cell, and usually in the form of circular double-stranded DNA fragments. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the terms "variant" and "mutant" are synonymous and refer to a polypeptide differing from a specifically recited polypeptide by one or more amino acid insertions, deletions, mutations, and substitutions, created using, e.g., recombinant DNA techniques, such as mutagenesis. Guidance in determining which amino acid residues can be replaced, added, or deleted without abolishing activities of interest, can be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

Amino acid "substitutions" can be the result of replacing one amino acid with another amino acid having similar structural and/or chemical properties, i.e., conservative amino acid replacements, or they can be the result of replacing one amino acid with an amino acid having different structural and/or chemical properties, i.e., non-conservative amino acid replacements. "Conservative" amino acid substitutions can be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in polarity, charge, solubility, hydrophobicity, hydrophilicity, or the amphipathic nature of any of these amino acids. "Insertions" or "deletions" can be within the range of variation as structurally or functionally tolerated by the recombinant proteins. The variation allowed can be experimentally determined by systematically making insertions, deletions, or substitutions of amino acids in a polypeptide molecule using recombinant DNA techniques and assaying the resulting recombinant variants for activity.

"Engineered polypeptide" as used herein refers to a polypeptide that is synthetic, i.e., differing in some manner from a polypeptide found in nature.

Alternatively, recombinant polynucleotide variants encoding these same or similar polypeptides can be synthesized or selected by making use of the "redundancy" in the genetic code. Various codon substitutions, such as silent changes which produce various restriction sites, can be introduced to optimize cloning into a plasmid or viral vector for expression. Mutations in the polynucleotide sequence can be reflected in the polypeptide or domains of other peptides added to the polypeptide to modify the properties of any part of the polypeptide. For example, mutations can be used to reduce or eliminate expression of a target protein and include, but are not limited to, deletion of the entire gene or a portion of the gene, inserting a DNA fragment into the gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less enzymatically active protein is expressed.

The terms "active variant," "active fragment," "active derivative," and "analog" refer to polynucleotides of the present invention and include any polynucleotides that encode polypeptides used in the invention that retain their respective enzymatic activities or structure. Variants of polynucleotides of the present invention include polynucleotides with altered nucleotide sequences due to base pair substitutions, deletions, and/or insertions. Variants may occur naturally or be non-naturally occurring. Non-naturally occurring variants may be produced using art-known mutagenesis techniques. Derivatives of polynucleotides of the present invention are polynucleotides which have been altered so that the polypeptides they encode exhibit additional features not found on the native polypeptide. Examples include polynucleotides that encode fusion proteins. Variant polynucleotides may also be referred to herein as "polynucleotide analogs." As used herein a "derivative" of a polynucleotide refers to a subject polynucleotide having one or more nucleotides chemically derivatized by reaction of a functional side group. Also included as "derivatives" are those polynucleotides which contain one or more naturally occurring nucleotide derivatives. For example, 3-methylcytidine may be substituted for cytosine; ribothymidine may be substituted for thymidine; and N4-acetylcytidine may be substituted for cytosine.

A "fragment" when used in reference to a promoter sequence is a unique portion of the promoter nucleic acid sequence or the nucleic acid sequence encoding the biocatalyst polypeptide used in the invention which is identical in sequence to but shorter in length than the parent nucleic acid sequence. For example, a fragment may comprise from 5 to 1000 contiguous nucleotides. A fragment used as a probe, primer, or for other purposes, may be at least 5, 10, 15, 16, 20, 25, 30, 40, 50, 60, 75, 100, 150, 250 or at least 500 contiguous nucleotides. A fragment may comprise up to the entire length of the defined sequence, minus one nucleotide or amino acid. Fragments may be preferentially selected from certain regions of a molecule. For example, a polynucleotide fragment may comprise a certain length of contiguous nucleotides selected from the first 100 or 200 nucleotides of a polynucleotide as shown in a certain defined sequence. Clearly these lengths are exemplary, and any length that is supported by the specification, including the Sequence Listing, tables, and figures, may be encompassed by the present embodiments.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein the term "codon optimized coding region" means a nucleic acid coding region that has been adapted for expression in the cells of a given organism by replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2A. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 2A

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | ACC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at the Kazusa DNA Research Institute, Japan and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 2B. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2B

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |

TABLE 2B-continued

Codon Usage Table for
Saccharomyces cerevisiae Genes

| Amino Acid | Codon | Number | Frequency per thousand |
|---|---|---|---|
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function (Entelechon GmbH, Regensburg, Germany) and the "backtranseq" function (NRC Saskatoon Bioinformatics, Saskatoon, Saskatchewan, Canada). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (University of Maryland, Baltimore, Md.).

Improved Culture of Recombinant Microorganisms

Growth of a recombinant microorganism comprising an engineered butanol biosynthetic pathway (e.g., a butanologen) can occur in different phases of a fermentation process (e.g., 1) a growth phase; 2) a propagation phase; and 3) a production phase). Growth of the butanologen is critical for the production of butanol. The three phases of the fermentation process have different operating conditions (described in Table 3), which can result in different physiological states for the butanologen. Pathway leakage and accumulation of inhibitory intermediates can limit the growth rate and the cell density of the butanologen at each phase. Intricately controlling the genetics of the butanologen and the fermentation processes can allow for increased biomass production; increased butanol yield; increased butanol productivity; increased biomass yield; increased preconditioning of the butanologen; a reduction in the amount of time for the fermentation; reduction, elimination, or delay of production of inhibitory products; and the economical production of butanol.

TABLE 3

Operating conditions of different phases of fermentation process

| | Growth Phase | Propagation Phase | Production Phase |
|---|---|---|---|
| Glucose Level | Low/High | Medium/High | High |
| Respiratory quotient (RQ) | Low | Medium | Medium/high |
| Oxygen uptake rate (OUR) | High | Medium | 0-Low |
| Pathway Intermediate Levels | Low | Medium | Medium-High |

This invention is directed to processes for producing an improved culture of cells comprising an engineered butanol biosynthetic pathway. Processes for producing an improved culture of cells comprising an engineered butanol biosynthetic pathway can comprise (a) providing a cell culture of recombinant microorganisms comprising an engineered butanol biosynthetic pathway, wherein said engineered butanol biosynthetic pathway is minimally or not activated; and (b) growing the culture of recombinant microorganisms under adaptive conditions whereby pathway activation is increased to produce an improved cell culture and whereby said improved cell culture is capable of continuing to grow in fermentation. Production of butanol via the increased activation of the engineered butanol biosynthetic pathway is affected by the adaptive conditions in which the cell culture is grown. The adaptive conditions, i.e., the process conditions, can allow for the differential activation of the butanol biosynthetic pathway, wherein the activation of the butanol biosynthetic pathway can be controlled by genetic means (e.g., promoter sequences) or non-genetic means (e.g., small molecules, chemical technology, antisense technology) such that the pathway is minimally activated or inactivated under one set of process conditions and substantially or completely activated under a second set of process conditions. Examples of controlling the expression of the butanol biosynthetic pathway can be found in U.S. application Ser. No. 13/730,742, which is hereby incorporated by reference in its entirety.

Also provided herein are processes for the production of a partially adapted cell culture. The processes comprise (a) providing a cell culture of recombinant microorganisms comprising an engineered butanol biosynthetic pathway, wherein the culture has a maximum $q_p$, wherein production of butanol via the engineered butanol biosynthetic pathway is affected by adaptive conditions, and wherein the culture is provided at a $q_p$ at least about 0.01% of the maximum $q_p$, and (b) growing the culture in a propagation phase of a fermentation process, wherein the propagation phase is characterized by a first set of adaptive conditions, and wherein the culture grows for at least one generation such that the $q_p$ increases to at least 20% of the maximum $q_p$, whereby a partially adapted cell culture is produced. Optionally, the processes further comprise (c) providing the partially adapted cell culture in a production phase of a fermentation process, wherein the production phase is characterized by a second set of adaptive conditions, and wherein the $q_p$ of the partially adapted cell culture increases to at least about 50% of the maximum $q_p$ in the production phase.

In certain embodiments, the processes comprise (a) providing a cell culture of recombinant microorganisms comprising an engineered butanol biosynthetic pathway, wherein the culture has a maximum $q_p$, wherein production of butanol via the engineered butanol biosynthetic pathway is affected by adaptive conditions, and wherein the culture is provided at a $q_p$ at least about 0.01% of the maximum $q_p$; (b) growing the culture in a propagation phase of a fermentation process, wherein the propagation phase is characterized by a first set of adaptive conditions, and wherein the culture grows for at least one generation such that the $q_p$ increases to at least 20% of the maximum $q_p$, whereby a partially adapted cell culture is produced; and (c) growing the partially adapted cell culture in a production phase of a fermentation process, wherein the production phase is characterized by a second set of adaptive conditions, and wherein the culture grows for at least one generation such that the $q_p$ of the culture increases to at least about 50% of the maximum $q_p$.

In certain embodiments the minimally activated or inactivated cell culture is provided at a cell density of at least about 0.1 g/L, at least about 0.5 g/L, at least about 1 g/L, at least about 2 g/L, at least about 4 g/L, or at least about 8 g/L. Optionally, the minimally activated or inactivated cell culture is provided at a cell density of about 0.5 g/L to about 4 g/L; about 0.5 g/L to about 3 g/L; about 0.5 g/L to about 2 g/L; about 0.5 g/L to about 1 g/L; about 1 g/L to about 4 g/L; about 1 g/L to about 3 g/L; about 1 g/L to about 2 g/L; about 2 g/L to about 4 g/L; about 2 g/L to about 3 g/L; or about 3 g/L to about 4 g/L or any value in between.

In certain embodiments, the minimally activated or inactivated cell culture is provided at a $q_p$ of about 0.01% to about 10% of the maximum $q_p$; about 0.01% to about 5% of the maximum $q_p$; about 0.01% to about 4% of the maximum $q_p$; about 0.01% to about 3% of the maximum $q_p$; about 0.01% to about 2% of the maximum $q_p$; about 0.01% to about 1% of the maximum $q_p$; about 1% to about 10% of the maximum $q_p$; about 1% to about 5% of the maximum $q_p$; about 1% to about 4% of the maximum $q_p$; about 1% to about 3% of the maximum $q_p$; about 1% to about 2% of the maximum $q_p$; about 2.5% to about 10% of the maximum $q_p$; about 2.5% to about 5% of the maximum $q_p$; or about 5% to about 10% of the maximum $q_p$, or any value in between.

In certain embodiments, the minimally activated culture is provided at a $q_p$ of about 0.01 grams per gram of dry cell weight per hour (g/g dcw/hr) to about 0.1 g/g dcw/hr; a $q_p$ of about 0.01 g/g dcw/hr to about 0.08 g/g dcw/hr; a $q_p$ of about 0.01 g/g dcw/hr to about 0.05 g/g dcw/hr; a $q_p$ of about 0.01 g/g dcw/hr to about 0.03 g/g dcw/hr; a $q_p$ of about 0.02 g/g dcw/hr to about 0.08 g/g dcw/hr; a $q_p$ of about 0.02 g/g dcw/hr to about 0.04 g/g dcw/hr; a $q_p$ of about 0.04 g/g dcw/hr to about 0.08 g/g dcw/hr; a $q_p$ of about 0.05 g/g dcw/hr to about 0.10 g/g dcw/hr, or any value in between.

In certain embodiments, the inactivated culture is provided at a $q_p$ of about 0.0 g/g dcw/hr.

In certain embodiments, growing the culture under adaptive conditions increases pathway activation to produce an improved cell culture such that the $q_p$ increases to about 20% to about 50% of the maximum $q_p$; about 20% to about 40% of the maximum $q_p$; about 20% to about 30% of the maximum $q_p$; about 30% to about 50% of the maximum $q_p$; about 30% to about 40% of the maximum $q_p$; or about 40% to about 50% of the maximum $q_p$, or any value in between. In certain embodiments, growing the culture under adaptive conditions increases the pathway activation to produce an improved cell culture such that the $q_p$ increases to at least about 20% of the maximum $q_p$; at least about 30% of the maximum $q_p$; at least about 40% of the maximum $q_p$; or at least about 50% of the maximum $q_p$. In certain embodiments, the $q_p$ increases to these levels in the propagation phase.

In certain embodiments, growing the culture under adaptive conditions increases pathway activation to produce an improved cell culture such that the $q_p$ increases to about 0.10 g/g dcw/hr to about 0.50 g/g dcw/hr; about 0.20 g/g dcw/hr to about 0.50 g/g dcw/hr; about 0.20 g/g dcw/hr to about 0.40 g/g dcw/hr; about 0.20 g/g dcw/hr to about 0.30 g/g dcw/hr; about 0.30 g/g dcw/hr to about 0.50 g/g dcw/hr; about 0.40 g/g dcw/hr to about 0.50 g/g dcw/hr, or any value in between. In certain embodiments, growing the culture under adaptive conditions increases pathway activation to produce an improved cell culture such that the $q_p$ increases to at least about 0.20 g/g dcw/hr; at least about 0.30 g/g dcw/hr; at least about 0.40 g/g dcw/hr; or at least about 0.50 g/g dcw/hr. In certain embodiments, the $q_p$ increases in the propagation phase.

In certain embodiments, the improved cell culture is characterized by at least one of an increase in biomass production, a reduction in the amount of time for the fermentation, a reduction or elimination of the production of an inhibitory product, an increase in butanol yield, an increase in butanol productivity, an increase in biomass yield, an increase in preconditioning of the recombinant microorganism, or a delay in the production of an inhibitory product.

In certain embodiments, the growing the culture under adaptive conditions to produce an improved culture increases the biomass production of the culture such that the culture is capable of growing for at least one generation, at least two generations, at least three generations, at least four generations, at least five generations, or at least six generations in the fermentation. Optionally, the culture grows for at least one generation to at least eight generations, at least one to at least six generations, at least one generation to at least four generations, at least one generation to at least two generations, at least two generations to at least six generations, at least two generations to at least four generations, or at least four generations to at least six generations in the fermentation. The culture can grow in the propagation phase, the production phase, or both the propagation and production phases.

In certain embodiments, growing the culture under adaptive conditions increases the biomass production of the culture to a cell density of about 5 g/L to about 15 g/L; about 5 g/L to about 10 g/L; about 5 g/L to about 8 g/L; about 5 g/L to about 6 g/L; or about 8 g/L to about 10 g/L, or any value in between.

The improved cell culture (e.g., a partially adapted cell culture) can be provided to a production phase of the fermentation, wherein the $q_p$ at the start of the production phase is the same as the $q_p$ at the end of the propagation phase. During the production phase, the $q_p$ of the partially adapted cell culture can increase to the maximum $q_p$ for the recombinant microorganism. In certain embodiments, the $q_p$ increases to at least about 50% of the maximum $q_p$; at least about 75% of the maximum $q_p$; at least about 80% of the maximum $q_p$; at least about 85% of the maximum $q_p$; at least about 90% of the maximum $q_p$; at least about 95% of the maximum $q_p$; or at least about 99% of the maximum $q_p$. In certain embodiments, the $q_p$ increases to these levels in the production phase.

In certain embodiments, growing the culture under adaptive conditions increases pathway activation to produce an improved cell culture such that the $q_p$ increases to at least about 0.50 g/gdcw/hr; at least about 0.60 g/g dcw/hr; at least about 0.70 g/g dcw/hr; at least about 0.80 g/g dcw/hr; or at least about 0.85 g/g dcw/hr. In certain embodiments, the $q_p$ increases to these levels in the production phase.

In certain embodiments, growing the culture under adaptive conditions results in a cell culture with an activation ratio of greater than 1; at least about 10; at least about 20; at least about 30; at least about 40; at least about 50; at least about 60; at least about 70; at least about 80; at least about 90; least about 100, or at least about 150. In certain embodiments, growing the culture under adaptive conditions results in an activation ratio of great than 1 to about 150; greater than 1 to about 50; greater than 1 to about 25; greater than 1 to about 10; about 10 to about 150; about 10 to about 100; about 10 to about 50; about 25 to about 100; about 25 to about 50; or about 50 to about 100, or any value in between.

In certain embodiments, the improved culture results in a reduction or elimination of an inhibitory product in the propagation phase or a delay in the accumulation of an inhibitory product in the production phase. Optionally the inhibitory product is butanol. Optionally, the butanol concentration in the propagation phase can be about 0 g/L to about 10 g/L; about 0 g/L to about 5 g/L; about 0 g/L to about 2.5 g/L; about 2 g/L to about 10 g/L; about 2 g/L to about 5 g/L; about 4 g/L to about 10 g/L; about 4 g/L to about 5 g/L, or any value in between. In certain embodiments, the butanol concentration in the production phase can be about 25 g/L to about 200 g/L; about 25 g/L to about 150 g/L; about 50 g/L to about 150 g/L; about 75 g/L to about 150 g/L; about 100 g/L to about 150 g/L; about 50 g/L to about 100 g/L; about 60 g/L to about 100 g/L; or about 75 g/L to about 100 g/L, or any value in between. In certain embodiments, the butanol concentration in the production phase can be at least about 25 g/L, at least about 100 g/L; at least about 150 g/L, or at least about 200 g/L.

In certain embodiments, the improved culture results in a reduction, elimination, or delay in production of the inhibitory product isobutyric acid. Optionally, the isobutyric acid concentration can be about 0 g/L to about 4 g/L; about 0 g/L to about 3 g/L; about 0 g/L to about 2.5 g/L; about 0 g/L to about 1.5 g/L; about 1 g/L to about 4 g/L; about 1 g/L to about 2.5 g/L; or about 1 g/L to about 2 g/L, or any value in between.

The processes provided herein involve protocols to control the butanol pathway flux by utilizing adaptive conditions to control activation of the engineered butanol biosynthetic pathway during the fermentation process. By way of an example, a recombinant microorganism comprising a butanol biosynthetic pathway which is differentially activated based on the concentration of glucose in the fermentation medium can have a butanol biosynthetic pathway that is inactivated or minimally activated in the presence of low glucose levels and is substantially or completely activated in the presence of excess glucose levels. Cultures of recombinant microorganisms with the butanol pathway inactivated or minimally activated (e.g., having a $q_p$ at or near 0% of the maximum $q_p$) can be provided at a high cell density for the fermentation process such that a desired biomass concentration can be achieved faster. Since the cell densities of the cultures are high when provided to the propagation tank, the residual glucose levels during the propagation phase can be reduced quickly, thus exposing the cultures to relatively low glucose concentrations during the propagation phase. Under these conditions, the culture may have enough time to partially activate the butanol biosynthetic pathway, thus producing a partially adapted cell culture. The partially adapted cells can be provided to a production tank, wherein the residual glucose concentration is high. As the pathway is slightly or partially active, it can allow for increased growth (e.g., increased biomass production); reduced or delayed production of an inhibitory product; increased biomass yield; increased butanol concentrations; increased butanol productivity; and consequently high volumetric titers of butanol.

Thus, processes for producing improved cell cultures (e.g., partially adapted cell cultures) can provide advantages to the fermentation process. Examples of process improvements and/or advantages can include, but are not limited to, an increase in biomass production, an increase in biomass yield, a reduction in the amount of time for the fermentation process (e.g., a reduction in the amount of time for propagation, for production, or for both propagation and production phases), a reduction or elimination of inhibitory products produced (e.g., a reduction or elimination of isobutanol, isobutyric acid, isobutyraldehyde, and/or acetic acid production) in the propagation phase, an increase in the preconditioning of the culture to inhibitory products (e.g., with increased biomass production and a reduction/delay in the production of inhibitory products, the culture can become preconditioned to slightly increasing levels of inhibitory products produced in the fermentation process as pathway activation occurs), a capability for the culture to continue growing resulting in an increase in biomass production in the production phase, an increase in butanol yield in the production phase, an increase in butanol productivity in the production phase, an increase in butanol concentration in the production phase, and/or a delay in the production of inhibitory products at the beginning of the production phase (e.g., a delay in the production of butanol and/or isobutyric acid). The delay in the production of isobutanol can allow for the increased growth/biomass production in the production phase. An additional process improvement can include increased operational flexibility (e.g., increased range of amount of cells to start fermentation process, increased scheduling flexibility for coordinating fermentation process).

Adaptive Conditions

Activation and/or inactivation of the engineered butanol biosynthetic pathway can, for example, be controlled by adaptive conditions (e.g., the process conditions) in which the cell culture is grown in each phase of the fermentation. Differences in the adaptive conditions can, for example, lead to the differential activation of the engineered butanol biosynthetic pathway such that the pathway can be inactivated or minimally activated at the start of the fermentation, and the pathway activation is increased due to adaptive conditions such that the pathway is substantially or completely activated during the fermentation process. In some embodiments, differential activation of the engineered butanol biosynthetic pathway can be controlled by promoter sequences controlling the expression of the enzymes required for the specific substrate to product conversions of the engineered butanol biosynthetic pathway. By way of an example, a glucose sensitive or oxygen sensitive promoter can be used to control an enzyme (e.g., acetolactate synthase) required for a substrate to product conversion in the engineered butanol biosynthetic pathway. In the absence of glucose and/or oxygen, the enzyme is not expressed or is not active, whereas in the presence of glucose and/or oxygen, the enzyme is expressed or is active. In some embodiments, differential activation of the engineered butanol biosynthetic pathway can be controlled by components of the fermentation media (e.g., a biochemical or chemical activator). In certain embodiments, differential activation of the engineered butanol biosynthetic pathway is controlled by the process conditions in which the recombinant microorganism culture is exposed.

In certain embodiments, the adaptive condition (i.e., process condition) is selected from at least one of a source of carbon substrate, a dissolved oxygen concentration, a temperature, a pH, a substrate (e.g., glucose) concentration, a butanol concentration, a butanol metabolite concentration, a 2-butanone concentration, or a component to the fermentation media (e.g., a biochemical or chemical activator).

In certain embodiments, differential activation of the engineered butanol biosynthetic pathway can be controlled by the source of the carbon substrate in the fermentation medium. By way of an example, the engineered butanol biosynthetic pathway can be inactivated or activated based on the presence of a fermentable carbon substrate selected from the group consisting of monosaccharides, oligosaccharides, polysaccharides, fatty acids, and mixtures thereof.

In certain embodiments, differential activation of the engineered butanol biosynthetic pathway can be controlled by the concentration of oxygen in the fermentation medium. A distinguishing characteristic between the propagation and production stages is the presence of high (e.g., greater than about 5%) dissolved oxygen concentration during the propagation phase, and low to no (e.g., less than about 5% or less than about 3% or about 0%) dissolved oxygen concentration during the production phase. Thus, in certain embodiments, "high" (e.g., aerobic conditions) vs. "low to none" (e.g., microaerobic to anaerobic conditions) can result in the differential activation of biocatalyst polypeptides of interest in the propagation vs. the production phases of the fermentation. By way of an example, the engineered butanol biosynthetic pathway can be inactive or partially activated in aerobic conditions in the propagation phase and consequently can be substantially or completely activated when pitched into microaerobic to anaerobic conditions in the production phase of the fermentation.

Optionally, the first set of adaptive conditions (e.g., process conditions) can comprise microaerobic to aerobic conditions. Optionally, the first set of adaptive conditions can be for the propagation phase of the fermentation. Microaerobic to aerobic conditions can be characterized by a specific oxygen uptake rate, a carbon dioxide evolution rate, or a respiratory quotient (RQ).

Specific carbon dioxide evolution rate (Sp. CER, millimoles/g/hr) and specific oxygen uptake rate (Sp. OUR, millimoles/g/hr) can be calculated by measuring flow rate, inlet and exhaust gas composition of air ($CO_2$, $O_2$, etc.), using, for example, mass spectrometry and/or cell density measurements. Specific carbon dioxide evolution rate is the ratio of carbon dioxide produced (air flow rate multiplied by difference between outlet and inlet carbon dioxide concentration) to cell density per unit time. Specific oxygen uptake rate is the ratio of oxygen consumed (air flow rate multiplied by difference between inlet and outlet oxygen concentration) to cell density per unit time. Respiratory quotient (RQ) is ratio of CER and OUR. Only the inlet and outlet gas composition from mass spectrometry are required to calculate RQ for a given constant air flow rate. RQ can be used as a control variable that couples the oxygen uptake rate with the carbon flux through the bioreactor system. RQ is intrinsically independent of scale. RQ can be measured, for example, using exhaust gas analysis.

In some embodiments, the Sp. OUR during a propagation phase is about 0.5 to about 5, about 0.5 to about 4, about 0.5 to about 3, about 0.5 to about 2, about 0.5 to about 1, about 1 to about 5, about 1 to about 4, about 1 to about 3, about 1 to about 3, about 2 to about 5, about 2 to about 4, about 2 to about 3, about 3 to about 5, about 3 to about 4, or about 4 to about 5 millimoles per grams of cell per hour, or any value in between.

In some embodiments, the Sp. CER during a propagation phase is about 1 to about 10, about 1 to about 7, about 1 to about 5, about 1 to about 3, about 1 to about 2, about 3 to about 10, about 3 to about 7, about 3 to about 5, about 5 to about 10, about 5 to about 8, about 5 to about 6, or about 7 to about 10 millimoles per grams of cell per hour, or any value in between.

In some embodiments, the RQ during a propagation phase is about 1 (aerobic) to about 10 (microaerobic), about 1 to about 7.5, about 1 to about 5, about 1 to about 2.5, about 2.5 to about 10, about 2.5 to about 7.5, about 2.5 to about 5, about 5 to about 10, about 5 to about 7.5, or about 7.5 to about 10, or any value in between.

Optionally, the second set of adaptive conditions (e.g., process conditions) can comprise microaerobic to anaerobic conditions. Optionally, the second set of adaptive conditions can be for the production phase of the fermentation. Microaerobic to anaerobic conditions can be characterized by a specific oxygen uptake rate, a carbon dioxide evolution rate, or a respiratory quotient (RQ).

In some embodiments, the Sp. OUR during a production phase is about 0 to about 2.5, about 0 to about 2, about 0 to about 1.5, about 0 to about 1, about 1 to about 2.5, about 1 to about 2, about 1 to about 1.5, about 1.5 to about 2.5, or about 1.5 to about 2 millimoles per grams of cell per hour, or any value in between.

In some embodiments, the Sp. CER during a production phase is about 1 to about 10, about 1 to about 7, about 1 to about 5, about 1 to about 3, about 1 to about 2, about 3 to about 10, about 3 to about 7, about 3 to about 5, about 5 to about 10, about 5 to about 8, about 5 to about 6, or about 7 to about 10 millimoles per grams of cell per hour, or any value in between In some embodiments, the RQ during a production phase is about 2 to infinity, about 2 to about 100, about 2 to about 75, about 2 to about 50, about 2 to about 25, about 2 to about 10, about 10 to about 100, about 10 to about 75, about 10 to about 50, about 10 to about 25, about 25 to about 100, about 25 to about 75, about 25 to about 50, about 50 to about 100, about 50 to about 75, or about 75 to about 100, or any value in between.

In certain embodiments, differential activation of the engineered butanol biosynthetic pathway can be controlled by the concentration of the substrate (e.g., glucose) in the fermentation medium. A distinguishing condition between the growth, propagation, and production phases is the presence of low glucose concentrations in the growth phase, medium to high glucose concentrations during the propagation phase, and high to excess glucose conditions during the production phase. Thus, in certain embodiments, medium to high glucose concentration vs. glucose excess conditions can result in the differential activation of the engineered butanol biosynthetic pathway in the propagation vs. the production phases of the fermentation. By way of an example, the engineered butanol biosynthetic pathway can be inactive or minimally activated in medium to high glucose concentrations in the propagation phase and consequently can be substantially or completely activated when pitched into glucose excess conditions in the production phase of the fermentation.

Optionally, the first or second set of process conditions can comprise glucose excess conditions. Glucose excess conditions can comprise glucose concentrations of about 1 g/L to about 50 g/L; about 3 g/L to about 50 g/L; about 5 g/L to about 50 g/L; about 10 g/L to about 50 g/L; about 20 g/L to about 50 g/L; about 30 g/L to about 50 g/L; about 40 g/L to about 50 g/L; about 1 g/L to about 25 g/L; about 5 g/L to about 25 g/L; about 10 g/L to about 25 g/L; about 15 g/L to about 25 g/L; about 20 g/L to about 25 g/L, or any value in between.

In certain embodiments, differential activation of the engineered butanol biosynthetic pathway can be controlled by the pH in the fermentation medium. By way of an example, the engineered butanol biosynthetic pathway can be inactived or minimally activated in lower pH conditions in the propagation phase and consequently can be substantially or completely activated when pitched into higher pH conditions in the production phase of the fermentation. By way of another example, the engineered butanol biosynthetic pathway can be inactivated or minimally activated in higher pH conditions in the propagation phase and consequently can be substantially or completely activated when pitched into lower pH conditions in the production phase of the fermentation.

In certain embodiments, differential activation of the engineered butanol biosynthetic pathway can be controlled by the temperature of the fermentation medium. By way of an example, the engineered butanol biosynthetic pathway can be inactivated or minimally activated in lower temperatures in the propagation phase and consequently can be substantially or completely activated when pitched into higher temperatures in the production phase of the fermentation. By way of another example, the engineered butanol biosynthetic pathway can be inactivated or minimally activated in higher temperatures and consequently can be substantially or completely activated when pitched into lower temperatures in the production phase of the fermentation.

In certain embodiments, differential activation of the engineered butanol biosynthetic pathway can be controlled by the concentration of butanol, a butanol metabolite, or 2-butanone in the fermentation medium. By way of an example, pathway activation can be increased as butanol concentrations are increased (e.g., if increased butanol concentrations can control production phase polypeptides).

In certain embodiments, differential activation of the engineered butanol biosynthetic pathway can be controlled by the addition of components to the fermentation media. By way of an example, biochemical or chemical components can be added to the fermentation media to activate an enzyme of the engineered butanol biosynthetic pathway resulting in increased production of butanol.

Differential Activation

Recombinant host cells comprising an engineered butanol biosynthetic pathway can be subjected to different conditions, such as the adaptive conditions corresponding to those of the propagation vs. the production phase, and the differential activation of the engineered butanol biosynthetic pathway can be confirmed by methods known in the art and/or provided herein. Differential expression of a polynucleotide encoding a biocatalyst polypeptide can be confirmed by comparing transcript levels under different conditions using reverse transcriptase polymerase chain reaction (RT-PCR) or real time PCR using methods known in the art. Differential expression of a polynucleotide of the engineered butanol biosynthetic pathway can be indicative of differential activation of the pathway. In some embodiments, a reporter, such as a green fluorescent protein (GFP) can be used in combination with flow cytometry to confirm the differential expression via a promoter nucleic acid sequence to affect expression under different conditions. Furthermore, the activity of a biocatalyst polypeptide may be determined under different conditions to confirm the differential expression of the polypeptide. By way of an example, where the acetolactate synthase is the biocatalyst polypeptide, the activity of acetolactate synthase present in host cells subjected to different conditions may be determined (using, e.g., methods described in W. W. Westerfeld, JBC 161:495-502 (1945)). A difference in acetolactate synthase activity can be used to confirm differential expression of acetolactate synthase. It is also envisioned that differential expression and/or activation of a biocatalyst polypeptide can be confirmed indirectly by measurement of downstream products or byproducts. For example, a decrease in production of isobutyraldehyde may be indicative of differential acetolactate synthase expression and/or activation.

It will be appreciated that other useful methods to confirm differential expression include measurement of biomass and/or measurement of biosynthetic pathway products under different conditions. For example, spectrophotometric measurement of optical density (O.D.) can be used as an indicator of biomass. Measurement of pathway products or by-products, including, but not limited to butanol concentration, DHMB concentration, or isobutyric acid can be carried out using methods known in the art and/or provided herein such as high pressure liquid chromatography (HPLC; for example, see PCT. Pub. No. WO2012/129555, incorporated herein by reference). Likewise, the rate of biomass increase, the rate of glucose consumption, or the rate of butanol production can be determined, for example by using the indicated methods. Biomass yield and product (e.g., butanol) yield can likewise be determined using methods disclosed in the art and/or herein.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., *Appl. Environ.*

Microbiol. 57:893-900 (1991); Underwood et al., *Appl. Environ. Microbiol.* 68:1071-81 (2002); Shen and Liao, *Metab. Eng.* 10:312-20 (2008); Hahnai et al., *Appl. Environ.* 73:7814-8 (2007); U.S. Pat. No. 5,514,583; U.S. Pat. No. 5,712,133; International Publication No. WO 1995/028476; Feldmann et al., *Appl. Microbiol. Biotechnol.* 38:354-61 (1992); Zhang et al., *Science* 267:240-3 (1995); U.S. Patent Publication No. 2007/0031918A1; U.S. Pat. No. 7,223,575; U.S. Pat. No. 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; 2011/0111472; 2012/0258873; and U.S. patent application Ser. No. 13/428,585, the entire contents of each are herein incorporated by reference. In some embodiments, microorganisms comprise a butanol biosynthetic pathway or a biosynthetic pathway for a butanol isomer such as 1-butanol, 2-butanol, or isobutanol. In some embodiments, the biosynthetic pathway converts pyruvate to a fermentative product. In some embodiments, the biosynthetic pathway converts pyruvate as well as amino acids to a fermentative product. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Lactococcus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In one embodiment, recombinant microorganisms may be selected from the group consisting of *Escherichia coli, Alcaligenes eutrophus, Bacillus licheniformis, Paenibacillus macerans, Rhodocuccus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii,* and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli,* and *Candida glabrata*.

In some embodiments, the host cell is *Saccharomyces cerevisiae. Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, and tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. No. 7,851,188; U.S. Pat. No. 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to isobutyraldehyde, which may be catalyzed, for example, by a branched-chain α-keto acid decarboxylase; and, e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to a-ketoisovalerate, which may be catalyzed, for example, by dihydroxyacid dehydratase;

d) the α-ketoisovalerate from step c) to valine, which may be catalyzed, for example, by transaminase or valine dehydrogenase;

e) the valine from step d) to isobutylamine, which may be catalyzed, for example, by valine decarboxylase;

f) the isobutylamine from step e) to isobutyraldehyde, which may be catalyzed by, for example, omega transaminase; and, g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to isobutyryl-CoA, which may be catalyzed, for example, by branched-chain keto acid dehydrogenase;

e) the isobutyryl-CoA from step d) to isobutyraldehyde, which may be catalyzed, for example, by acylating aldehyde dehydrogenase; and, f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;

b) the acetoacetyl-CoA from step a) to 3-hydroxybutyryl-CoA, which may be catalyzed, for example, by 3-hydroxybutyryl-CoA dehydrogenase;

c) the 3-hydroxybutyryl-CoA from step b) to crotonyl-CoA, which may be catalyzed, for example, by crotonase;

d) the crotonyl-CoA from step c) to butyryl-CoA, which may be catalyzed, for example, by butyryl-CoA dehydrogenase;

e) the butyryl-CoA from step d) to butyraldehyde, which may be catalyzed, for example, by butyraldehyde dehydrogenase; and, f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetoin aminase;

d) the 3-amino-2-butanol from step c) to 3-amino-2-butanol phosphate, which may be catalyzed, for example, by aminobutanol kinase;

e) the 3-amino-2-butanol phosphate from step d) to 2-butanone, which may be catalyzed, for example, by aminobutanol phosphate phosphorylase; and, f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin to 2,3-butanediol from step b), which may be catalyzed, for example, by butanediol dehydrogenase;

d) the 2,3-butanediol from step c) to 2-butanone, which may be catalyzed, for example, by dial dehydratase; and, e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetoin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

The terms "acetohydroxy acid synthase," "acetolactate synthase," and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources, including, but not limited to, *Bacillus subtilis* (GenBank Nos: CAB07802.1, Z99122, NCBI (National Center for Biotechnology Information) amino acid sequence, NCBI nucleotide sequence, respectively), CAB15618, *Klebsiella pneumoniae* (GenBank Nos: AAA25079, M73842), and *Lactococcus lactis* (GenBank Nos: AAA25161, L16975).

The term "ketol-acid reductoisomerase" ("KARI"), "acetohydroxy acid isomeroreductase," and "acetohydroxy acid reductoisomerase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118). KARIs include *Anaerostipes caccae* KARI variants "K9G9," "K9D3," and "K9JB4P." Ketol-acid reductoisomerase (KARI) enzymes are described in U.S. Pat. Nos. 7,910,342 and 8,129,162; U.S. Patent Application Publication Nos. 2008/0261230, 2009/0163376, 2010/0197519, PCT Application Publication No. WO/2011/041415, PCT Application Publication No. WO2012/129555; and U.S. Provisional Application No. 61/705,977, filed on Sep. 26, 2012, all of which are incorporated herein by reference. Examples of KARIs disclosed therein are those from *Lactococcus lactis, Anaerostipes caccae* and variants thereof; *Pseudomonas fluorescens* and PF5 mutants thereof; *Vibrio cholera*, and *Pseudomonas aeruginosa* PAO1. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC000913), *Saccharomyces cerevisiae* (GenBank Nos: NP_012550, NC_001142), *M. maripaludis* (GenBank Nos: CAF29874, BX957219), *B. subtilis* (GenBank Nos: CAB14105, Z99115), *L. lactis*, and *N. crassa*. U.S. Patent Application Publication No. 2010/0081154, U.S. Pat. No. 7,851,188, and U.S. Pat. No. 8,241,878, which are incorporated herein by reference, describe dihydroxyacid dehydratases (DHADs), including a DHAD from *Streptococcus mutans* and variants thereof.

The term "branched-chain α-keto acid decarboxylase," "α-ketoacid decarboxylase," "α-ketoisovalerate decarboxylase," or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760; CAG34226, AJ746364), *Salmonella typhimurium* (GenBank Nos: NP_461346, NC_003197), *Clostridium acetobutylicum* (GenBank Nos: NP_149189, NC_001988), *M. caseolyticus*, and *L. grayi*.

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136, NP_014051, NC_001145), *E. coli* (GenBank Nos: NP_417484, NC_000913), *C. acetobutylicum* (GenBank Nos: NP_349892, NC_003030; NP_349891, NC_003030). U.S. Patent Application Publication No. 2009/0269823 describes SadB, an alcohol dehydrogenase (ADH) from *Achromobacter xylosoxidans*. Alcohol dehydrogenases also include horse liver ADH and *Beijerinkia indica* ADH, as described by U.S. Patent Application Publication No. 2011/0269199, which is incorporated herein by reference.

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP 417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030) and *E. coli* (GenBank NOs: NP_417-484, NC_000913).

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988), *P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *Saccharomyces cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank NOs: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853, 2002).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., *Biochemistry* 43:13037-13046, 2004).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., *Appl. Environ. Microbial.* 67:4999-5009, 2001).

The term "aminobutanol phosphate phospholyase," also called "amino alcohol O-phosphate lyase," refers to a polypeptide (or polypeptides) having an enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., *Biochem J.* 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having an enzyme activity that catalyzes the conversion of 3-amino-2-butanol to 3-amino-2-butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP 830481, NC_004722; AAP07682, AE017000), and *Lactococcus lactis* (GenBank Nos. AAK04995, AE006323).

The term "butanediol dehydratase," also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin B12; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., *J. Agric. Food Chem.* 45:3476-3480, 1997), and nucleotide sequences that encode the corresponding enzymes. Methods of dial dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate dehydrogenases are known by the EC number 4.1.1.1. These enzymes are found in a number of yeast, including *Saccharomyces cerevisiae* (GenBank Nos: CAA97575, CAA97705, CAA97091).

The term "phosphoketolase" refers to an enzyme that catalyzes the conversion of xyulose 5-phosphate to glyceraldehyde 3-phosphate and acetyl phosphate. Example phosphoketolases are known by the EC number 4.1.2.9. In some embodiments, the phosphoketolase is xpk from *Lactobacillus plantarum*.

The term "phosphotransacetylase" refers to an enzyme that catalyzes the conversion of acetyl-CoA and phosphate to CoA and acetyl phosphate. Example phosphotransacetylases are known by the EC number 2.3.1.8. In some embodiments, the phosphotransacetylase is eutD from *Lactobacillus plantarum*.

It will be appreciated that host cells comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), modifications to a host cell that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway.

Other modifications include at least one deletion, mutation, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to DHMB. Such polypeptides can be determined by methods well known in the art and disclosed herein. As used herein, "DHMB" refers to 2,3-dihydroxy-2-methyl butyrate. DHMB includes "fast DHMB," which has the 2S, 3S configuration, and "slow DHMB," which has the 2S, 3R configuration. See Kaneko et al., *Phytochemistry* 39: 115-120 (1995), which is herein incorporated by reference in its entirety and refers to fast DHMB as anglyceric acid and slow DHMB as tiglyceric acid. In embodiments, the polypeptide having acetolactate reductase activity is YMR226C of *Saccharomyces cerevisiae* or a homolog thereof.

Additional modifications include a deletion, mutation, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to Enzyme Commission Numbers EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes carboxylic acids from aldehydes. Such polypeptides include a polypeptide that catalyzes the conversion of isobutyraldehyde to isobutyric acid. Such polypeptides also include a polypeptide that corresponds to Enzyme Commission Number EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof.

A genetic modification which has the effect of reducing glucose repression wherein the yeast production host cell is PDC— is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from PDC1 pyruvate decarboxylase from *Saccharomyces cerevisiae*, PDC5 pyruvate decarboxylase from *Saccharomyces cerevisiae*, PDC6 pyruvate decarboxylase from *Saccharomyces cerevisiae*, pyruvate decarboxylase from *Candida glabrata*, PDC1 pyruvate decarboxylase from *Pichia stipites*, PDC2 pyruvate decarboxylase from *Pichia stipites*, pyruvate decarboxylase from *Kluveromyces lactis*, pyruvate decarboxylase from *Yarrowia lipolytica*, pyruvate decarboxylase from *Schizosaccharomyces pombe*, and pyruvate decarboxylase from *Zygosaccharomyces rouxii*. In some embodiments, host cells contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

WIPO publication number WO 2011/103300 discloses recombinant host cells comprising (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In embodiments, the polypeptide affecting Fe—S cluster biosynthesis is encoded by AFT1, AFT2, FRA2, GRX3, or CCC1. In embodiments, the polypeptide affecting Fe—S cluster biosynthesis is constitutive mutant AFT1 L99A, AFT1 L102A, AFT1 C291F, or AFT1 C293F.

Additionally, host cells may comprise heterologous polynucleotides encoding a polypeptide with phosphoketolase activity and/or a heterologous polynucleotide encoding a polypeptide with phosphotransacetylase activity.

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., *Current Protocols in Molecular Biology*, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Expression of a Butanol Biosynthetic Pathway in Yeast

Methods for gene expression in yeast, e.g., *Saccharomyces cerevisiae*, are known in the art (e.g., *Methods in Enzymology*, Volume 194, *Guide to Yeast Genetics and Molecular and Cell Biology*, Part A, 2004, Christine Guthrie and Gerald R. Fink, eds., Elsevier Academic Press, San Diego, Calif.). Expression of genes in yeast typically requires a promoter, followed by the gene of interest, and a transcriptional terminator. A number of yeast promoters, including those used in the Examples herein, can be used in constructing expression cassettes for genes encoding an isobutanol biosynthetic pathway, including, but not limited to constitutive promoters FBA, GPD, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway can be cloned into *E. coli*-yeast shuttle vectors and transformed into yeast cells as described in U.S. App. Pub. No. 2010/0129886. These vectors allow strain propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with genes encoding polypeptides of interest can be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≥21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g., TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding region X-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

Growth for Production

Another embodiment of the present invention is directed to methods for producing various fermentation products including, but not limited to, lower alkyl alcohols. These methods employ the processes described above to produce the partially adapted recombinant host cells of the invention. In one embodiment, the method of the present invention comprises providing a recombinant host cell as discussed above, contacting the recombinant host cell with a fermentable carbon substrate in a fermentation medium under conditions whereby the fermentation product is produced and, optionally, recovering the fermentation product.

It will be appreciated that a process for producing fermentation products may comprise multiple phases. For example, process may comprise a first biomass production phase, a second biomass production phase, a fermentation production phase, and an optional recovery phase. In embodiments, processes provided herein comprise more than one, more than two, or more than three phases. It will be appreciated that process conditions may vary from phase to phase. For example, one phase of a process may be substantially aerobic, while the next phase may be substantially anaerobic. Other differences between phases may include, but are not limited to, source of carbon substrate (e.g., feedstock from which the fermentable carbon is derived), carbon substrate (e.g., glucose) concentration, dissolved oxygen, pH, temperature, or concentration of fermentation product (e.g., butanol). Promoter nucleic acid sequences and nucleic acid sequences encoding biocatalyst polypeptides and recombinant host cells comprising such promoter nucleic acid sequences may be employed in such processes. In embodiments, a biocatalyst polypeptide is preferentially expressed in at least one phase.

The propagation phase generally comprises at least one process by which biomass is increased. In embodiments, the temperature of the propagation phase may be at least about 20, at least about 30, at least about 35, or at least about 40° C. In embodiments, the pH in the propagation phase may be at least about 4, at least about 5, at least about 5.5, at least about 6, or at least about 6.5. In embodiments, the propagation phase continues until the biomass concentration reaches at least about 5, at least about 10, at least about 15, at least about 20, at least about 30, at least about 50, at least about 70, or at least about 100 g/L. In embodiments, the average glucose or sugar concentration is about or less than about 2 g/L, about or less than about 1 g/L, about or less than about 0.5 g/L or about or less than about 0.1 g/L. In embodiments, the dissolved oxygen concentration may average as undetectable, or as at least about 10%, at least about 20%, at least about 30%, or at least about 40%.

In one non-limiting example, a stage of the propagation phase comprises contacting a recombinant yeast host cell with at least one carbon substrate at a temperature of about 30 to about 35° C. and a pH of about 4 to about 5.5, until the biomass concentration is in the range of about 20 to about 100 g/L. The dissolved oxygen level over the course of the contact may average from about 20 to 40% (0.8-3.2 ppm). The source of the carbon substrate may be molasses or corn mash, or pure glucose or other sugar, such that the glucose or sugar concentration is from about 0 to about 1 g/L over the course of the contacting or from about 0 to about 0.1 g/L. In a subsequent or alternate stage of the propagation phase, a recombinant yeast host cell may be subjected to a further process whereby recombinant yeast at a concentration of about 0.1 g/L to about 1 g/L is contacted with at least one carbon substrate at a temperature of about 25 to about 35° C. and a pH of about 4 to about 5.5 until the biomass concentration is in the range of about 5 to about 15 g/L. The dissolved oxygen level over the course of the contact may average from undetectable to about 30% (0-2.4 ppm). The source of the carbon substrate may be corn mash such that the glucose concentration averages about 2 to about 30 g/L over the course of contacting.

It will be understood that the propagation phase may comprise one, two, three, four, or more stages, and that the above non-limiting example stages may be practiced in any order or combination.

The production phase typically comprises at least one process by which a product is produced. In embodiments, the average glucose concentration during the production phase is at least about 0.1, at least about 1, at least about 5, at least about 10 g/L, at least about 30 g/L, at least about 50 g/L, or at least about 100 g/L. In embodiments, the temperature of the production phase may be at least about 20, at least about 30, at least about 35, or at least about 40° C. In embodiments, the pH in the production phase may be at least about 4, at least about 5, or at least about 5.5. In embodiments, the production phase continues until the product titer reaches at least about 10 g/L, at least about 15 g/L, at least about 20 g/L, at least about 25 g/L, at least about 30 g/L, at least about 35 g/L or at least about 40 g/L. In embodiments, the dissolved oxygen concentration may average as less than about 5%, less than about 1%, or as negligible such that the conditions are substantially anaerobic.

In one non-limiting example production phase, recombinant yeast cells at a concentration of about 0.1 to about 6 g/L are contacted with at least one carbon substrate at a concentration of about 5 to about 100 g/L, temperature of about 25 to about 30° C., pH of about 4 to about 5.5. The dissolved oxygen level over the course of the contact may be negligible on average, such that the contact occurs under substantially anaerobic conditions. The source of the carbon substrate may mash such as corn mash, such that the glucose concentration averages about 10 to about 100 g/L over the course of the contacting, until it is substantially completely consumed.

In embodiments, the glucose concentration is about 100-fold to about 1000-fold higher in the production phase than in the propagation phase. In embodiments, the glucose concentration in production is at least about 5x, at least about 10x, at least about 50x, at least about 100x, or at least about 500x higher than that in propagation. In embodiments, the temperature in the propagation phase is about 5 to about 10 degrees lower in the production phase than in the propagation phase. In embodiments, the average dissolved oxygen concentration is anaerobic in the production phase and microaerobic to aerobic in the propagation phase.

One of skill in the art will appreciate that the conditions for propagating a host cell and/or producing a fermentation product utilizing a host cell may vary according to the host cell being used. In one embodiment, the method for producing a fermentation product is performed under anaerobic conditions. In one embodiment, the method for producing a fermentation product is performed under microaerobic conditions.

Further, it is envisioned that once a recombinant host cell comprising an engineered butanol biosynthetic pathway controlled by a suitable genetic switch, the process may be further refined to take advantage of the differential expression afforded thereby. For example, if the genetic switch provides preferential expression in high glucose conditions, one of skill in the art will be able to readily determine the glucose levels necessary to maintain minimal expression. As such, the glucose concentration in the phase of the process under which minimal expression is desired can be controlled so as to maintain minimal expression. In one non-limiting example, polymer-based slow-release feed beads (available, for example, from Kuhner Shaker, Basel, Switzerland) may be used to maintain a low glucose condition. A similar strategy can be employed to refine the propagation or production phase conditions relevant to the differential expression using the compositions and methods provided herein.

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], $7^{th}$ (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides, and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

In some embodiments, the butanologen produces butanol at least 90% of effective yield, at least 91% of effective yield, at least 92% of effective yield, at least 93% of effective yield, at least 94% of effective yield, at least 95% of effective yield, at least 96% of effective yield, at least 97% of effective yield, at least 98% of effective yield, or at least 99% of effective yield. In some embodiments, the butanologen produces butanol at about 55% to at about 75% of effective yield, about 50% to about 80% of effective yield, about 45% to about 85% of effective yield, about 40% to about 90% of effective yield, about 35% to about 95% of effective yield, about 30% to about 99% of effective yield, about 25% to about 99% of effective yield, about 10% to about 99% of effective yield, or about 10% to about 100% of effective yield.

Culture Conditions

Typically cells are grown at a temperature in the range of about 20° C. to about 40° C. in an appropriate medium. In some embodiments, the cells are grown at a temperature of 20° C., 22° C., 25° C., 27° C., 30° C., 32° C., 35° C., 37° C. or 40° C. In some embodiments, the cells are grown at a temperature of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

In some embodiments, the culture conditions are such that the fermentation occurs without respiration. For example, cells can be cultured in a fermenter under micro-aerobic or anaerobic conditions.

Industrial Batch and Continuous Fermentations

Butanol, or other products, can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments at the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch or continuous processes and that any known mode of fermentation would be suitable. Additionally, it is contemplated that cells can be immobilized on a substrate as whole cell catalysts and subjected to fermentation conditions for butanol production.

Methods for Butanol Isolation from the Fermentation Medium

Bioproduced butanol may be isolated from the fermentation medium using methods known in the art for ABE fermentations (see, e.g., Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. The butanol may be isolated from the fermentation medium using methods such as distillation, azeotropic distillation, liquid-liquid extraction, adsorption, gas stripping, membrane evaporation, or pervaporation.

Because butanol forms a low boiling point, azeotropic mixture with water, distillation can be used to separate the mixture up to its azeotropic composition. Distillation may be used in combination with the processes described herein to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, *Conceptual Design of Distillation Systems*, McGraw Hill, New York, 2001).

The butanol-water mixture forms a heterogeneous azeotrope so that distillation may be used in combination with decantation to isolate and purify the isobutanol. In this method, the butanol containing fermentation broth is distilled to near the azeotropic composition. Then, the azeotropic mixture is condensed, and the butanol is separated from the fermentation medium by decantation, wherein the butanol can be contacted with an agent to reduce the activity of the one or more carboxylic acids. The decanted aqueous phase may be returned to the first distillation column as reflux or to a separate stripping column. The butanol-rich decanted organic phase may be further purified by distillation in a second distillation column.

The butanol can also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption can also be used to isolate butanol from the fermentation medium. In this method, the fermentation broth containing the butanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation can be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches an inhibitory level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. Nos. 2009/0305370 and 2011/0097773, the disclosures of which are hereby incorporated in their entirety. U.S. Patent Appl. Pub. Nos. 2009/0305370 and 2011/0097773 describe methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, polyunsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, an alcohol ester can be formed by contacting the alcohol in a fermentation medium with an organic acid (e.g., fatty acids) and a catalyst capable of esterifying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. Carboxylic acids that are produced during the fermentation can additionally be esterified with the alcohol produced by the same or a different catalyst. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the inhibitory effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches an inhibitory level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Confirmation of Isobutanol Production

The presence and/or concentration of isobutanol in the culture medium can be determined by a number of methods known in the art (see, for example, U.S. Pat. No. 7,851,188, incorporated by reference). For example, a specific high performance liquid chromatography (HPLC) method utilizes a Shodex SH-1011 column with a Shodex SHG guard column, both may be purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions used.

Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of those skilled in the art to which this invention pertains, and are herein incorporated by reference to the same extent as if each individual publication, patent, or patent application was specifically and individually indicated to be incorporated by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA, molecular cloning techniques and transformation protocols used in the Examples are well known in the art and are described by Sambrook et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis), by Ausubel et al. (Ausubel et al., Current Protocols in Molecular Biology, pub. by Greene Publishing Assoc. and Wiley-Interscience, 1987) and by Amberg et al (Amberg, D. C., Burke, D. J. and Strathern, J. N. (Methods in Yeast Genetics: A Cold Spring Harbor Laboratory Course Manual, Cold Spring Harbor Press, 2005). Materials and methods suitable for the maintenance and growth of bacterial cultures are well known in the art. Techniques suitable for use in the following examples may be found as set out in Manual of Methods for General Bacteriology (Phillipp et al., eds., American Society for Microbiology, Washington, D.C., 1994) or by Thomas D. Brock in (Brock, Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "μmole" means micromole(s), "kg" means kilogram, "g" means gram(s), "μg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "μg/L" means microgram per liter, "ng/μL" means nanogram per microliter, "pmol/μL" means picomol per microliter, "RPM" means rotation per minute, "μmol/min/mg" means micromole per minute per milligram, "w/v" means weight per volume, "v/v" means volume per volume.

Strain Construction

Construction of Strain PNY2115

*Saccharomyces cerevisiae* strain PNY0827 is used as the host cell for further genetic manipulation for PNY2115. PNY0827 refers to a strain derived from *Saccharomyces cerevisiae* which has been deposited at the ATCC under the Budapest Treaty on Sep. 22, 2011 at the American Type Culture Collection, Patent Depository 10801 University Boulevard, Manassas, Va. 20110-2209 and has the patent deposit designation PTA-12105.

Deletion of URA3 and Sporulation into Haploids

In order to delete the endogenous URA3 coding region, a deletion cassette was PCR-amplified from pLA54 (SEQ ID NO: 1) which contains a $P_{TEF1}$-kanMX4-TEF1t cassette flanked by loxP sites to allow homologous recombination in vivo and subsequent removal of the KANMX4 marker. PCR was done by using Phusion High Fidelity PCR Master Mix (New England BioLabs; Ipswich, Mass.) and primers BK505 (SEQ ID NO: 2) and BK506 (SEQ ID NO: 3). The URA3 portion of each primer was derived from the 5' region 180 bp upstream of the URA3 ATG and 3' region 78 bp downstream of the coding region such that integration of the kanMX4 cassette results in replacement of the URA3 coding region. The PCR product was transformed into PNY0827 using standard genetic techniques (Methods in Yeast Genetics, 2005, Cold Spring Harbor Laboratory Press, Cold Spring Harbor, N.Y., pp. 201-202) and transformants were selected on YEP medium supplemented 2% glucose and 100 µg/ml Geneticin at 30° C. Transformants were screened by colony PCR with primers LA468 (SEQ ID NO: 4) and LA492 (SEQ ID NO: 5) to verify presence of the integration cassette. A heterozygous diploid was obtained: NYLA98, which has the genotype MATa/α URA3/ura3::loxP-kanMX4-loxP. To obtain haploids, NYLA98 was sporulated using standard methods (Codón A C, Gasent-Ramirez J M, Benitez T. Factors which affect the frequency of sporulation and tetrad formation in Saccharomyces cerevisiae baker's yeast. Appl Environ Microbiol. 1995 PMID: 7574601). Tetrads were dissected using a micromanipulator and grown on rich YPE medium supplemented with 2% glucose. Tetrads containing four viable spores were patched onto synthetic complete medium lacking uracil supplemented with 2% glucose, and the mating type was verified by multiplex colony PCR using primers AK109-1 (SEQ ID NO: 6), AK109-2 (SEQ ID NO: 7), and AK109-3 (SEQ ID NO: 8). The resulting identified haploid strain called NYLA103, which has the genotype: MATα ura3Δ::loxP-kanMX4-loxP, and NYLA106, which has the genotype: MATa ura3Δ::loxP-kanMX4-loxP.

Deletion of His3

To delete the endogenous HIS3 coding region, a scarless deletion cassette was used. The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO: 9) and primer oBP453 (SEQ ID NO: 10), containing a 5' tail with homology to the 5' end of HIS3 Fragment B. HIS3 Fragment B was amplified with primer oBP454 (SEQ ID NO: 11), containing a 5' tail with homology to the 3' end of HIS3 Fragment A, and primer oBP455 (SEQ ID NO: 12) containing a 5' tail with homology to the 5' end of HIS3 Fragment U. HIS3 Fragment U was amplified with primer oBP456 (SEQ ID NO: 13), containing a 5' tail with homology to the 3' end of HIS3 Fragment B, and primer oBP457 (SEQ ID NO: 14), containing a 5' tail with homology to the 5' end of HIS3 Fragment C. HIS3 Fragment C was amplified with primer oBP458 (SEQ ID NO: 15), containing a 5' tail with homology to the 3' end of HIS3 Fragment U, and primer oBP459 (SEQ ID NO: 16). PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO: 9) and oBP455 (SEQ ID NO: 12). HIS3 Fragment UC was created by overlapping PCR by mixing HIS3 Fragment U and HIS3 Fragment C and amplifying with primers oBP456 (SEQ ID NO: 13) and oBP459 (SEQ ID NO: 16). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO: 9) and oBP459 (SEQ ID NO: 16). The PCR product was purified with a PCR Purification kit (Qiagen). Competent cells of NYLA106 were transformed with the HIS3 ABUC PCR cassette and were plated on synthetic complete medium lacking uracil supplemented with 2% glucose at 30° C. Transformants were screened to verify correct integration by replica plating onto synthetic complete medium lacking histidine and supplemented with 2% glucose at 30° C. Genomic DNA preps were made to verify the integration by PCR using primers oBP460 (SEQ ID NO: 17) and LA135 (SEQ ID NO: 18) for the 5' end and primers oBP461 (SEQ ID NO: 19) and LA92 (SEQ ID NO: 20) for the 3' end. The URA3 marker was recycled by plating on synthetic complete medium supplemented with 2% glucose and 5-FOA at 30° C. following standard protocols. Marker removal was confirmed by patching colonies from the 5-FOA plates onto SD-URA medium to verify the absence of growth. The resulting identified strain, called PNY2003 has the genotype: MATa ura3Δ::loxP-kanMX4-loxP his3Δ.

Deletion of PDC1

To delete the endogenous PDC1 coding region, a deletion cassette was PCR-amplified from pLA59 (SEQ ID NO: 21), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA678 (SEQ ID NO: 22) and LA679 (SEQ ID NO: 23). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into PNY2003 using standard genetic techniques and transformants were selected on synthetic complete medium lacking uracil and supplemented with 2% glucose at 30° C. Transformants were screened to verify correct integration by colony PCR using primers LA337 (SEQ ID NO: 24), external to the 5' coding region and LA135 (SEQ ID NO: 18), an internal primer to URA3. Positive transformants were then screened by colony PCR using primers LA692 (SEQ ID NO: 25) and LA693 (SEQ ID NO: 26), internal to the PDC1 coding region. The URA3 marker was recycled by transforming with pLA34 (SEQ ID NO: 27) containing the CRE recombinase under the GAL1 promoter and plated on synthetic complete medium lacking histidine and supplemented with 2% glucose at 30° C. Transformants were plated on rich medium supplemented with 0.5% galactose to induce the recombinase. Marker removal was confirmed by patching colonies to synthetic complete medium lacking uracil and supplemented with 2% glucose to verify absence of growth. The resulting identified strain, called PNY2008 has the genotype: MATa ura3Δ::loxP-kanMX4-loxP his3Δ pdc1Δ::loxP71/66.

Deletion of PDC5

To delete the endogenous PDC5 coding region, a deletion cassette was PCR-amplified from pLA59 (SEQ ID NO: 21), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA722 (SEQ ID NO: 28) and LA733 (SEQ ID NO: 29). The PDC5 portion of each primer was derived from the 5' region 50 bp upstream of the PDC5 start codon and 3' region 50 bp downstream of the stop codon such that integration of the URA3 cassette results in replacement of the entire PDC5 coding region. The PCR product was transformed into PNY2008 using standard genetic techniques and transformants were selected on synthetic complete medium lacking uracil and supplemented with 1% ethanol at 30° C. Transformants were screened to verify correct integration by colony PCR using primers LA453 (SEQ ID NO: 30), external to the 5' coding region and LA135 (SEQ ID NO: 18), an internal primer to URA3. Positive transformants were then screened by colony PCR using primers LA694 (SEQ ID NO: 31) and LA695 (SEQ ID NO: 32), internal to the PDC5 coding region. The URA3 marker was recycled by transforming with pLA34 (SEQ ID NO: 27) containing the CRE recombinase under the GAL1 promoter and plated on synthetic complete medium lacking histidine and supplemented with 1% ethanol at 30° C. Transformants were plated on rich YEP medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2009 has the genotype: MATa ura3Δ::loxP-kanMX4-loxP his3Δ pdc1Δ::loxP71/66 pdc5Δ::loxP71/66.

Deletion of FRA2

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). FRA2 Fragment A was amplified with primer oBP594 (SEQ ID NO: 33) and primer oBP595 (SEQ ID NO: 34), containing a 5' tail with homology to the 5' end of FRA2 Fragment B. FRA2 Fragment B was amplified with primer oBP596 (SEQ ID NO: 35), containing a 5' tail with homology to the 3' end of FRA2 Fragment A, and primer oBP597 (SEQ ID NO: 36), containing a 5' tail with homology to the 5' end of FRA2 Fragment U. FRA2 Fragment U was amplified with primer oBP598 (SEQ ID NO: 37), containing a 5' tail with homology to the 3' end of FRA2 Fragment B, and primer oBP599 (SEQ ID NO: 38), containing a 5' tail with homology to the 5' end of FRA2 Fragment C. FRA2 Fragment C was amplified with primer oBP600 (SEQ ID NO: 39), containing a 5' tail with homology to the 3' end of FRA2 Fragment U, and primer oBP601 (SEQ ID NO: 40). PCR products were purified with a PCR Purification kit (Qiagen). FRA2 Fragment AB was created by overlapping PCR by mixing FRA2 Fragment A and FRA2 Fragment B and amplifying with primers oBP594 (SEQ ID NO: 33) and oBP597 (SEQ ID NO: 36). FRA2 Fragment UC was created by overlapping PCR by mixing FRA2 Fragment U and FRA2 Fragment C and amplifying with primers oBP598 (SEQ ID NO: 37) and oBP601 (SEQ ID NO: 40). The resulting PCR products were purified on an agarose gel followed by a Gel Extraction kit (Qiagen). The FRA2 ABUC cassette was created by overlapping PCR by mixing FRA2 Fragment AB and FRA2 Fragment UC and amplifying with primers oBP594 (SEQ ID NO: 33) and oBP601 (SEQ ID NO: 40). The PCR product was purified with a PCR Purification kit (Qiagen).

To delete the endogenous FRA2 coding region, the scarless deletion cassette obtained above was transformed into PNY2009 using standard techniques and plated on synthetic complete medium lacking uracil and supplemented with 1% ethanol. Genomic DNA preps were made to verify the integration by PCR using primers oBP602 (SEQ ID NO: 41) and LA135 (SEQ ID NO: 18) for the 5' end, and primers oBP602 (SEQ ID NO: 41) and oBP603 (SEQ ID NO: 42) to amplify the whole locus. The URA3 marker was recycled by plating on synthetic complete medium supplemented with 1% ethanol and 5-FOA (5-Fluoroorotic Acid) at 30° C. following standard protocols. Marker removal was confirmed by patching colonies from the 5-FOA plates onto synthetic complete medium lacking uracil and supplemented with 1% ethanol to verify the absence of growth. The resulting identified strain, PNY2037, has the genotype: MATa ura3Δ::loxP-kanMX4-loxP his3Δ pdc1Δ::loxP71/66 pdc5Δ::loxP71/66 fra2Δ.

Addition of Native 2 Micron Plasmid

The loxP71-URA3-loxP66 marker was PCR-amplified using Phusion DNA polymerase (New England BioLabs; Ipswich, Mass.) from pLA59 (SEQ ID NO: 21), and transformed along with the LA811x817 (SEQ ID NOs: 43, 44) and LA812x818 (SEQ ID NOs: 45, 46) 2-micron plasmid fragments (amplified from the native 2-micron plasmid from CEN.PK 113-7D; Centraalbureau voor Schimmelcultures (CBS) Fungal Biodiversity Centre) into strain PNY2037 on SE-URA plates at 30° C. The resulting strain PNY2037 2μ::loxP71-URA3-loxP66 was transformed with pLA34 (pRS423::cre) (also called, pLA34) (SEQ ID NO: 27) and selected on SE-HIS-URA plates at 30° C. Transformants were patched onto YP-1% galactose plates and allowed to grow for 48 hours at 30° C. to induce Cre recombinase expression. Individual colonies were then patched onto SE-URA, SE-HIS, and YPE plates to confirm URA3 marker removal. The resulting identified strain, PNY2050, has the genotype: MATa ura3Δ::loxP-kanMX4-loxP, his3Δ pdc1Δ::loxP71/66 pdc5Δ::loxP71/66 fra2Δ 2-micron.

Construction of PNY2115 from PNY2050

Construction of PNY2115 [MATa ura3Δ::loxP his3Δ pdc5Δ::loxP66/71 fra2Δ 2-micron plasmid (CEN.PK2) pdc1Δ::P[PDC1]-ALS|alsS_Bs-CYC1t-loxP71/66 pdc6Δ:: (UAS)PGK1-P[FBA1]-KIVD|Lg(y)-TDH3t-loxP71/66 adh1Δ::P[ADH1]-ADH|Bi(y)-ADHt-loxP71/66 fra2Δ::P [ILV5]-ADH|Bi(y)-ADHt-loxP71/66 gpd2Δ::loxP71/66] from PNY2050 was as follows.

Pdc1Δ::P[PDC1]-ALS|alsS_Bs-CYC1t-loxP71/66

To integrate alsS into the pdc1Δ::loxP66/71 locus of PNY2050 using the endogenous PDC1 promoter, An integration cassette was PCR-amplified from pLA71 (SEQ ID NO: 52), which contains the gene acetolactate synthase from the species *Bacillus subtilis* with a FBA1 promoter and a CYC1 terminator, and a URA3 marker flanked by degenerate loxP sites to allow homologous recombination in vivo and subsequent removal of the URA3 marker. PCR was done by using KAPA HiFi and primers 895 (SEQ ID NO: 55) and 679 (SEQ ID NO: 56). The PDC1 portion of each primer was derived from 60 bp of the upstream of the coding sequence and 50 bp that are 53 bp upstream of the stop codon. The PCR product was transformed into PNY2050 using standard genetic techniques and transformants were selected on synthetic complete media lacking uracil and supplemented with 1% ethanol at 30° C. Transformants were screened to verify correct integration by colony PCR using primers 681 (SEQ ID NO: 57), external to the 3' coding region and 92 (SEQ ID NO: 58), internal to the URA3 gene. Positive transformants were then prepped for genomic DNA and screened by PCR using primers N245 (SEQ ID NO: 59) and N246 (SEQ ID NO: 60). The URA3 marker was recycled by transforming with pLA34 (SEQ ID NO: 27) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2090 has the genotype MATa ura3Δ::loxP, his3Δ, pdc1Δ::loxP71/66, pdc5Δ::loxP71/66 fra2Δ 2-micron pdc1Δ::P[PDC1]-ALS|alsS_Bs-CYC1t-loxP71/66.
Pdc6Δ::(UAS)PGK1-P[FBA1]-KIVD|Lg(y)-TDH3t-loxP71/66

To delete the endogenous PDC6 coding region, an integration cassette was PCR-amplified from pLA78 (SEQ ID NO: 53), which contains the kivD gene from the species *Listeria grayi* with a hybrid FBA1 promoter and a TDH3 terminator, and a URA3 marker flanked by degenerate loxP sites to allow homologous recombination in vivo and subsequent removal of the URA3 marker. PCR was done by using KAPA HiFi and primers 896 (SEQ ID NO: 61) and 897 (SEQ ID NO: 62). The PDC6 portion of each primer was derived from 60 bp upstream of the coding sequence and 59 bp downstream of the coding region. The PCR product was transformed into PNY2090 using standard genetic techniques and transformants were selected on synthetic complete media lacking uracil and supplemented with 1% ethanol at 30° C. Transformants were screened to verify correct integration by colony PCR using primers 365 (SEQ ID NO: 63) and 366 (SEQ ID NO: 64), internal primers to the PDC6 gene. Transformants with an absence of product were then screened by colony PCR N638 (SEQ ID NO: 65), external to the 5' end of the gene, and 740 (SEQ ID NO: 66), internal to the FBA1 promoter. Positive transformants were than the prepped for genomic DNA and screened by PCR with two external primers to the PDC6 coding sequence. Positive integrants would yield a 4720 bp product, while PDC6 wild type transformants would yield a 2130 bp product. The URA3 marker was recycled by transforming with pLA34 containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain is called PNY2093 and has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66.
Adh1Δ::P[ADH1]-ADH|Bi(y)-ADHt-loxP71/66

To delete the endogenous ADH1 coding region and integrate BiADH using the endogenous ADH1 promoter, an integration cassette was PCR-amplified from pLA65 (SEQ ID NO: 54), which contains the alcohol dehydrogenase from the species *Beijerinckii* with an ILV5 promoter and a ADH1 terminator, and a URA3 marker flanked by degenerate loxP sites to allow homologous recombination in vivo and subsequent removal of the URA3 marker. PCR was done by using KAPA HiFi and primers 856 (SEQ ID NO: 67) and 857 (SEQ ID NO: 68). The ADH1 portion of each primer was derived from the 5' region 50 bp upstream of the ADH1 start codon and the last 50 bp of the coding region. The PCR product was transformed into PNY2093 using standard genetic techniques and transformants were selected on synthetic complete media lacking uracil and supplemented with 1% ethanol at 30° C. Transformants were screened to verify correct integration by colony PCR using primers BK415 (SEQ ID NO: 69), external to the 5' coding region and N1092 (SEQ ID NO: 70), internal to the BiADH gene. Positive transformants were then screened by colony PCR using primers 413 (SEQ ID NO: 75), external to the 3' coding region, and 92 (SEQ ID NO: 58), internal to the URA3 marker. The URA3 marker was recycled by transforming with pLA34 (SEQ ID NO: 27) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2101 has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66.
Fra2Δ::P[ILV5]-ADH|Bi(y)-ADHt-loxP71/66

To integrate BiADH into the fra2Δ locus of PNY2101, an integration cassette was PCR-amplified from pLA65 (SEQ ID NO: 54), which contains the alcohol dehydrogenase from the species *Beijerinckii indica* with an ILV5 promoter and an ADH1 terminator, and a URA3 marker flanked by degenerate loxP sites to allow homologous recombination in vivo and subsequent removal of the URA3 marker. PCR was done by using KAPA HiFi and primers 906 (SEQ ID NO: 71) and 907 (SEQ ID NO: 72). The FRA2 portion of each primer was derived from the first 60 bp of the coding sequence starting at the ATG and 56 bp downstream of the stop codon. The PCR product was transformed into PNY2101 using standard genetic techniques and transformants were selected on synthetic complete media lacking uracil and supplemented with 1% ethanol at 30° C. Transformants were screened to verify correct integration by colony PCR using primers 667 (SEQ ID NO: 73), external to the 5' coding region and 749 (SEQ ID NO: 74), internal to the ILV5 promoter. The URA3 marker was recycled by transforming with pLA34 (SEQ ID NO: 27) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2110 has the genotype MATa ura3Δ::loxP his3Δ pdc5Δ::loxP66/71 2-micron pdc1Δ::P[PDC1]-ALS|alsS_Bs-CYC1t-loxP71/66 pdc6Δ:(UAS)PGK1-P[FBA1]-KIVD|Lg(y)-TDH3t-loxP71/66 adh1Δ::P[ADH1]-ADH|Bi(y)-ADHt-loxP71/66 fra24::P[ILV5]-ADH|Bi(y)-ADHt-loxP71/66.
GPD2 Deletion To delete the endogenous GPD2 coding region, a deletion cassette was PCR amplified from pLA59 (SEQ ID NO: 21), which contains a URA3 marker flanked by degenerate loxP sites to allow homologous recombination in vivo and subsequent removal of the URA3 marker. PCR was done by using KAPA HiFi and primers LA512 (SEQ ID NO: 47) and LA513 (SEQ ID NO: 48). The GPD2 portion of each primer was derived from the 5'region 50 bp upstream of the GPD2 start codon and 3' region 50 bp downstream of the stop codon such that integration of the URA3 cassette results in replacement of the entire GPD2 coding region. The PCR product was transformed into PNY2110 using standard genetic techniques and transformants were selected on synthetic complete medium lacking uracil and supplemented with 1% ethanol at 30° C. Transformants were screened to verify correct integration by colony PCR using primers LA516 (SEQ ID NO: 49) external to the 5' coding region and LA135 (SEQ ID NO: 18), internal to URA3. Positive transformants were then screened by colony PCR using primers LA514 (SEQ ID NO: 50) and LA515 (SEQ ID NO: 51), internal to the GPD2 coding region. The URA3 marker was recycled by transforming with pLA34 (SEQ ID NO: 27) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2115, has the genotype MATa ura3Δ::loxP his3Δ pdc5Δ::loxP66/71 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66.

Creation of PNY2145 from PNY2115

PNY2145 was constructed from PNY2115 by the additional integration of a phosphoketolase gene cassette at the pdc5Δ locus and by replacing the native AMN1 gene with a codon optimized version of the ortholog from CEN.PK. Integration constructs are further described below.

pdc5Δ::FBA(L8)-xpk1-CYC1t-loxP71/66

The TEF(M4)-xpk1-CYC1t gene from pRS423::TEF(M4)-xpk1+ENO1-eutD (SEQ ID NO: 76) was PCR amplified using primers N1341 and N1338 (SEQ ID NOs: 77 and 78), generating a 3.1 kb product. The loxP-flanked URA3 gene cassette from pLA59 (SEQ ID NO: 21) was amplified with primers N1033c and N1342 (SEQ ID NOs: 79 and 80), generating a 1.6 kb product. The xpk1 and URA3 PCR products were fused by combining them without primers for an additional 10 cycles of PCR using Phusion DNA polymerase. The resulting reaction mix was then used as a template for a PCR reaction with KAPA Hi Fi and primers N1342 and N1364 (SEQ ID NOs: 80 and 81). A 4.2 kb PCR product was recovered by purification from an electrophoresis agarose gel (Zymo kit). FBA promoter variant L8 (SEQ ID NO: 82) was amplified using primers N1366 and N1368 (SEQ ID NOs: 83 and 84). The xpk1::URA3 PCR product was combined with the FBA promoter by additional rounds of PCR. The resulting product was phosphorylated with polynucleotide kinase and ligated into pBR322 that had been digested with EcoRV and treated with calf intestinal phosphatase. The ligation reaction was transformed into E. coli cells (Stbl3 competent cells from Invitrogen). The integration cassette was confirmed by sequencing. To prepare DNA for integration, the plasmid was used as a template in a PCR reaction with Kapa HiFi and primers N1371 and N1372 (SEQ ID NOs: 85 and 86). The PCR product was isolated by phenol-chloroform extraction and ethanol precipitation (using standard methods; e.g., Maniatas, et al.). Five micrograms of DNA were used to transform strain PNY2115. Transformants were selected on medium lacking uracil (synthetic complete medium minus uracil with 1% ethanol as the carbon source). Colonies were screened for the integration event using PCR (JumpStart) with primers BK93 and N1114 (SEQ ID NOs: 87 and 88). Two clones were selected to carry forward. The URA3 marker was recycled by transforming with pJT254 (SEQ ID NO: 89) containing the CRE recombinase under the GAL1 promoter and plating on synthetic complete medium lacking histidine and supplemented with 1% ethanol at 30° C. Transformants were grown in rich medium supplemented with 1% ethanol to derepress the recombinase. Marker removal was confirmed for single colony isolates by patching to synthetic complete medium lacking uracil and supplemented with 1% ethanol to verify absence of growth. Loss of the recombinase plasmid, pJT254, was confirmed by patching the colonies to synthetic complete medium lacking histidine and supplemented with 1% ethanol. Proper marker removal was confirmed by PCR (primers N160SeqF5 (SEQ ID NO: 90) and BK380. One resulting clone was designated PNY2293.

amn1Δ::AMN1(y)-loxP71/66

To replace the endogenous copy of AMN1 with a codon-optimized version of the AMN1 gene from CEN.PK2, an integration cassette containing the CEN.PK AMN1 promoter, AMN1(y) gene (nucleic acid SEQ ID NO: 91; amino acid SEQ ID NO: 92), and CEN.PK AMN1 terminator was assembled by SOE PCR and subcloned into the shuttle vector pLA59. The AMN1(y) gene was ordered from DNA 2.0 with codon-optimization for S. cerevisiae. The completed pLA67 plasmid (SEQ ID NO: 93) contained: 1) pUC19 vector backbone sequence containing an E. coli replication origin and ampicillin resistance gene; 2) URA3 selection marker flanked by loxP71 and loxP66 sites; and 3) $P_{AMN1(CEN.PK)}$-AMN1(y)-term$_{AMN1(CEN.PK)}$ expression cassette PCR amplification of the AMN1(y)-loxP71-URA3-loxP66 cassette was done by using KAPA HiFi from Kapa Biosystems, Woburn, Mass. and primers LA712 (SEQ ID NO: 94) and LA746 (SEQ ID NO: 95). The PCR product was transformed into PNY2293 using standard genetic techniques and transformants were selected on synthetic complete medium lacking uracil and supplemented with 1% ethanol at 30° C. Transformants were observed under magnification for the absence of a clumping phenotype with respect to the control (PNY2293). The URA3 marker was recycled using the pJT254 Cre recombinase plasmid as described above. After marker recycle, clones were again observed under magnification to confirm absence of the clumping phenotype. A resulting identified strain, PNY2145, has the genotype: MATa ura3Δ::loxP his3Δ pdc5Δ::P[FBA(L8)]-XPK|xpk1_Lp-CYCt-loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66 amn1Δ::AMN1(y).

Creation of PNY1621 from PNY2145

Strain PNY1621 was constructed from strain PNY2145. The chimeric gene on chromosome XII in PNY2145 consisting of the PDC1 promoter, alsS coding region, CYC1 terminator, and loxP71/66 site was deleted from 750 bp upstream of the alsS coding region to the first base of native PDC1 3' UTR region. The region was deleted using CRE-lox mediated marker removal. The region was replaced with a chimeric gene comprised of the FBA1::HXT1_331 promoter and the alsS coding region from Bacillus subtilis. The native PDC1 terminator was used to complete the chimeric gene. A loxP71/66 site flanked by two priming sites remained upstream of the promoter after CRE-mediated marker removal. The sequence of the modified locus is provided in SEQ ID NO:96 (native upstream region=nt 1-100; priming site-loxP71/66-priming site=nt 109-203; FBA1::HXT1_331 promoter=nt 210-985; alsS coding region=nt 994-2709; native downstream region=nt 2716-2815). The sequence of the resulting locus was confirmed by sequencing and/or PCR. Plasmids were introduced into the strain for expression of KARI and DHAD (pLH804::L2V4, plasmid SEQ ID NO:97) and KivD and ADH (pRS413::BiADH-kivD_Lg(y), plasmid SEQ ID NO:98). pLH804::L2V4 was constructed to contain a chimeric gene having the coding region of the ilvD gene from Streptococcus mutans containing the L2V4 mutation (nt position 5356-3641) expressed from the yeast TEF1 mutant 7 promoter (nt 5766-5366; Nevoigt et al. 2006. Applied and Environmental Microbiology, v72 p5266) and followed by the FBA1 terminator (nt 3632-3320) for expression of DHAD, and a chimeric gene having the coding region of the K9JB4P mutant ilvC gene from Anaeropstipes cacae (nt 1628-2659) expressed from the yeast ILV5 promoter (nt 434-1614) and followed by the ILV5 terminator (nt 2673-3307) for expression of KARI. pRS413::BiADH-kivD_Lg(y) was constructed to contain a chimeric gene having the coding region of the kivD gene from Listeria grayi codon optimized for expression in Saccharomyces cerevisiae (nt position 2902-4548) expressed from the UAS(PGK1) FBA1 promoter (nt 2169-2893) and followed by the TDH3 terminator (nt 4560-5139) for expression of KivD, and a chimeric gene having the coding region of the adh gene from Beijerinckia indica codon optimized for expression in Saccharomyces cerevisiae (nt 6853-7896) expressed from the yeast PDC1 promoter (nt 5983-6852) and followed by the ADH1 terminator (nt 7905-8220) for expression of ADH. The resulting strain was designated PNY1621.

Example 1

Effect of Partial Adaptation of Butanologen in Production Phase of Fermentation

This example provides one method to generate the substantially adapted and partially adapted recombinant microorganisms and to subsequently test for performance in production.

Glycerol Stock Preparation:

Cells of the engineered yeast strain PNY1621 were inoculated in 20 ml synthetic complete medium (1× yeast nitrogen base without amino acids (Becton Dickinson; Franklin Lakes, N.J.), 1× amino acid drop-out without Histidine and Uracil (Clonetech; Mountain View, Calif.) containing 2 g/l glucose (Sigma; St. Louis, Mo.) and 2 g/l ethanol) in 125 ml flask. Cells were grown at 30° C. for 24 hours with agitation at 200 rpm. This culture was used to inoculate 90 ml of fresh synthetic complete medium (with 2 g/l ethanol and 2 g/l glucose) in 250 ml flask and grown for 24 hours at 30° C. and 200 rpm. After 24 hours, cells were harvested by centrifugation at 4000 rpm for 5 minutes and re-suspended at an initial $OD_{600nm}$ of 20 in synthetic complete medium containing 2 g/l ethanol and 20% v/v glycerol (Sigma). These cells were distributed in aliquots of 1 ml in screw cap tubes and frozen using slow freezers and stored at −80° C. (glycerol stocks) until use.

Substantially Adapted Biomass Generation

A.1 Seed Stage

Seed culture was prepared in three stages: pre-seed, seed 1, and seed 2. Pre-seed culture was started by inoculating 3 vials of 20 OD glycerol stock in 100 ml of filter sterilized preseed medium (containing 0.65 g/l amino acid dropout without Histidine, Uracil and Leucine (Clonetech), 60 mg/l Leucine (Sigma), 6.5 g/l yeast nitrogen base without amino acids (Difco; Becton Dickinson), 20 g/l glucose, 19.5 g/l 4-Morpholineethane-sulphonic acid (Sigma), 50 mg/l ampicillin ((Himedia; Mumbai, India) with pH adjusted to 5.5 using 1M $H_2SO_4$) in 500 ml flask and grown at 30° C. and 250 rpm for 24 hours. Seed 1 stage was initiated by adding 40 ml of pre-seed culture in 200 ml of filter sterilized fresh pre-seed medium with pH of 5.5 in 1 L flask and incubated at 30° C. and 250 rpm for 24 hours. In the seed 2 stage, 80 ml of seed 1 culture was inoculated in 400 ml of fresh pre-seed medium in 2 L flask and incubated at 30° C. and 250 rpm for 24 hours.

Partially Adapted Biomass Generation

B.1 Seed Stage

Seed culture was prepared in three stages: pre-seed, seed 1, and seed 2. Pre-seed culture was started by inoculating 3 vials of 20 OD glycerol stock in 100 ml of filter sterilized pre-seed medium (containing 0.65 g/l amino acid dropout without Histidine, Uracil and Leucine (Clonetech), 60 mg/l Leucine (Sigma), 6.5 g/l yeast nitrogen base without amino acids (Difco), 10 g/l glucose, 5 g/l ethanol, 19.5 g/l 4-Morpholineethane-sulphonic acid (Sigma), 50 mg/l ampicillin ((Himedia) with pH adjusted to 5.5 using 1M $H_2SO_4$) in 500 ml flask and grown at 30° C. and 250 rpm for 24 hours. Seed 1 stage was initiated by adding 40 ml of pre-seed culture in 200 ml of filter sterilized seed flask medium (containing 6.7 g/l yeast nitrogen base without amino acids (Difco), 2.8 g/l amino acid drop out mix without histidine, uracil and leucine (Clonetech), 200 mg/l of leucine, 40 mg/l of tryptophan, 2 g/l yeast extract (Becton Dickinson), 4 g/l peptone (Becton Dickinson), 19.5 g/l 4-Morpholineethane-sulphonic acid (Sigma), 10 g/l glucose, 5 g/l ethanol, and 50 mg/l Ampicillin) with pH adjusted to 5.5 using 1M $H_2SO_4$) in 1 L flask and incubated at 30° C. and 250 rpm for 24 hours. In the seed 2 stage, 80 ml of seed 1 culture was inoculated in 400 ml of fresh seed flask medium (as described above) in 2 L flask and incubated at 30° C. and 250 rpm for 24 hours.

B.2 Glucose Limited Fed-Batch (GLFB) Phase for Isobutanologen PNY1621 Biomass Generation The growth phase was initiated by inoculating a 2 L Biostat B Plus vessel fermenter containing 1 L growth medium (containing 8 g/l potassium phosphate monobasic, 8 g/l ammonium phosphate monobasic, 3 g/l ammonium sulfate, 3 g/l magnesium sulfate heptahydrate, 0.03 g/l ferrous sulfate heptahydrate, 2 g/l yeast extract, 1 ml/l delft trace elements 1000×, 2 g/l delft vitamin solution 1000×, 4.3 mg/l riboflavin, 50 mg/l ampicillin with pH adjusted to 5.5 using 1M $H_2SO_4$/2M NaOH) at target cell density of 1 g/l by centrifuging cells at 4000 rpm from seed 2 stage. (1000× delft trace mineral solution contains 15 g/l EDTA, 4.5 g/l zinc sulphate heptahydrate, 0.84 g/l manganese chloride dihydrate, 0.3 g/l cobalt(II)chloride hexahydrate, 0.3 g/l copper (II) sulphate pentahydrate, 0.4 g/l di-sodium molybdenum dihydrate, 4.5 g/l calcium chloride dihydrate, 3 g/l iron sulphate heptahydrate, 1 g/l boric acid, 0.1 g/l potassium iodide per liter of solution made in water. 1000× delft vitamin solution contains 0.05 g/l biotin (D−), 1 g/l calcium D(+) panthotenate, 1 g/l nicotinic acid, 25 g/l myo-inositol (for microbiology), 1 g/l thiamine hydrochloride, 1 g/l pyridoxal hydrochloride, 0.2 g/l p-aminobenzoic acid, 0.2 g/l riboflavin (−), and 2 mg/l folic acid). The air flow rate was fixed constant at 1 LPM. Dissolved oxygen was maintained at 30% by varying stirrer speed from 500 to 1200 rpm. The temperature was maintained at 30° C., and pH was maintained at 5.5 using 15% (v/v) ammonia solution. Fermenter was started with initial sugar of 5 g/l glucose and 5 g/l ethanol and RQ-based feed-back feeding was done to maintain RQ=1.25. The feed composition used was 400 g/l glucose and 8 g/l of yeast extract. The harvest time of the fermenter was decided by saturation in feeding rate and/or cell density of around 15 g/l. The samples were taken periodically for analysis with 10 ml of sample each time. A portion of sample was used for dry cell weight measurement, and the remaining sample was centrifuged and stored in −80° C. for further analysis using HPLC (Table 4).

TABLE 4

Glucose limited fed-batch growth phase data

| Time (hr) | Cell Density (g/L) | Isobutyric Acid (g/L) | Isobutanol (g/L) |
|---|---|---|---|
| 0 | 1.2 | 0.0 | 0.0 |
| 5 | 3.0 | 0.2 | 0.3 |
| 9 | 3.6 | 0.3 | 0.2 |
| 10 | 10.8 | 1.7 | 1.2 |
| 22 | 13.9 | 2.4 | 1.7 |
| 26 | 14.9 | 2.3 | 1.8 |

B.3 Propagation Phase in 6% Dry Solid Corn Mash Medium

The propagation phase was initiated at a cell density of 1 g/l by centrifuging cells grown in the GLFB at RQ=1.25 and resuspending in 1000 mL of medium containing 6% dry solid corn mash, 2 g/l yeast extract, 30 mg/l thiamine, 30 mg/l nicotinic acid, 5 g/l ethanol, 50 mg/l ampicillin. The temperature was maintained at 30° C., and pH was maintained at 5.5 using 15% (v/v) ammonia solution. The air flow rate was fixed constant at 1 LPM. Dissolved oxygen was maintained at 30% by varying stirrer speed from 400 to 1000 rpm. The samples were taken periodically for analysis with 10 ml of sample each time. A portion of sample was used for dry cell weight measurement, and the remaining sample was centrifuged and stored in −80° C. for further analysis using HPLC (Table 5).

TABLE 5

Propagation phase data

| Time (hr) | Cell Density (g/L) | Isobutyric Acid (g/L) | Isobutanol (g/L) | $q_p$ (g/g dcw/hr) |
|---|---|---|---|---|
| 0 | 1.0 | 0.0 | 0.0 | 0.037 |
| 4 | 2.8 | 0.1 | 0.2 | 0.045 |
| 17 | 6.1 | 0.8 | 3.1 | 0.1 |

C. Production Performance for Substantially and Partially Adapted Cells Under Anaerobic Conditions.

Two production runs were initiated at a cell density of 0.3-0.4 g/L. For substantially adapted cell performance testing, cells were centrifuged from seed stage 2 (A.1) and re-suspended in 800 ml production medium. For partially adapted cell performance testing cells were centrifuged from propagation phase (B.2) and re-suspended in the 800 ml production medium. The production medium contains 2.8 g/l $K_2HPO_4$, 5 g/l ammonium sulphate, 1.9 g/l magnesium sulphate heptahydrate, 6 ml/l of 1000× delft vitamin solution, 6 ml/l of 1000× delft trace solution, 50 mg/l ampicillin and 3.7 g/l yeast dropout without Histidine, Uracil (Clonetech). The temperature was maintained at 30° C., and pH was maintained at 5.2 using KOH. The gas flow rate was maintained at 0.3 LPM nitrogen (anaerobic). The feed composition used was 50% glucose (% w/v). The glucose levels were maintained between 5-50 g/l in fed-batch mode. Sampling was done periodically, and samples were stored in −80° C. freezer for further analysis using HPLC and GC. Sugars and metabolites were analyzed in 1260 infinity HPLC (Agilent Life Sciences; Santa Clara, Calif.) using HPX 87N AMINEX column 300×7.8 mm (BioRad laboratories; Hercules, Calif.).

When substantially adapted and partially adapted cells were tested under similar condition for production no compromise in the isobutanol production performance was observed (Table 6). The cell growth performance in production tank of partially adapted cells (1.9 g/l) was better as compared to substantially adapted cells (1.3 g/l). The partially adapted cells did not show any compromise in effective isobutanol titer.

TABLE 6

Production phase performance of substantially and partially adapted cell

| | Substantially adapted cell performance | | | Partially adapted cell performance | | |
|---|---|---|---|---|---|---|
| Time (hr) | Cell Density (g/L) | Eff. Isobutanol titer (g/L) | $q_p$ (g/g dcw/hr) | Cell Density (g/L) | Eff. Isobutanol titer (g/L) | $q_p$ (g/g dcw/hr) |
| 0 | 0.3 | 0.0 | 0.31 | 0.3 | 0.0 | 0.16 |
| 4 | 0.4 | 0.2 | 0.32 | 0.5 | 0.1 | 0.17 |
| 6 | 0.4 | 0.2 | 0.32 | 0.7 | 0.4 | 0.17 |
| 10 | 0.4 | 0.6 | 0.32 | 0.9 | 0.5 | 0.18 |
| 24 | 1.1 | 4.2 | 0.37 | 1.2 | 3.0 | 0.24 |
| 30 | 1.2 | 7.2 | 0.39 | 1.3 | 5.5 | 0.27 |
| 33 | 1.2 | 8.8 | 0.41 | 1.6 | 7.2 | 0.29 |
| 48 | 1.4 | 16.4 | 0.48 | 1.8 | 15.2 | 0.39 |
| 53 | 1.3 | 20.8 | 0.51 | 1.9 | 18.6 | 0.43 |

Example 2

Effect of Initial Biomass Pitching on Cell Performance in Term of Pathway Adaptation in Propagation Tank Glycerol Stock Preparation.

Cells of the engineered yeast strain PNY1621 were inoculated in 20 ml synthetic complete medium (1× yeast nitrogen base without amino acids (Becton Dickinson), 1× amino acid drop-out without Histidine and Uracil (Clonetech) containing 2 g/l glucose (Sigma) and 2 g/l ethanol) in 125 ml flask. Cells were grown at 30° C. for 24 hours with agitation at 200 rpm. This culture was used to inoculate 90 ml of fresh synthetic complete medium (with 2 g/l ethanol and 2 g/l glucose) in 250 ml flask and grown for 24 hours at 30° C. and 200 rpm. After 24 hours, cells were harvested by centrifugation at 4000 rpm for 5 minutes and re-suspended at an initial $OD_{600nm}$ of 20 in synthetic complete medium containing 2 g/l ethanol and 20% v/v glycerol (Sigma). These cells were distributed in aliquots of 1 ml in screw cap tubes and frozen using slow freezers and stored at −80° C. (glycerol stocks) until use.

Seed Stage

Seed culture was prepared in three stages: pre-seed, seed 1, and seed 2. Pre-seed culture was started by inoculating 3 vials of 20 OD glycerol stock in 100 ml of filter sterilized pre-seed medium (containing 0.65 g/l amino acid dropout without Histidine, Uracil and Leucine (Clonetech), 60 mg/l Leucine (Sigma), 6.5 g/l yeast nitrogen base without amino acids (Difco), 10 g/l glucose, 5 g/l ethanol, 19.5 g/l 4-morpholineethane-sulphonic acid (Sigma), 50 mg/l ampicillin ((Himedia) with pH adjusted to 5.5 using 1M $H_2SO_4$) in 500 ml flask and grown at 30° C. and 250 rpm for 24 hours. Seed 1 stage was initiated by adding 40 ml of pre-seed culture in 200 ml of filter sterilized seed flask medium (containing 6.7 g/l yeast nitrogen base without amino acids (Difco), 2.8 g/l amino acid drop out mix without histidine, uracil and leucine (Clonetech), 200 mg/l of leucine, 40 mg/l of tryptophan, 2 g/l yeast extract (Becton Dickinson), 4 g/l peptone (Becton Dickinson), 19.5 g/l 4-morpholineethanesulphonic acid (Sigma), 10 g/l glucose, 5 g/l ethanol, and 50 mg/l ampicillin) with pH adjusted to 5.5 using 1M $H_2SO_4$) in 1 L flask and incubated at 30° C. and 250 rpm for 24 hours. In the seed 2 stage, 80 ml of seed 1 culture was inoculated in 400 ml of fresh seed flask medium in 2 L flask and incubated at 30° C. and 250 rpm for 24 hours.

Glucose Limited Fed-Batch (GLFB) Phase for Isobutanologen PNY1621 Biomass Generation The growth phase was initiated by inoculating 2 L Biostat B Plus vessel fermenter containing 1 L growth medium (containing 8 g/l potassium phosphate monobasic, 8 g/l ammonium phosphate monobasic, 3 g/l ammonium sulfate, 3 g/l magnesium sulfate heptahydrate, 0.03 g/l ferrous sulfate heptahydrate, 2 g/l yeast extract, 1 ml/l delft trace elements (1000×), 2 g/l delft vitamin solution 1000×, 4.3 mg/l riboflavin, 50 mg/l ampicillin with pH adjusted to 5.5 using 1M $H_2SO_4$/2M NaOH) at target cell density of 1 g/l by centrifuging cells at 4000 rpm from seed 2 stage. The air flow rate was fixed constant at 1 LPM. Dissolved oxygen was maintained at 30% by varying stirrer speed from 500 to 1200 rpm. The temperature was maintained at 30° C., and pH was maintained at 5.5 using 15% (v/v) ammonia solution. Fermenter was started with initial sugar of 5 g/l glucose and 5 g/l ethanol and RQ-based feed-back feeding was done to maintain RQ=1.25. The feed composition used was 400 g/l glucose and 8 g/l of yeast extract. The harvest time of the fermenter was decided by saturation in feeding rate and/or cell density of around 14 g/l. The samples were taken periodically for analysis with 10 ml of sample each time. A portion of sample was used for dry cell weight measurement, and the remaining sample was centrifuged and stored in −80° C. for further analysis using HPLC (Table 7).

TABLE 7

Glucose limited fed-batch growth phase data

| Time (hr) | Cell density (g/L) | Isobutyirc Acid (g/L) | Isobutanol (g/L) |
|---|---|---|---|
| 0 | 1.1 | 0.0 | 0.0 |
| 4 | 1.5 | 0.0 | 0.2 |

TABLE 7-continued

Glucose limited fed-batch growth phase data

| Time (hr) | Cell density (g/L) | Isobutyirc Acid (g/L) | Isobutanol (g/L) |
|---|---|---|---|
| 8 | 3.4 | 0.0 | 0.4 |
| 22 | 9.6 | 1.5 | 0.6 |
| 26 | 14.3 | 2.9 | 1.0 |

Propagation Phase in 6% Dry Solid Corn Mash Medium

Propagation phase was initiated by centrifuging cells grown in the GLFB at RQ=1.25 and re-suspending in 1000 ml of medium containing 6% dry solid corn mash, 2 g/l yeast extract, 30 mg/l thiamine, 30 mg/l nicotinic acid, 5 g/l ethanol, 50 mg/l ampicillin. The temperature was maintained at 30° C., and pH was maintained at 5.5 using 15% (v/v) ammonia solution. The air flow rate was fixed constant at 1 LPM. Dissolved oxygen was maintained at 30% by varying stirrer speed from 400 to 1000 rpm. To test effect of initial biomass loading in propagation tank, two propagation tanks were run at an initial cell density of 0.25 and 1 g/l respectively. The samples were taken periodically for analysis with 10 ml of sample each time. A portion of sample was used for dry cell weight measurement, and the remaining sample was centrifuged and stored in −80° C. for further analysis using HPLC.

When the cells were pitched at different levels in the propagation tank, the difference in cell growth and product profile was observed (Table 8). The cells pitched at a lower cell density (0.25 g/l) grew to final biomass of 4.7 g/L (5 generations) and the cells pitched at a higher cell density (1 g/l) grew to final biomass of 7.2 g/L (2.5-3 generation). The isobutanol produced in low pitched tank (titer=4 g/L) was more than high pitched tank (titer=2.5 g/L) even though cell density was higher in high pitch tank. This could indicate a higher $q_p$ in the low pitch tank as compared to the $q_p$ of the culture in the high pitch tank.

TABLE 8

Propagation phase data: Effect of initial biomass loading (pitching) on cell growth and product profile

| | Low Pitch at 0.25 g/L | | | High Pitch at 1 g/L | | |
|---|---|---|---|---|---|---|
| Time (hr) | Cell Denisty (g/L) | Isobutyric Acid (g/L) | Isobutanol (g/L) | Cell Density (g/L) | Isobutyric Acid (g/L) | Isobutanol (g/L) |
| 0 | 0.3 | 0.0 | 0.0 | 1.0 | 0.0 | 0.0 |
| 3 | 1.0 | 0.1 | 0.1 | 2.5 | 0.2 | 0.3 |
| 16 | 4.7 | 0.4 | 3.9 | 7.2 | 0.9 | 2.5 |

What is claimed is:

1. A process for producing a culture of cells comprising an engineered butanol biosynthetic pathway:
   a) providing a cell culture of recombinant microorganisms comprising an engineered butanol biosynthetic pathway, wherein the recombinant microorganisms produce butanol;
   b) growing the culture of recombinant microorganisms in a propagation phase wherein the propagation phase is characterized by aerobic conditions and a butanol concentration of about 0 g/L to about 10 g/L; and
   c) growing the culture of step b) in a production phase wherein the production phase is characterized by anaerobic conditions and a butanol concentration of at least 25 g/L, wherein the recombinant microorganism is selected from a genus from the group consisting of Clostridium, Zymomonas, Escherichia, Salmonella, Serratia, Erwinia, Klebsiella, Shigella, Rhodococcus, Pseudomonas, Bacillus, Lactobacillus, Lactococcus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma, and Saccharomyces.

2. The process of claim 1, wherein the engineered butanol biosynthetic pathway is selected from the group consisting of:
   (a) a 1-butanol biosynthetic pathway;
   (b) a 2-butanol biosynthetic pathway; and
   (c) an isobutanol biosynthetic pathway.

3. The process of claim 1, wherein the rate of butanol production of the provided cell culture of recombinant microorganisms is less than 0.20 grams of butanol per gram of dry cell weight of cells per hour (g/g dcw/hr).

4. The process of claim 1, wherein the cell culture of recombinant microorganisms is grown under adaptive conditions selected from at least one of a source of carbon substrate, a dissolved oxygen concentration, a temperature, a pH, a substrate concentration, a butanol concentration, a 2-butanone concentration, or a component of the fermentation medium.

5. The process of claim 4, wherein the adaptive condition comprises a substrate concentration and a dissolved oxygen concentration.

6. The process of claim 5, wherein the substrate is glucose.

7. The process of claim 6, wherein the glucose concentration is about 1 g/L to about 50 g/L.

8. The process of claim 7, wherein the dissolved oxygen concentration is greater than 5%.

9. The process of claim 8, wherein specific oxygen uptake rate (Sp. OUR) of the recombinant microorganism is about 0.5 millimoles per gram cells per hour (mM/g cells/hr) to about 5 mM/g cells/hr.

10. The process of claim 4, wherein the cell culture is characterized by at least one of an increase in biomass production, a reduction in the amount of time for the fermentation, or a reduction or elimination of the production of an inhibitory product.

11. The process of claim 10, wherein growing the culture under adaptive conditions increases the biomass production of the culture to a cell density of about 5 g/L to about 15 g/L.

12. The process of claim 10, wherein the inhibitory product is isobutyric acid.

13. The process of claim 12, wherein the growing the culture under adaptive conditions reduces the isobutyric acid concentration to about 0.1 g/L to about 2.5 g/L.

14. The process of claim 4, wherein the dissolved oxygen concentration is less than 5%.

15. The process of claim 14, wherein specific oxygen uptake rate (Sp. OUR) of the recombinant microorganism is about 0 millimoles per gram cells per hour (mM/g cells/hour) to about 2.5 mM/g cells/hr.

16. The process of claim 4, wherein the cell culture is characterized by at least one of an increase in biomass production, a reduction in the amount of time for the fermentation, an increase in butanol yield, an increase in butanol productivity, an increase in biomass yield, or a delay in the production of an inhibitory product.

17. The process of claim 16, wherein growing the culture under adaptive conditions increases the biomass production of the culture such that the culture is capable of growing for at least one generation in the fermentation.

18. The process of claim 16, wherein growing the culture under adaptive conditions increases the biomass production of the culture such that the culture is capable of growing for at least two generations in the fermentation.

19. The process of claim 16, wherein the butanol yield is increased to at least 30 g/L.

* * * * *